United States Patent
Cunningham et al.

(10) Patent No.: US 6,372,431 B1
(45) Date of Patent: Apr. 16, 2002

(54) MAMMALIAN TOXICOLOGICAL RESPONSE MARKERS

(75) Inventors: Mary Jane Cunningham, Sunnyvale; Gary B. Zweiger, Mountain View; Matthew R. Kaser, Castro Valley; Scott R. Panzer, Sunnyvale; Jeffrey J. Seilhamer, Los Altos Hills; Henry Yue, Sunnyvale; Mariah R. Baughn, San Leandro; Yalda Azimzai, Hayward; Preeti Lal, Santa Clara, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/443,184

(22) Filed: Nov. 19, 1999

(51) Int. Cl.[7] ............................. C12Q 1/68; C12Q 1/00; C07H 21/04
(52) U.S. Cl. ................................. 435/6; 435/4; 435/7.1; 435/DIG. 1; 435/DIG. 14; 435/DIG. 17; 536/231; 436/501
(58) Field of Search ........................... 435/7.1, DIG. 1, 435/DIG. 2, DIG. 14, DIG. 17, 6, 4; 536/23.1; 436/501

(56) References Cited

PUBLICATIONS

Qu, S. and Stacey, N.H., "Formation and persistence of DNA adducts in different target tissues of rats after multiple administration of benzo[a]pyrene", *Carcinogenesis* 17(1): 53–59 (1996).

Kröger, H. et al., "Protection From Acetaminophen–Induced Liver Damage by the Synergistic Action of Low Doses of the Poly (ADP–ribose) Polymerase–Inhibitor Nicotinamide and the Antioxidant N–Acetylcysteine or the Amino Acid L–Methionine", *Gen. Pharmac.* 28(2): 257–263 (1997).

Hasmall, S.C. and Roberts, R.A., "The Perturbation of Apoptosis and Mitosis by Drugs and Xenobiotics", *Pharmacol. Ther.* 82(1): 63–70 (1999).

Gelman, L. et al., "An update on the mechanisms of action of the peroxisome proliferator–activated receptors (PPARs) and their roles in inflammation and cancer", *C.M.L.S.* 55: 932–943 (1999).

Kawashima, H. et al., "Protein Expression, Characterization, and Regulation of CYP4F4 and CYP4F5 Cloned from Rat Brain", *Archives of Biochemistry and Biophysics* 347 (1): 148–154 (1997).

Zhou, S. and Wallace, K.B., "The Effect of Peroxisome Proliferators on Mitochondrial Bioenergetics", *Toxicological Sciences* 48: 82–89 (1999).

Waterfield, C.J. et al., "Investigations into the effects of various hepatotoxic compounds on urinary and liver taurine levels in rats", *Arch. Toxicol.* 67: 244–254 (1993).

Soares, M.B. et al., "Contruction and characterization of a normalized cDNA library", *Proc. Natl. Sci. Acad. USA* 91(20): 9228–9232 (1994).

*Primary Examiner*—Padmashri Ponnaluri
(74) *Attorney, Agent, or Firm*—Incyte Genomics, Inc.

(57) ABSTRACT

The present invention relates to mammalian nucleic acid and protein molecules comprising a plurality of nucleic acid and protein molecules. The mammalian nucleic acid molecules can be used as hybridizable array elements in a microarray in diagnostic and therapeutic applications including detecting metabolic and toxicological responses, and in monitoring drug mechanism of action. The protein molecules can be used in a pharmaceutical composition. The present invention also relates to methods for screening compounds and therapeutics for metabolic responses indicative of a toxic compound or molecule.

7 Claims, No Drawings

MAMMALIAN TOXICOLOGICAL RESPONSE MARKERS

FIELD OF THE INVENTION

The present invention relates to mammalian nucleic acid and protein molecules, and methods for their use in diagnostic and therapeutic applications including detecting metabolic and toxicological responses, and in monitoring drug mechanism of action.

BACKGROUND OF THE INVENTION

Toxicity testing is a mandatory and time-consuming part of drug development programs in the pharmaceutical industry. A more rapid screen to determine the effects upon metabolism and to detect toxicity of lead drug candidates may be the use of gene expression microarrays. For example, microarrays of various kinds may be produced using full length genes or gene fragments. These arrays can then be used to test samples treated with the drug candidates to elucidate the gene expression pattern associated with drug treatment. This gene pattern can be compared with gene expression patterns associated with compounds which produce known metabolic and toxicological responses.

Benzo(a)pyrene is a known rodent and likely human carcinogen and is the prototype of a class of compounds, the polycyclic aromatic hydrocarbons (PAH). It is metabolized by several forms of cytochrome P450 (P450 isozymes) and associated enzymes to form both activated and detoxified metabolites. The ultimate metabolites are the bay-region diol epoxide, benzo(a)pyrene-7,8-diol-9,10-epoxide (BPDE) and the K-region diol epoxide, 9-hydroxy benzo(a)pyrene-4,5-oxide, both of which induce formation of DNA adducts. DNA adducts have been shown to persist in rat liver up to 56 days following treatment with benzo(a)pyrene at a dose of 10 mg/kg body weight three times per week for two weeks (Qu and Stacey (1996) Carcinogenesis 17:53–59).

Acetaminophen is a widely-used analgesic. It is metabolized by specific cytochrome P450 isozymes with the majority of the drug undergoing detoxification by glucuronic acid, sulfate and glutathione conjugation pathways. However, at supratherapeutic doses, acetaminophen is metabolized to an active intermediate, N-acetyl-p-benzoquinone imine (NAPQI) which can cause hepatic and renal failure. NAPQI then binds to sulfhydryl groups of proteins causing their inactivation and leading to subsequent cell death (Kroger et al. (1997) Gen. Pharmacol. 28:257–263).

Clofibrate is an hypolidemic drug which lowers elevated levels of serum triglycerides. In rodents, chronic treatment produces hepatomegaly and an increase in hepatic peroxisomes (peroxisome proliferation). Peroxisome proliferators (PPs) are a class of drugs which activate the PP-activated receptor in rodent liver, leading to enzyme induction, stimulation of S-phase, and a suppression of apoptosis (Hasmall and Roberts (1999) Pharmacol. Ther. 82:63–70). PPs include the fibrate class of hypolidemic drugs, phenobarbitone, thiazolidinediones, certain non-steroidal anti-inflammatory drugs, and naturally-occurring fatty acid-derived molecules (Gelman et al. (1999) Cell. Mol. Life Sci. 55:932–943). Clofibrate has been shown to increase levels of cytochrome P450 4A. It is also involved in transcription of β-oxidation genes as well as induction of PP-activated receptors (Kawashima et al. (1997) Arch. Biochem. Biophys. 347:148–154). Peroxisome proliferation that is induced by both clofibrate and the chemically-related compound fenofibrate is mediated by a common inhibitory effect on mitochondrial membrane depolarization (Zhou and Wallace (1999) Toxicol. Sci. 48:82–89).

Toxicological effects in the liver are also induced by other compounds. These can include carbon tetrachloride (a necrotic agent), hydrazine (a steatotic agent), α-naphthylisothiocyanate (a cholestatic agent), 4-acetylaminofluorene (a liver mitogen), and their corresponding metabolites, which are used in experimental protocols to measure toxicological responses (Waterfield et al. (1993) Arch. Toxicol. 67:244–254).

The present invention provides mammalian nucleic acid and protein molecules, their use in diagnostic and therapeutic applications including detecting metabolic and toxicological responses, and in monitoring drug mechanism of action.

SUMMARY OF THE INVENTION

The invention provides a method for detecting or diagnosing the effect of a test compound or molecule associated with increased or decreased levels of nucleic acid molecules in a mammalian subject. The method comprises treating a mammalian subject with a known toxic compound or molecule which elicits a toxicological response, measuring levels of a plurality of nucleic acid molecules, selecting from the plurality of nucleic acid molecules those nucleic acid molecules that have levels modulated in samples treated with known toxic compounds or molecules when compared with untreated samples. Some of the levels may be upregulated by a toxic compound or molecule, others may be downregulated by a toxic compound or molecule, and still others may be upregulated with one known toxic compound or molecule and be downregulated with another known toxic compound or molecule. The selected nucleic acid molecules which are upregulated and downregulated by a known toxic compound or molecule are arrayed upon a substrate. The method further comprises measuring levels of nucleic acid molecules in the sample after the sample is treated with the toxic compound or molecule. Levels of nucleic acid molecules in a sample so treated are then compared with the plurality of the arrayed nucleic acid molecules to identify which sample nucleic acid molecules are upregulated and downregulated by the test compound or molecule. In one embodiment, the nucleic acid molecules are hybridizable array elements of a microarray.

Preferably, the comparing comprises contacting the arrayed nucleic acid molecules with the sample nucleic acid molecules under conditions effective to form hybridization complexes between the arrayed nucleic acid molecules and the sample nucleic acid molecules; and detecting the presence or absence of the hybridization complexes. In this context, similarity may mean that at least 1, preferably at least 5, more preferably at least 10, of the upregulated arrayed nucleic acid molecules form hybridization complexes with the sample nucleic acid molecules at least once during a time course to a greater extent than would the probes derived from a sample not treated with the test compound or molecule or a known toxic compound or molecule. Similarity may also mean that at least 1, preferably at least 5, more preferably at least 10, of the downregulated arrayed nucleic acid molecules form hybridization complexes with the sample nucleic acid molecules at least once during a time course to a lesser extent than would the sample nucleic acid molecules of a sample not treated with the test compound or a known toxic compound. In one aspect, the arrayed nucleic acid molecules comprise SEQ ID NOs: 1–47 or fragments thereof.

Preferred toxic compounds are selected from the group consisting of hypolipidemic drugs, n-alkylcarboxylic acids, n-alkylcarboxylic acid precursors, azole antifungal compounds, leukotriene D4 antagonists, herbicides, pesticides, phthalate esters, phenyl acetate, dehydroepiandrosterone (DHEA), oleic acid, methanol and their corresponding metabolites, acetaminophen and its corresponding metabolites, benzo(a)pyrene, 3-methylcholanthrene, benz(a)anthracene, 7,12-dimethylbenz(a)anthracene, their corresponding metabolites, and the like, carbon tetrachloride, hydrazine, α-naphthylisothiocyanate, 4-acetylaminofluorene, and their corresponding metabolites. Preferred tissues are selected from the group consisting of liver, kidney, brain, spleen, pancreas and lung.

The arrayed nucleic acid molecules comprise fragments of messenger RNA transcripts of genes that are upregulated-or-downregulated at least 2-fold, preferably at least 2.5-fold, more preferably at least 3-fold, in tissues treated with known toxic compounds when compared with untreated tissues. Preferred arrayed nucleic acid molecules are selected from the group consisting of SEQ ID NOs: 1–47 or fragments thereof, some of whose expression is upregulated following treatment with a toxic compound or molecule and others of whose expression is downregulated following treatment with a toxic compound or molecule.

More preferable are SEQ ID NOs:2, 4, 6, 8, 9, and 11 which are upregulated following treatment with a toxic compound or molecule, and SEQ ID NOs: 1, 4, and 7 which are downregulated following treatment with a toxic compound or molecule.

The invention also provides a method comprising measuring levels of nucleic acid molecules in a sample after the sample is treated with a test compound or molecule. Levels of nucleic acid molecules in a sample so treated are then compared with the plurality of the arrayed nucleic acid molecules to identify which sample nucleic acid molecules are upregulated and downregulated by the test compound or molecule. In one embodiment, the nucleic acid molecules are hybridizable array elements of a microarray.

Alternatively, the invention provides methods for screening a sample for a metabolic response to a test compound or molecule.

Alternatively, the invention provides methods for screening a test compound or molecule for a previously unknown metabolic response.

In another aspect, the invention provides methods for preventing a toxicological response by administering complementary nucleotide molecules against one or more selected upregulated nucleic acid molecules or a ribozyme that specifically cleaves such molecules. Alternatively, a toxicological response may be prevented by administering sense nucleotide molecules for one or more selected downregulated nucleic acid molecules.

In yet another aspect, the invention provides methods for preventing a toxicological response by administering an agonist which initiates transcription of a gene comprising a downregulated nucleic acid molecule of the invention. Alternatively, a toxicological response may be prevented by administering an antagonist which prevents transcription of a gene comprising an upregulated nucleic acid molecule of the invention.

In another aspect, the invention provides nucleic acid molecules whose transcript levels are modulated in a sample during a metabolic response to a toxic compound or molecule. The invention also provides nucleic acid molecules whose transcript levels are upregulated in a sample during a metabolic response to a toxic compound or molecule. The invention also provides nucleic acid molecules whose transcript levels are downregulated in a sample during a metabolic response to a toxic compound or molecule. Upregulation or downregulation is at least 2-fold, more preferably at least 2.5-fold, even more preferably at least 3-fold. The metabolic response to a toxic compound or molecule may be a toxicological response. The invention also provides mammalian nucleic acid molecules which are homologous to the upregulated and downregulated nucleic acid molecules. In one aspect, preferred arrayed nucleic acid molecules are selected from the group consisting of SEQ ID NOs: 1–47, or fragments thereof.

The invention also provides a method for using a molecule selected from SEQ ID NOs: 1–59 or a portion thereof to screen a library of molecules to identify at least one ligand which specifically binds the selected molecule, the method comprising combining the selected molecule with the library of molecules under conditions allowing specific binding, and detecting specific binding, thereby identifying a ligand which specifically binds the selected molecule.

Such libraries include DNA and RNA molecules, peptides, peptide nucleic acids, agonists, antagonists, antibodies, immunoglobulins, drug compounds, pharmaceutical agents, and other ligands. In one aspect, the ligand identified using the method modulates the activity of the selected molecule. In an analogous method, the selected molecule or a portion thereof is used to purify a ligand. The method involves combining the selected molecule or a portion thereof with a sample under conditions to allow specific binding, detecting specific binding between the selected molecule and ligand, recovering the bound selected molecule, and separating the selected molecule from the ligand to obtain purified ligand. The invention further provides a method for using at least a portion of the proteins encoded by SEQ ID NOs:1–47 and the proteins of SEQ ID NOs: 48–59 to produce antibodies.

The invention further provides a method for inserting a marker gene into the genomic DNA of an animal to disrupt the expression of the natural nucleic acid molecule. The invention also provides a method for using the nucleic acid molecule to produce an animal model system, the method comprising constructing a vector containing the nucleic acid molecule; introducing the vector into a totipotent embryonic stem cell; selecting an embryonic stem cell with the vector integrated into genomic DNA; microinjecting the selected cell into a blastocyst, thereby forming a chimeric blastocyst; transferring the chimeric blastocyst into a pseudopregnant dam, wherein the dam gives birth to a chimeric animal containing at least one additional copy of nucleic acid molecule in its germ line; and breeding the chimeric animal to generate a homozygous animal model system.

The invention also provides a substantially purified mammalian protein or a portion thereof. The invention further provides isolated and purified proteins encoded by the nucleic acid molecules of SEQ ID NOs:1–11, 17–33, 36, 39, and 41. The invention further provides isolated and purified protein molecule of SEQ ID NOs:50 and 53. Additionally, the invention provides a pharmaceutical composition comprising a substantially purified mammalian protein or a portion thereof in conjunction with a pharmaceutical carrier.

The invention further provides an isolated and purified mammalian nucleic acid molecule variant having at least 70% nucleic acid sequence identity to the mammalian nucleic acid molecule selected from SEQ ID NO:1–47 and fragments thereof. The invention also provides an isolated and purified nucleic acid molecule having a sequence which is complementary to the mammalian nucleic acid molecule comprising a nucleic acid molecule selected from SEQ ID NO:1–47 and fragments thereof.

The invention further provides an expression vector containing at least a fragment of the mammalian nucleic acid molecule selected from the group consisting of SEQ ID NOs:1–47. In another aspect, the expression vector is contained within a host cell.

The invention also provides a method for producing a mammalian protein, the method comprising the steps of: (a) culturing the host cell containing an expression vector containing a mammalian nucleic acid molecule of the invention under conditions suitable for the expression of the polypeptide; and (b) recovering the polypeptide from the host cell culture.

The invention also provides a pharmaceutical composition comprising a substantially purified mammalian protein encoded by SEQ ID NOs:1–11, 17–33, 36, 39, and 41 and the amino acid sequence of SEQ ID NOs:50 and 53 and fragments thereof, in conjunction with a suitable pharmaceutical carrier.

The invention further includes an isolated and purified antibody which binds to a mammalian protein encoded by SEQ ID NOs:1–11, 17–33, 36, 39, and 41 and mammalian protein of SEQ ID NOs:50 and 53 or fragments thereof. The invention also provides a purified agonist and a purified antagonist.

DESCRIPTION OF THE SEQUENCE LISTING

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing contains the nucleic acid sequence of exemplary mammalian nucleic acid molecules of the invention, SEQ ID NOs:1–47, 60–135, 137, and 138; the protein sequence of exemplary mammalian protein molecules of the invention, SEQ ID NOs:48–59, and 136.

DESCRIPTION OF THE INVENTION

Definitions

"Sample" is used in its broadest sense. A sample containing nucleic acid molecules may comprise a bodily fluid; a cell; an extract from a cell, chromosome, organelle, or membrane isolated from a cell; genomic DNA, RNA, or cDNA in solution or bound to a substrate; a biological tissue or biopsy thereof; a fingerprint or tissue print; natural or synthetic fibres; in a solution; in a liquid suspension; in a gaseous suspension; in an aerosol; and the like.

"Plurality" refers preferably to a group of one or more members, preferably to a group of at least about 10, and more preferably to a group of at least about 100 members, and even more preferably a group of 10,000 members.

"Substrate" refers to a rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Modulates" refers to a change in activity (biological, chemical, or immunological) or lifespan resulting from specific binding between a molecule and either a nucleic acid molecule or a protein.

"Microarray" refers to an ordered arrangement of hybridizable array elements on a substrate. The array elements are arranged so that there are preferably at least ten or more different array elements, more preferably at least 100 array elements, even more preferably at least 1000 array elements, and most preferably 10,000. Furthermore, the hybridization signal from each of the array elements is individually distinguishable. In a preferred embodiment, the array elements comprise nucleic acid molecules.

"Nucleic acid molecule" refers to a nucleic acid, oligonucleotide, nucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded.

"Protein" refers to an amino acid sequence, oligopeptide, peptide, polypeptide, or portions thereof whether naturally occurring or synthetic. Exemplary portions are the first twenty consecutive amino acids of a mammalian protein encoded by SEQ ID NOs:1–11, 17–33, 36, 39, and 41 and mammalian protein of SEQ ID NOs:50 and 53.

"Up-regulated" refers to a nucleic acid molecule whose levels increased in a treated sample compared with the nucleic acid molecule in an untreated sample.

"Down-regulated" refers to nucleic acid molecule whose levels decreased in a treated sample compared with the nucleic acid molecule in an untreated sample.

"Toxic compound" or "toxic agent" is any compound, molecule, or agent that elicits a biochemical, metabolic, and physiological response in an individual or animal, such as i) DNA damage, ii) cell damage, iii) organ damage or cell death, or iv) clinical morbidity or mortality.

"Toxicological response" refers to a biochemical, metabolic, and physiological response in an individual or animal which has been exposed to a toxic compound or agent.

"Fragment" refers to an Incyte clone or any part of a molecule which retains a usable, functional characteristic. Useful fragments include oligonucleotides and polynucleotides which may be used in hybridization or amplification technologies or in regulation of replication, transcription or translation. Exemplary fragments are the first sixty consecutive nucleotides of SEQ ID NOs:1–47. Useful fragments also include polypeptides and protein molecules which have antigenic potential and which may be used with a suitable pharmaceutical carrier in a pharmaceutical composition. Exemplary fragments are the first twenty consecutive amino acids of a mammalian protein encoded by SEQ ID NOs:1–11, 17–33, 36, 39, and 41 and mammalian protein of SEQ ID NOs:50 and 53.

"Hybridization complex" refers to a complex between two nucleic acid molecules by virtue of the formation of hydrogen bonds between purines and pyrimidines.

"Ligand" refers to any compound, molecule, or agent which will bind specifically to a complementary site on a nucleic acid molecule or protein. Such ligands stabilize or modulate the activity of nucleic acid molecules or proteins of the invention and may be composed of at least one of the following: inorganic and organic substances including nucleic acids, proteins, carbohydrates, fats, and lipids.

"Percent identity" or "% identity" refers to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Substantially purified" refers to nucleic acid molecules or proteins that are removed from their natural environment and are isolated or separated, and are at least about 60% free, preferably about 75% free, and most preferably about 90% free, from other components with which they are naturally associated.

The Invention

The present invention provides mammalian nucleic acid and protein molecules and method of using the nucleic acid molecules for screening test compounds and molecules for toxicological responses. Additionally the invention provides methods for characterizing the toxicological responses of a sample to a test compound or molecule. In particular, the present invention provides a composition comprising a plurality of nucleic acid molecules derived from human cDNA libraries, monkey cDNA libraries, mouse cDNA libraries, normal rat liver cDNA libraries, normalized rat liver cDNA libraries, prehybridized rat liver cDNA libraries, subtracted rat liver cDNA libraries, and rat kidney cDNA libraries. The nucleic acid molecules have been further selected for exhibiting upregulated or downregulated gene expression in rat livers when the rats have been exposed to a known hepatotoxin, including a peroxisomal proliferator (PP), acetaminophen or one of its corresponding metabolites, a polycyclic aromatic hydrocarbon (PAH), carbon tetrachloride, hydrazine, α-naphthylisothiocyanate, 4-acetylaminofluorene, and their corresponding metabolites.

PPs include hypolipidemic drugs, such as clofibrate, fenofibrate, clofenic acid, nafenopin, gemfibrozil, ciprofibrate, bezafibrate, halofenate, simfibrate, benzofibrate, etofibrate, WY-14,643, and the like; n-alkylcarboxylic acids, such as trichloroacetic acid, valproic acid, hexanoic acid, and the like; n-alkylcarboxylic acid precursors, such as trichloroethylene, etrachloroethylene, and the like; azole antifungal compounds, such as bifonazole, and the like; leukotriene D4 antagonists; herbicides; pesticides; phthalate esters, such as di-[2-ethylhexyl] phthalate, mono-[2-ethylhexyl]phthalate, and the like; and natural chemicals, such as phenyl acetate, dehydroepiandrosterone (DHEA), oleic acid, methanol, and the like. In a preferred embodiment the toxin is clofibrate, or one of its corresponding metabolites. In another prefered embodiment the toxin is fenofibrate, or one of its corresponding metabolites.

PAHs include compounds such as benzo(a)pyrene, 3-methylcholanthrene, benz(a)anthracene, 7,12-dimethylbenz(a)anthracene, their corresponding metabolites, and the like. In a preferred embodiment the toxin is benzo(a)pyrene, or one of its corresponding metabolites.

SEQ ID NOs:1–16 were identified by their pattern of at least two-fold upregulation or downregulation following hybridization with sample nucleic acid molecules from rat liver tissue treated with a known toxic compound. SEQ ID NOs:17–47 were identified by their homology to the sample nucleic acid molecules from rat liver tissue treated with a known toxic compound. These and other nucleic acid molecules can be immobilized on a substrate as hybridizable array elements in a microarray format. The microarray may be used to characterize gene expression patterns associated with novel compounds to elucidate any toxicological responses or to monitor the effects of treatments during clinical trials or therapy where metabolic responses to toxic compounds may be expected.

When the nucleic acid molecules are employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a toxicological response associated with a test compound or molecule.

The invention also provides a substantially purified and isolated mammalian protein comprising the protein molecule of SEQ ID NOs:50 and 53 or portion thereof. The invention further provides isolated and purified proteins encoded by the nucleic acid molecules of SEQ ID NOs:1–11, 17–33, 36, 39, and 41, or portion thereof.

Furthermore, the present invention provides methods for screening test compounds or therapeutics for potential toxicological responses and for screening a sample's toxicological response to a particular test compound or molecule. Briefly, these methods entail treating a sample with the test compound or molecule to elicit a change in gene expression patterns comprising the expression of a plurality of sample nucleic acid molecules. Nucleic acid molecules are selected by identifying those genes in rat liver or kidney that are upregulated-or-downregulated at least 2-fold, more preferably at least 2.5-fold, most preferably at least 3-fold, when treated with a known toxic compound or molecule. The nucleic acid molecules are arrayed on a substrate. Then, the arrayed nucleic acid molecules and sample nucleic acid molecules are combined under conditions effective to form hybridization complexes which may be detected by methods well known in the art. Detection of higher or lower levels of such hybridization complexes compared with hybridization complexes derived from untreated samples and samples treated with a compound that is known not to induce a toxicological response correlates with a toxicological response of a test compound or a toxicological response to a molecule.

Complementary DNA Libraries

Molecules are identified that reflect all or most of the genes that are expressed in rat liver or kidney. Molecules may be identified by isolating clones derived from several types of rat cDNA libraries, including normal rat cDNA libraries, normalized rat cDNA libraries, prehybridized rat cDNA libraries, and subtracted cDNA libraries. Clone inserts derived from these clones may be partially sequenced to generate expressed sequence tags (ESTs). Molecules are also identified by comparing the clones from rat cDNA libraries with clones from human, monkey, and mouse cDNA libraries using computer software nucleic acid comparison programs such as BLAST (see, e.g., Altschul, S. F. (1993) J. Mol. Evol. 3:290–300; Altschul, et al. (1990) J. Mol. Biol. 215:403–410).

In one embodiment, two collections of ESTs are identified and sequenced. A first collection of ESTs (the originator molecules) are derived from rat liver and kidney and are derived from the cDNA libraries presented in the Examples. A second collection includes ESTs derived from other rat cDNA libraries available in the ZOOSEQ database (Incyte Pharmaceuticals, Inc. Palo Alto Calif.).

The two collections of ESTs are clustered electronically to form master clusters of ESTs. Master clusters are formed by identifying overlapping EST molecules and assembling these ESTs. A nucleic acid fragment assembly tool, such as the Phrap tool (Phil Green, University of Washington) and the GELVIEW fragment assembly system (GCG, Madison Wis.), can be used for this purpose. The minimum number of clones which constitute a cluster is two. In another embodiment, a collection of human genes known to be expressed in response to toxic agents are used to select representative ESTs from the 113 rat cDNA libraries. The master cluster process is repeated for these molecules.

After assembling the clustered consensus nucleic acid sequences, a representative 5' clone is nominated from each master cluster. The most 5' clone is preferred because it is most likely to contain the complete gene. The nomination process is described in greater detail in "Relational Database and System for Storing Information Relating to Biomolecular Sequences and Reagents", U.S. Ser. No. 09/034,807, filed Mar. 4, 1998, herein incorporated in its entirety by reference. The EST molecules are used as array elements on a microarray.

Selection of Arrayed Nucleic Acid Molecules

Samples are treated, preferably at subchronic doses, with one or more known toxic compounds over a defined time course. Preferably, the agents are peroxisomal proliferators (PPs), acetaminophen or one of its corresponding metabolites, polycyclic aromatic hydrocarbons (PAHs), carbon tetrachloride, hydrazine, $\alpha$-naphthylisothiocyanate, 4-acetylaminofluorene, or their corresponding metabolites.

The gene expression patterns derived from such treated biological samples can be compared with the gene expression patterns derived from untreated biological samples to identify and select nucleic acid molecules whose expression is either upregulated or downregulated due to the response to the toxic compounds. These selected molecules may then be employed as array elements alone or in combination with other array element molecules. Such a microarray is particularly useful to detect and characterize gene expression patterns associated with known toxic compounds. Such gene expression patterns can then be used for comparison to identify other compounds which also elicit a toxicological response.

The arrayed nucleic acid molecules can be manipulated to optimize their performance in hybridization. To optimize hybridization, the arrayed nucleic acid molecules are examined using a computer algorithm to identify portions of genes without potential secondary structure. Such computer algorithms are well known in the art and are part of OLIGO 4.06 primer analysis software (National Biosciences, Plymouth Minn.) or LASERGENE software (DNASTAR, Madison Wis.). These programs can search within nucleic acid sequences to identify stem loop structures and tandem repeats and to analyze G+C content of the sequence (those molecules with a G+C content greater than 60% are excluded). Alternatively, the arrayed nucleic acid molecules can be optimized by trial and error. Experiments can be performed to determine whether sample nucleic acid molecules and complementary arrayed nucleic acid molecules hybridize optimally under experimental conditions.

The arrayed nucleic acid molecules can be any RNA-like or DNA-like material, such as mRNAs, cDNAs, genomic DNA, peptide nucleic acids, branched DNAs and the like. The arrayed nucleic acid molecules can be in sense or antisense orientations.

In one embodiment, the arrayed nucleic acid molecules are cDNAs. The size of the DNA sequence of interest may vary, and is preferably from 50 to 10,000 nucleotides, more preferably from 150 to 3,500 nucleotides. In a second embodiment, the nucleic acid molecules are vector DNAs. In this case the size of the DNA sequence of interest, i.e., the insert sequence, may vary from about 50 to 10,000 nucleotides, more preferably from about 150 to 3,500 nucleotides.

The nucleic acid molecule sequences of the Sequence Listing have been prepared by current, state-of-the-art, automated methods and, as such, may contain occasional sequencing errors and unidentified nucleotides. Nucleotide analogues can be incorporated into the nucleic acid molecules by methods well known in the art. The only requirement is that the incorporated nucleotide analogues must serve to base pair with sample nucleic acid molecules. For example, certain guanine nucleotides can be substituted with hypoxanthine which base pairs with cytosine residues. However, these base pairs are less stable than those between guanine and cytosine. Alternatively, adenine nucleotides can be substituted with 2,6-diaminopurine which can form stronger base pairs than those between adenine and thymidine. Additionally, the nucleic acid molecules can include nucleotides that have been derivatized chemically or enzymatically. Typical modifications include derivatization with acyl, alkyl, aryl or amino groups.

The nucleic acid molecules can be immobilized on a substrate via chemical bonding. Furthermore, the molecules do not have to be directly bound to the substrate, but rather can be bound to the substrate through a linker group. The linker groups are typically about 6 to 50 atoms long to provide exposure to the bound nucleic acid molecule. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the nucleic acid molecule. Preferred substrates are any suitable rigid or semirigid support, including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the arrayed nucleic acid molecules are bound.

The samples can be any sample comprising sample nucleic acid molecules and obtained from any bodily fluid (blood, urine, saliva, phlegm, gastric juices, etc.), cultured cells, biopsies, or other tissue preparations. The samples can be derived from any species, but preferably from eukaryotic species, and more preferably from mammalian species such as rat and human.

DNA or RNA can be isolated from the sample according to any of a number of methods well known to those of skill in the art. For example, methods of purification of nucleic acids are described in Tijssen, P. (1993) *Laboratory Techniques in Biochemistry and Molecular Biology: Hybridization With Nucleic Acid Probes, Part I. Theory and Nucleic Acid Preparation*, Elsevier, New York, N.Y. In one preferred embodiment, total RNA is isolated using the TRIZOL total RNA isolation reagent (Life Technologies, Inc., Gaithersburg Md.) and mRNA is isolated using oligo d(T) column chromatography or glass beads. When sample nucleic acid molecules are amplified it is desirable to amplify the sample nucleic acid molecules and maintain the relative abundances of the original sample, including low abundance transcripts. RNA can be amplified in vitro, in situ, or in vivo (See Eberwine U.S. Pat. No. 5,514,545).

It is also advantageous to include controls within the sample to assure that amplification and labeling procedures do not change the true distribution of nucleic acid molecules in a sample. For this purpose, a sample is spiked with an amount of a control nucleic acid molecule predetermined to be detectable upon hybridization to its complementary arrayed nucleic acid molecule and the composition of nucleic acid molecules includes reference nucleic acid molecules which specifically hybridize with the control arrayed nucleic acid molecules. After hybridization and processing, the hybridization signals obtained should reflect accurately the amounts of control arrayed nucleic acid molecules added to the sample.

Prior to hybridization, it may be desirable to fragment the sample nucleic acid molecules. Fragmentation improves hybridization by minimizing secondary structure and cross-hybridization to other sample nucleic acid molecules in the sample or noncomplementary nucleic acid molecules. Fragmentation can be performed by mechanical or chemical means.

Labeling

The sample nucleic acid molecules may be labeled with one or more labeling moieties to allow for detection of hybridized arrayed/sample nucleic acid molecule complexes. The labeling moieties can include compositions that can be detected by spectroscopic, photochemical, biochemical, bioelectronic, immunochemical, electrical, optical or chemical means. The labeling moieties include radioisotopes, such as $^{32}P$, $^{33}P$ or $^{35}S$, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like. Preferred fluorescent markers include Cy3 and Cy5 fluorophores (Amersham Pharmacia Biotech, Piscataway N.J.).

Hybridization

The nulceic acid molecule sequence of SEQ ID NOs:1–47 and fragments thereof can be used in various hybridization technologies for various purposes. Hybridization probes may be designed or derived from SEQ ID NOs:1–47. Such probes may be made from a highly specific region such as the 5' regulatory region or from a conserved motif, and used in protocols to identify naturally occurring sequences encoding the mammalian protein, allelic variants, or related sequences, and should preferably have at least 50% sequence identity to any of the protein sequences. The hybridization probes of the subject invention may be DNA or RNA and may be derived from the sequence of SEQ ID NOs:1–47 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid sequence may be used to produce an mRNA probe in vitro by addition of an RNA polymerase and labeled nucleic acid molecules. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, additions of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 and a blocking agent such as salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Hybridization specificity can be evaluated by comparing the hybridization of specificity-control nucleic acid molecules to specificity-control sample nucleic acid molecules that are added to a sample in a known amount. The specificity-control arrayed nucleic acid molecules may have one or more sequence mismatches compared with the corresponding arrayed nucleic acid molecules. In this manner, whether only complementary arrayed nucleic acid molecules are hybridizing to the sample nucleic acid molecules or whether mismatched hybrid duplexes are forming is determined.

Hybridization reactions can be performed in absolute or differential hybridization formats. In the absolute hybridization format, nucleic acid molecules from one sample are hybridized to the molecules in a microarray format and signals detected after hybridization complex formation correlate to nucleic acid molecule levels in a sample. In the differential hybridization format, the differential expression of a set of genes in two biological samples is analyzed. For differential hybridization, nucleic acid molecules from both biological samples are prepared and labeled with different labeling moieties. A mixture of the two labeled nucleic acid molecules is added to a microarray. The microarray is then examined under conditions in which the emissions from the two different labels are individually detectable. Molecules in the microarray that are hybridized to substantially equal numbers of nucleic acid molecules derived from both biological samples give a distinct combined fluorescence (Shalon et al. PCT publication WO95/35505). In a preferred embodiment, the labels are fluorescent markers with distinguishable emission spectra, such as Cy3 and Cy5 fluorophores.

After hybridization, the microarray is washed to remove nonhybridized nucleic acid molecules and complex formation between the hybridizable array elements and the nucleic acid molecules is detected. Methods for detecting complex formation are well known to those skilled in the art. In a preferred embodiment, the nucleic acid molecules are labeled with a fluorescent label and measurement of levels and patterns of fluorescence indicative of complex formation is accomplished by fluorescence microscopy, preferably confocal fluorescence microscopy.

In a differential hybridization experiment, nucleic acid molecules from two or more different biological samples are labeled with two or more different fluorescent labels with different emission wavelengths. Fluorescent signals are detected separately with different photomultipliers set to detect specific wavelengths. The relative abundances/expression levels of the nucleic acid molecules in two or more samples is obtained.

Typically, microarray fluorescence intensities can be normalized to take into account variations in hybridization intensities when more than one microarray is used under similar test conditions. In a preferred embodiment, individual arrayed-sample nucleic acid molecule complex hybridization intensities are normalized using the intensities derived from internal normalization controls contained on each microarray.

The labeled sample emits specific wavelengths which are detected using a plurality of photomultipliers. The nucleic acid molecules whose relative abundance/expression levels are modulated by treatment of a sample with a known toxic compound can be used as hybridizable elements in a microarray. Such a microarray can be employed to identify expression profiles associated with particular toxicological responses. Then, a particular subset of these photomultipliers set to detect specific wavelengths. The relative expression levels of the arrayed nucleic acid molecules can be identified as to which arrayed nucleic acid molecule expression is modulated in response to a particular toxicological agent. These photomultipliers are set to detect specific wavelengths. The relative expression levels of the nucleic acid molecules can be employed to identify other compounds with a similar toxicological response.

Alternatively, for some treatments with known side effects, the microarray, and expression patterns derived therefrom, is employed to prospectively define the treatment regimen. A dosage is established that minimizes expression patterns associated with undesirable side effects. This approach may be more sensitive and rapid than waiting for the patient to show toxicological side effects before altering the course of treatment.

Generally, the method for screening a library of test compounds or molecules to identify those with a toxicological response entails selecting a plurality of arrayed genes whose expression levels are modulated in tissues treated with known toxic compounds when compared with untreated tissues. Then a sample is treated with the test compound or molecule to induce a pattern of gene expression comprising the expression of a plurality of sample nucleic acid molecules. Tissues from a mammalian subject treated at various dosages of the test compound may be screened to determine which doses may be toxic.

Then, the expression levels of the arrayed genes and the sample nucleic acid molecules are compared to identify those compounds that induce expression levels of the sample nucleic acid molecules that are similar to those of the arrayed genes. In one preferred embodiment, gene expression levels are compared by contacting the arrayed genes with the sample nucleic acid molecules under conditions effective to form hybridization complexes between arrayed genes and sample nucleic acid molecules; and detecting the presence or absence of the hybridization complexes.

Similarity may mean that at least 1, preferably at least 5, more preferably at least 10, of the upregulated arrayed genes form hybridization complexes with the sample nucleic acid molecules at least once during a time course to a greater extent than would the nucleic acid molecules of a sample not treated with the test compound. Similarity may also mean that at least 1, preferably at least 5, more preferably at least 10, of the downregulated nucleic acid molecules form hybridization complexes with the arrayed genes at least once during a time course to a lesser extent than would the nucleic acid molecules of a sample not treated with the test compound.

Such a similarity of expression patterns means that a toxicological response is associated with the compound or therapeutic tested. Preferably, the toxic compounds belong to the class of peroxisomal proliferators (PPs), including hypolipidemic drugs, such as clofibrate, fenofibrate, clofenic acid, nafenopin, gemfibrozil, ciprofibrate, bezafibrate, halofenate, simfibrate, benzofibrate, etofibrate, WY-14,643, and the like; n-alkylcarboxylic acids, such as trichloroacetic acid, valproic acid, hexanoic acid, and the like; n-alkylcarboxylic acid precursors, such as trichloroethylene, etrachloroethylene, and the like; azole antifungal compounds, such as bifonazole, and the like; leukotriene D4 antagonists; herbicides; pesticides; phthalate esters, such as di-[2-ethylhexyl]phthalate, mono-[2-ethylhexyl]phthalate, and the like; and natural chemicals, such as phenyl acetate, dehydroepiandrosterone (DHEA), oleic acid, methanol, and the like. In another embodiment, the toxic compound is acetaminophen or one of its corresponding metabolites. In yet another embodiment, the toxic compounds are polycyclic aromatic hydrocarbons (PAHs), including compounds such as benzo(a)pyrene, 3-methylcholanthrene, benz(a)anthracene, 7,12-dimethylbenz(a)anthracene, their corresponding metabolites, and the like. Of particular interest is the study of the toxicological responses of these compounds on the liver, kidney, brain, spleen, pancreas, and lung.

Modification of Gene Expression Using Nucleic Acids

Gene expression may be modified by designing complementary or antisense molecules (DNA, RNA, or PNA) to the control, 5', 3', or other regulatory regions of the mammalian gene. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library of nucleic acid molecules or fragments thereof may be screened to identify those which specifically bind a regulatory, nontranslated sequence .

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio-groups renders the molecule less available to endogenous endonucleases.

Screening Assays

The nucleic acid molecule encoding the mammalian protein may be used to screen a library of molecules for specific binding affinity. The libraries may be DNA molecules, RNA molecules, PNAs, peptides, proteins such as transcription factors, enhancers, repressors, and other ligands which regulate the activity, replication, transcription, or translation of the nucleic acid molecule in the biological system. The assay involves combining the mammalian nucleic acid molecule or a fragment thereof with the library of molecules under conditions allowing specific binding, and detecting specific binding to identify at least one molecule which specifically binds the nucleic acid molecule.

Similarly the mammalian protein or a portion thereof may be used to screen libraries of molecules in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs, or any other ligand, which specifically binds the protein. One method for high throughput screening using very small assay volumes and very small amounts of test compound is described in U.S. Pat. No. 5,876,946, incorporated herein by reference, which screens large numbers of molecules for enzyme inhibition or receptor binding.

Purification of Ligand

The nucleic acid molecule or a fragment thereof may be used to purify a ligand from a sample. A method for using a mammalian nucleic acid molecule or a fragment thereof to purify a ligand would involve combining the nucleic acid molecule or a fragment thereof with a sample under conditions to allow specific binding, detecting specific binding, recovering the bound protein, and using an appropriate agent to separate the nucleic acid molecule from the purified ligand.

Similarly, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound ligand, and using an appropriate chaotropic agent to separate the protein from the purified ligand.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

MODEL SYSTEMS

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred or outbred rodent strains provide a convenient model for investigation of the physiological consequences of under- or over-expression of genes of interest and for the development of methods for diagnosis and treatment of diseases. A mammal inbred to over-express a particular gene, so that the protein is secreted in milk, may also serve as a convenient source of the protein expressed by that gene.

Toxicology

Toxicology is the study of the effects of test compounds, molecules, or toxic agents on living systems to identify adverse effects. The majority of toxicity studies are performed on rats or mice to help predict whether adverse effects of agents will occur in humans. Observation of qualitative and quantitative changes in physiology, behavior, homeostatic, developmental, and reproductive processes, and lethality are used to generate profiles of safe or toxic responses and to assess the consequences on human health following exposure to the agent.

Toxicological tests measure the effects of a single, repeated, or long-term exposure of a subject to a substance. Substances may be tested for specific endpoints such as cytotoxicity, mutagenicity, carcinogenicity and teratogenicity. Degree of response varies according to the route of exposure (contact, ingestion, injection, or inhalation), age, sex, genetic makeup, and health status of the subject. Other tests establish the toxicokinetic and toxicodynamic properties of substances. Toxicokinetic studies trace the absorption, distribution in subject tissues, metabolism, storage, and excretion of substances. Toxicodynamic studies chart biological responses that are consequences of the presence of the substance in the subject tissues.

Genetic toxicology identifies and analyzes the ability of an agent to produce damage at a cellular or subcellular level. Such genotoxic agents usually have common chemical or physical properties that facilitate interaction with nucleic acids and are most harmful when mutated chromosomes are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle which allows investigators to breed sufficient quantities of individual animals to satisfy statistical requirements.

All types of toxicology studies on experimental animals involve preparation of a suitable form of the compound for administration, selection of the route of administration, and selection of a species which resembles the species of pharmacological interest. Dose concentrations of the compound are varied to identify, measure, and investigate a range of dose-related effects related to exposure.

Acute toxicity tests are based on a single administration of the agent to the subject to determine the symptomology or lethality of the agent. Three experiments are conducted; an experiment to define the initial dose range; an experiment to narrow the range of effective doses; and a final experiment to establish the dose-response curve.

Prolonged and subchronic toxicity tests are based on the repeated administration of the agent. Rat and dog are commonly used in these studies to provide data from species in different taxonomic orders. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of at least one test group plus one control group are used. Animals are quarantined, examined for health, and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. No. 4,736,866; U.S. Pat. No. 5,175,383; and U.S. Pat. No. 5,767,337; incorporated herein by reference). In some cases, the introduced gene may be activated at a specific time in a specific tissue type during fetal development or postnatally. Expression of the transgene is monitored by analysis of phenotype or tissue-specific mRNA expression, in transgenic animals before, during, and after being challenged with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene which disrupts transcription and/or translation of the endogenous disease candidate gene in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Expression of the marker gene confers a selective advantage to the transformed cells when incubated with an otherwise toxic/lethal selecting agent. Transformed ES cells are selected, identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168:342–357; Wiles and Keller (1991) Development 111:259–267; and Klug et al. (1996) J. Clin. Invest. 98:216–224). Recent developments demonstrate that ES cells derived from human blastocysts may also be manipulated in vitro to differentiate into eight separate cell lineages, including eridoderm, mesoderm, and ectodermal cell types (Thomson et al. (1998) Science 282:1145–1147).

Knockout Analysis

In gene knockout analysis, a region of a human disease gene candidate is enzymatically modified to include a non-mammalian gene such as the neomycin phosphotransferase. gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc. Natl. Acad. Sci. 95:11371–11376; Baudoin et al. (1998) Genes Dev. 12:1202–1216; and Zhuang et al. (1998) Mol. Cell Biol. 18:3340–3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the nucleic acid molecules which encode the mammalian protein may be used in any molecular biology techniques that have yet to be developed, provided the new techniques rely on properties of nucleic acid molecules that are currently known, including, but not limited to, such properties as the triplet genetic code and specific base pair interactions.

EXAMPLES

It is understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to best describe the subject invention and its representative constituents.

I cDNA Library Construction

The RALINOT01 cDNA library was constructed from liver tissue removed from a pool of fifty 10- to 11-week-old Sprague-Dawley female rats (Pharmacon, Waverly Pa.). The animals were housed in standard laboratory caging and fed PMI-certified Rodent Diet #5002. The animals appeared to be in good health at the time tissue was harvested. The animals were anesthetized by $CO_2$ inhalation, and then cardiocentesis was performed.

Frozen tissue was homogenized and lysed in TRIZOL reagent (1 g tissue/10 ml TRIZOL; Life Technologies), a monophasic solution of phenol and guanidine isothiocyanate, using a POLYTRON homogenizer (PT-3000; Brinkmann Instruments, Westbury N.Y.). After a brief incubation on ice, chloroform (1:5 v/v) was mixed with the reagent, and then centrifuged at 1,000 rpm. The upper aqueous layer was removed to a fresh tube, and the RNA precipitated with isopropanol, resuspended in DEPC-treated water, and treated with DNase I for 25 min at 37° C. The RNA was re-extracted once with phenol-chloroform, pH 4.7, and precipitated using 0.3 M sodium acetate and 2.5 volumes ethanol. The mRNA was then isolated using an OLIGOTEX kit (QIAGEN, Chatsworth Calif.) and used to construct the cDNA library.

The mRNA was handled according to the recommended protocols in the SUPERSCRIPT plasmid system (Life Technologies). The cDNAs were fractionated on a SEPHAROSE CL-4B column (Amersham Pharmacia Biotech), and those cDNAs exceeding 400 bp were ligated into the pINCY1 plasmid vector (Incyte Pharmaceuticals). The plasmid pINCY1 was subsequently transformed into DH5α or DH10B competent cells (Life Technologies).

The RAKINOT01 library was constructed using mRNA isolated from kidney tissue removed from a pool of fifty, 7- to 8-week-old male Sprague-Dawley rats, as described above.

The RAKINOT02 library was constructed using mRNA isolated from kidney tissue removed from a pool of fifty, 10- to 11-week-old female Sprague-Dawley rats, as described above.

II CDNA Library Normalization

In some cases, cDNA libraries were normalized in a single round according to the procedure of Soares et al. (1994, Proc. Natl. Acad. Sci. 91:9228–9232) with the following modifications. The primer to template ratio in the primer extension reaction was increased from 2:1 to 10:1. Reduction of each dNTP concentration in the reaction to 150 μM allowed the generation of longer (400–1000 nucleotide (nt)) primer extension products. The reannealing hybridization was extended from 13 to 19 hours. The single stranded DNA circles of the normalized library were purified by hydroxyapatite chromatography, converted to partially double-stranded by random priming, and electroporated into DH10B competent bacteria (Life Technologies).

The Soares normalization procedure is designed to reduce the initial variation in individual cDNA frequencies and to achieve abundances within one order of magnitude while maintaining the overall sequence complexity of the library. In the normalization process, the prevalence of high-abundance cDNA clones decreases significantly, clones with mid-level abundance are relatively unaffected, and clones for rare transcripts are increased in abundance. In the modified Soares normalization procedure, significantly longer hybridization times are used to increase gene discovery rates by biasing the normalized libraries toward low-abundance cDNAs that are well represented in a standard transcript image.

The RALINON03, RALINON04, and RALINON07 normalized rat liver cDNA libraries were constructed with $2.0 \times 10^6$, $4.6 \times 10^5$, and $2.0 \times 10^6$ independent clones from the RALINOT01cDNA library, respectively. The RALINOT01 cDNA library was normalized in one round using conditions adapted from Soares (supra) except that a significantly longer (48-hour) reannealing hybridization was used.

III cDNA Library Prehybridization

The RALINOH01 cDNA library was constructed with clones from the RALINOT01 cDNA library. After preparation of the RALINOT01 cDNA library, 9,984 clones were spotted onto a nylon filter, lysed, and the plasmid DNA was bound to the filter. The filter was incubated with pre-warmed hybridization buffer and then hybridized at 42° C. for 14–16 hours in 0.75 M NaCl, 0.1 M $Na_2HPO_4/NaH_2PO_4$, 0.15 M tris-HCl (pH 7.5), 5×Denhardt's Solution, 2% SDS, 100 μg/ml sheared salmon sperm DNA, 50% formamide, and [$^{32}$P]-labeled oligonucleotide molecules made from reverse transcribed rat liver mRNA from an untreated animal. The filter was rinsed with 2×SSC (saline sodium citrate) at ambient temperature for 5 minutes followed by washing for 30 minutes at 68° C. with pre-warmed washing solution (2×SSC, 1% SDS). The wash was repeated with fresh washing solution for an additional 30 minutes at 68° C. Filters were then washed twice with pre-warmed washing solution (0.6×SSC, 1% SDS) for 30 minutes at 68° C. Some 4,224 clones had very low hybridization signals and about 20% of the clones had no signals and two groups were isolated and sequenced.

IV Isolation and Sequencing of cDNA Clones

DNA was isolated using the following protocol. Single bacterial colonies were transferred into individual wells of 384-well plates (Genetix Ltd, Christchurch, United Kingdom) using sterile toothpicks. The wells contained 1 ml of sterile Terrific Broth (Life Technologies) with 25 mg/l carbenicillin and 0.4% glycerol (v/v). The plates were covered and placed in an incubator (Thermodyne, Newtown Square Pa.) at 37° C. for 8–10 hours. Plasmid DNA was released from the cells and amplified using direct link PCR (Rao, V. B. (1994) Anal. Biochem. 216:1–14) as follows. The direct link PCR solution included 30 ml of NUCLEIX PLUS PCR nucleotide mix (Amersham Pharmacia Biotech, Piscataway N.J.) and 300 μl of Taq DNA polymerase (Amersham Pharmacia Biotech). Five microlitres of the PCR solution were added to each of the 384 wells using the MICROLAB 2200 system (Hamilton, Reno Nev.); plates were centrifuged at 1000 rpm for 20 seconds and refrigerated until use. A 384 pin tool (V&P Scientific Inc, San Diego Calif.) was used to transfer bacterial cells from the incubation plate into the plate containing the PCR solution where 0.1% Tween 20 caused the cells to undergo lysis and release the plasmid DNA. After lysis, the plates were centrifuged up to 500 rpm, covered with a cycle sealer, and cycled using a 384-well DNA ENGINE thermal cycler (MJ Research, Watertown Mass.) using the program dPCR30 with the following parameters: Step 1) 95° C., 1 minute; Step 2) 94° C., 30 seconds; Step 3) 55° C., 30 seconds; Step 4) 72° C., 2 minutes; Step 5) steps 2, 3, and 4 repeated 29 times; Step 6) 72° C., 10 minutes; and Step 7) storage at 4° C.

The concentration of DNA in each well was determined by dispensing 100 μl PICO GREEN quantitation reagent (0.25% (v/v), Molecular Probes, Eugene Oreg.) dissolved in 1×TE and 0.5 μl of undiluted PCR product into each well of an opaque fluorimeter plate (Corning Costar, Acton Mass.), allowing the DNA to bind to the quantitation reagent. The plate was scanned in a Fluoroscan II (Labsystems Oy, Helsinki, Finland) to measure the fluorescence of the sample and to quantitate the concentration of DNA. Typical concentrations of each DNA sample were in the range of 100 to 500 ng/ml.

The cDNAs were prepared for sequencing using either a HYDRA microdispenser (Robbins Scientific, Sunnyvale Calif.) or MICROLAB 2200 system (Hamilton) in combination with the DNA ENGINE thermal cyclers (MJ Research). The cDNAs were sequenced using the method of Sanger, F. and A. R. Coulson (J. Mol. Biol. (1975) 94:441–448) and the ABI 377 sequencing systems (PE Biosystems). Most of the isolates were sequenced according to standard ABI protocols using ABI kits (PE Biosystems). The solution volumes were used at 0.25×–1.0× concentrations. Typically, 500 to 700 base pairs were sequenced in 3.5 to 4 hours. In the alternative, cDNAs may have been sequenced using solutions and dyes from Amersham Pharmacia Biotech.

V Rat Liver and Kidney Gene Selection

As a first step, originator molecules from high throughput sequencing experiments were derived from clone inserts from RALINOT01, RAKINOT01, RAKINOT02, RALINOH01, RALINON03, RALINON04 and RALINON07. CDNA library clones were obtained. There were 18,140 rat liver molecules and 5,779 rat kidney molecules.

Additionally, 1,500 rat molecules derived from clone inserts of any of 113 rat cDNA libraries were selected based on their homology to genes coding for polypeptides implicated in toxicological responses including peroxisome-associated genes, lysosome-associated genes, apoptosis-associated genes, cytochrome P450 genes, detoxification genes such as sulfotransferases, glutathione S-transferases, and cysteine proteases, and the like.

Then, all the remaining molecules derived from all of the rat cDNA library clones were clustered based on the originator molecules described above. The clustering process involved identifying overlapping molecules that have a match quality indicated by a product score of 50 using BLAST. 6581 master clusters were identified.

After forming the clone clusters, a consensus sequence was generated based on the assembly of the clone molecules using PHRAP (Phil Green, University of Washington). The assembled molecules were then annotated by first screening the assembled molecules against GenBank using BLASTn and then by screening the assembled molecules against GenPept using FASTX. About two thirds of the assembled molecules were annotated, about one third of the assembled molecules were not annotated. For example, for nucleic acid sequence analysis, the program BLASTN 1.4.9MP-WashU was used with default parameters; ctxfactor=2.00; E=10; MatID, 0; Matrix name, +5,−4. In another example, for amino acid sequence analysis, the program NCBI-BLASTX 2.0.4 was used with default parameters; matrix, BLOSUM62; gap penalties, existence 11, extension 1; frameshift window, decay constant 50, 0.1.

VI Substrate and Array Element/Probe Preparation

Clones nominated in the process described in Example V were used to generate array elements. Each array element was amplified from bacterial cells. PCR amplification used primers complementary to the vector sequences flanking the cDNA insert. Array elements were amplified in thirty cycles of PCR from an initial quantity of 1–2 ng to a final quantity greater than 5 μg. Amplified array elements were then purified using SEPHACRYL-400 (Amersham Pharmacia Biotech).

Purified array elements were immobilized on polymer-coated glass slides. Glass microscope slides (Corning, Corning N.Y.) cleaned by ultrasound in 0.1% SDS and acetone, with extensive distilled water washes between and after treatments. Glass slides were etched in 4% hydrofluoric acid (VWR, West Chester Pa.), washed extensively in distilled water, and coated with 0.05% aminopropyl silane (Sigma-Aldrich, St. Louis Mo.) in 95% ethanol. Coated slides were cured in a 110° C. oven.

Array elements were applied to the coated glass substrate using a procedure described in U.S. Pat. No. 5,807,522 and incorporated herein by reference. In brief, 1 μl of the array element DNA, at an average concentration of 0.5 μg/ml in 3×SSC, was loaded into the open capillary printing element by a high-speed robotic apparatus. The apparatus then deposited about 5 nl of the array element sample per slide. A total of 7404 array elements representing rat liver and kidney genes and a variety of control elements, including 14 synthetic control molecules, human genomic DNA, and yeast genomic DNA, were arrayed in four identical quadrants within a 1.8 cm$^2$ area of the glass substrate.

Microarrays were UV-crosslinked using a STRATALINKER UV-crosslinker (Stratagene). Microarrays were washed at room temperature once in 0.2% SDS and three times in distilled water. Non-specific binding sites were blocked by incubation of microarrays in 0.2% casein in phosphate buffered saline (PBS; Tropix Inc., Bedford Mass.) for 30 minutes at 60° C. followed by washes in 0.2% SDS and distilled water as before.

VII Target Preparation

Male Sprague-Dawley rats (6–8 wk old) were dosed intraperitoneally with one of the following: clofibrate (CLO; Acros, Geel, Belgium) at 250 mg/kg body weight (bw); acetaminophen (APAP; Acros) at 1000 mg/kg bw; benzo(a)pyrene (B(a)P; Acros) at 10 mg/kg bw; or dimethylsulfoxide vehicle (DMSO; Acros) at less than 2 ml/kg bw, and the animals were later euthanized by $CO_2$ inhalation. Animals were monitored daily for physical condition and body weight. Three animals per group were sacrificed approximately 12 hours, 24 hours, 3d (d), 7d, 14d, and 28d following the single dose. Prior to sacrifice a blood sample from each animal was drawn and assayed for serum alanine transferase (ALT) and serum aspartate aminotransferase (AST) levels using a diagnostic kit (Sigrna-Aldrich). Observed gross pathology and liver weights were recorded at time of necropsy. Liver, kidney, brain, spleen and pancreas from each rat were harvested, flash frozen in liquid nitrogen, and stored at −80 ° C.

In the alternative, male Han-Wistar rats (8–9 wk old) were dosed by oral gavage with one of the following: fenofibrate (FEN; Sigma-Aldrich) at 250 mg/kg bw; carbon tetrachloride ($CCL_4$; Sigma-Aldrich) at 3160 mg/kg bw, hydrazine (HYDR; Sigma-Aldrich) at 120 mg/kg bw; α-naphthylisothiocyanate (ANIT; Sigma-Aldrich) at 200 mg/kg bw; 4-acetylaminofluorene (4-AFF; Lancaster Synthesis, Morecambe, Lancashire, UK) at 1000 mg/kg bw; corn oil vehicle, or sterile water vehicle, at 10 ml/kg bw. The animals were checked twice daily for clinical signs of distress. Blood was collected six days prior to the dose and at sacrifice. Three animals per group were sacrificed approximately six hours and 24 hours following the single dose. The animals were euthanized by exsanguination under isoflurane anaesthesia. Observed gross pathology and liver weights were recorded at time of necropsy. Livers from each rat were harvested, dissected into approximate 100 mg pieces, flash frozen in liquid nitrogen, and stored at −70° C.

For each target preparation, frozen liver was homogenized and lysed in TRIZOL reagent (Life Technologies, Gaithersburg Md.) following the modifications for liver RNA isolation. Messenger RNA was isolated using an OLIGOTEX kit (QIAGEN) and labeled with either Cy3- or Cy5-labeled primers (Operon Technologies, Alameda Calif.) using the GEMBRIGHT labeling kit (Incyte Pharmaceuticals). Messenger RNA isolated from tissues of rats treated with clofibrate, acetaminophen, or benzo(a)pyrene was labeled with Cy5 and mRNA isolated from tissues of rats treated with DMSO was labeled with Cy3. Quantitative and differential expression pattern control cDNAs were added to each labeling reaction. Labeled cDNA was treated with 0.5 M sodium bicarbonate. (pH 9.2) for 20 min at 85 ° C. to degrade the RNA and purified using two successive CHROMA SPIN 30 gel filtration spin columns (Clontech, Palo Alto Calif.). Cy3-labeled control sample and Cy5-labeled experimental sample were combined and precipitated in glycogen, sodium acetate, and ethanol.

Targets are also prepared from tissue needle biopsy samples. Samples are used to identify changes within the tissue following exposure to, for example, a toxic compound, a potential toxic compound, a compound with unknown metabolic responses, and a pharmacological compound.

VIII Hybridization

Hybridizations were carried out using the methods described by Shalon (supra).

IX Detection

The microscope used to detect the reporter-labeled hybridization complexes was equipped with an Innova 70 mixed gas 10 W laser (Coherent Lasers, Santa Clara Calif.) capable of generating spectral lines at 488 nm for excitation of Cy3, and 632 nm for excitation of Cy5. The excitation laser light was focused on the array using a 20×microscope objective (Nikon, Melville N.Y.). The slide containing the array was placed on a computer-controlled X-Y stage on the microscope and raster-scanned past the objective. The 1.8 cm×1.8 cm array used in the present example was scanned with a resolution of 20 micrometers.

In two separate scans, a mixed gas multiline laser excited the two fluorophores sequentially. Emitted light was split, based on wavelength, into two photomultiplier tube detectors (PMT R1477, Hamamatsu Photonics, San Jose Calif.) corresponding to the two fluorophores. Appropriate filters positioned between the array and the photomultiplier tubes were used to filter the signals. The emission maxima of the fluorophores used were 565 nm for Cy3 and 650 nm for Cy5. Each array was typically scanned twice, one scan per fluorophore using the appropriate filters at the laser source, although the apparatus was capable of recording the spectra from both fluorophores simultaneously.

The sensitivity of the scans was typically calibrated using the signal intensity generated by a cDNA control species added to the probe mix at a known concentration. A specific location on the array contained a complementary DNA sequence, allowing the intensity of the signal at that location to be correlated with a weight ratio of hybridizing species of 1:100,000. When two probes from different sources (e.g., representing test and control cells), each labeled with a different fluorophore, are hybridized to a single array for the purpose of identifying genes that are differentially expressed, the calibration was done by labeling samples of the calibrating cDNA with the two fluorophores and adding identical amounts of each to the hybridization mixture.

The output of the photomultiplier tube was digitized using a 12-bit RTI-835H analog-to-digital (A/D) conversion board (Analog Devices, Norwood Mass.) installed in an IBM-compatible PC computer.

The digitized data were displayed as an image where the signal intensity was mapped using a linear 20-color transformation to a pseudocolor scale ranging from blue (low signal) to red (high signal). The data was also analyzed quantitatively. Where two different fluorophores were excited and measured simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for signal analysis was the GEMTOOLS gene expression analysis program (Incyte Pharmaceuticals).

X Results

The expression patterns of eight cytochrome P450 isozymes known to be induced in a toxicological response were monitored during the 28 day time course. The results using clofibrate, acetaminophen, and benzo(a)pyrene are shown in Table 1, Table 2, and Table 3, respectively. Each of the known genes was upregulated or downregulated greater than 2-fold at least once during the time course.

TABLE 1

| Gene expression patterns (x-fold change) of known genes in clofibrate-treated rat liver | | | | | |
|---|---|---|---|---|---|
| Gene | 12 hours | 24 hours | 3 days | 7 days | 28 days |
| P450 LA-omega 4A3 | 14.8 | 26.6 | 1.1 | 0.5 | 0.47 |
| P450 4A | 7.0 | 16.6 | 1.4 | 0.5 | 1.3 |
| P450 3A2 | 0.14 | 1.2 | 0.63 | 0.50 | 0.45 |

TABLE 2

| Gene expression patterns (x-fold change) of known genes in acetaminophen-treated rat liver | | | | | | |
|---|---|---|---|---|---|---|
| Gene | 12 hours | 24 hours | 3 days | 7 days | 14 days | 28 days |
| P450 4A | 1.0 | 4.5 | 2.1 | 2.0 | 4.4 | 4.8 |
| P450f 2C7 | 0.21 | 0.43 | 0.47 | 0.5 | 1.2 | 1.3 |
| P450 14DM | 0.31 | 0.20 | 2.0 | 1.1 | 1.4 | 0.42 |

TABLE 3

| Gene expression patterns (x-fold change) of known genes in benzo(a)pyrene-treated rat liver | | | | | | |
|---|---|---|---|---|---|---|
| Gene | 12 hours | 24 hours | 3 days | 7 days | 14 days | 28 days |
| P450 LA-omega 4A3 | 1.2 | 2.3 | 2.4 | 1.4 | 6.8 | 1.2 |
| P450 MCA-inducible 1A2 | 7.3 | 9.2 | 5.7 | 2.5 | 2.5 | 0.5 |

In addition, results from two samples that had been treated identically were compared to determine the range of normal variation of gene expression patterns between the samples.

In one analysis, where two different samples were prepared from identically treated tissues, gene expression patterns of cDNAs which were upregulated or downregulated not more than 1.7-fold were within the 95% confidence limits of a Poisson normal distribution. In a separate analysis, gene expression patterns of cDNAs which were upregulated or downregulated more than 2-fold accounted for not more than 5% of the total hybridizable sample nucleic acid molecules in two identically-treated tissue samples.

We have discovered novel nucleotide molecules that are up-regulated or down-regulated at least 2-fold at least once during the time course. These molecules are SEQ ID NOs:1–16 provided in the Sequence Listing. These polynucleotide molecules can be used for screening compounds or therapeutics for a toxicologic effect and applications including detecting metabolic and toxicological responses, and in monitoring drug mechanism of action.

Table 4 shows the gene expression pattern of selected molecules that were upregulated at least 2-fold at least once during the time course following treatment with clofibrate (CLO). Table 5 shows the gene expression pattern of selected molecules that were downregulated at least 2-fold at least once during the time course following treatment with CLO.

TABLE 4

Gene expression patterns (x-fold change) of CLO-upregulated nucleic acid molecules

| SEQ ID NO: | 12 hours | 24 hours | 3 days | 7 days | 28 days |
|---|---|---|---|---|---|
| 2 | 2.6 | 1.4 | 0.5 | 1.1 | 1.2 |
| 3 | 1.3 | 2 | 1.3 | 1.5 | 1.5 |
| 4 | 2 | 0.36 | 0.47 | 0.26 | 0.30 |
| 5 | 1.7 | 2.9 | 1.6 | 1.5 | 1.2 |
| 8 | 2.6 | 1.7 | 1.3 | 1.3 | 1.4 |

TABLE 5

Gene expression patterns (x-fold change) of CLO-downregulated nucleic acid molecules

| SEQ ID NO: | 12 hours | 24 hours | 3 days | 7 days | 28 days |
|---|---|---|---|---|---|
| 1 | n.d. | 0.26 | 0.45 | 0.26 | 1.1 |
| 4 | 2.0 | 0.36 | 0.47 | 0.26 | 0.30 |
| 7 | 0.24 | 0.42 | 0.37 | 1.1 | 1.5 |

(n.d. = not detected)

Table 6 shows the gene expression pattern of selected molecules that were upregulated at least 2-fold at once during the time course following treatment with acetaminophen (APAP). Table 7 shows the gene expression pattern of selected molecules that were downregulated at least 2-fold at least once during the time course following treatment with APAP.

TABLE 6

Gene expression patterns (x-fold change) of APAP-upregulated nucleic acid molecules

| SEQ ID NO: | 12 hours | 24 hours | 3 days | 7 days | 14 days | 28 days |
|---|---|---|---|---|---|---|
| 2 | 1.3 | 2.2 | 1.1 | 0.5 | 1.2 | 1.3 |
| 3 | 1.2 | 2.1 | 0.47 | 0.46 | 1.8 | 1.5 |
| 4 | 3.3 | 0.47 | 0.47 | 0.23 | 0.35 | 0.36 |
| 5 | 1.1 | 2.1 | 1.1 | 1.2 | 1.3 | 1.4 |
| 6 | 1.8 | 5 | 2.5 | 1.1 | 1.4 | 1.3 |

TABLE 6-continued

Gene expression patterns (x-fold change) of APAP-upregulated nucleic acid molecules

| SEQ ID NO: | 12 hours | 24 hours | 3 days | 7 days | 14 days | 28 days |
|---|---|---|---|---|---|---|
| 8 | 1.1 | 2.5 | 1.1 | 1 | 1.7 | 1.4 |

TABLE 7

Gene expression patterns (x-fold change) of APAP-downregulated nucleic acid molecules

| SEQ ID NO: | 12 hours | 24 hours | 3 days | 7 days | 14 days | 28 days |
|---|---|---|---|---|---|---|
| 1 | 0.36 | 0.19 | 0.46 | 0.25 | 0.5 | 1.4 |
| 4 | 3.3 | 0.48 | 0.47 | 0.23 | 0.35 | 0.36 |
| 7 | 0.33 | 0.21 | 1.7 | n.d. | 1 | 0.39 |

(n.d. = not detected)

Table 8 shows the gene expression pattern of selected molecules that were upregulated at least 2-fold at least once during the time course following treatment with benzo(a)pryrene (B(a)P). Table 9 shows the gene expression pattern of selected molecules that were downregulated at least 2-fold at least once during the time course following treatment with B(a)P.

TABLE 8

Gene expression patterns (x-fold change) of B(a)P-upregulated nucleic acid molecules

| SEQ ID NO: | 12 hours | 1 day | 3 days | 7 days | 14 days | 28 days |
|---|---|---|---|---|---|---|
| 2 | 0.5 | 0.47 | 1.2 | 1.1 | 2.6 | 0.47 |
| 3 | 1.4 | 2.1 | 1.2 | 1.5 | 2.7 | 1.6 |
| 5 | 1.5 | 1.4 | 1.2 | 0.47 | 2 | 0.46 |
| 6 | 2.2 | 1.4 | 1.4 | 1.2 | 2.2 | n.d. |
| 7 | 1.2 | 2.2 | 1.4 | 0.5 | 0.42 | 1.1 |
| 8 | 1.6 | 1.7 | 1.3 | 1.3 | 2 | 1.1 |

(n.d. = not detected)

TABLE 9

Gene expression patterns (x-fold change) of B(a)P-downregulated nucleic acid molecules

| SEQ ID NO: | 12 hours | 1 day | 3 days | 7 days | 14 days | 28 |
|---|---|---|---|---|---|---|
| 1 | 0.37 | 0.39 | 0.35 | 1.4 | 0.33 | 1.5 |
| 4 | 0.5 | 0.26 | 0.31 | 0.36 | 0.47 | n.d. |

(n.d. = not detected)

TABLE 10

| | Library abundance (least abundant = 1) patterns of nucleic acid molecules | | | | | | | | |
|---|---|---|---|---|---|---|---|---|---|
| SEQ ID NO: | Untreated | CLO | FEN | APAP | BaP | CCl₄ | HYDR | ANIT | 4-AAF |
| 8 | 4 | 7 | 6 | 3 | 9 | 4 | 1 | 1 | 3 |
| 9 | 13 | 5 | 6 | 4 | 15 | 5 | 6 | 6 | 2 |
| 10 | n.d. | 1 | 8 | 3 | n.d. | n.d. | n.d. | 1 | n.d. |
| 11 | 5 | 2 | 4 | 8 | 20 | 7 | 10 | n.d. | 2 | n.d. = not detected

XI Identification and Analyses of Homologous Molecule in other Organisms

The rat sequences (SEQ ID NOs:1–16) were used to identify additional sequences in the ZOOSEQ and LIFESEQ databases (Incyte Pharmaceuticals) related to rat nucleic acid molecules regulated during toxicological response (SEQ ID NOs:18–47).

The first pass cDNAs, SEQ ID NOs:5, and 60 through 134, were assembled using PHRAP (Phil Green, supra), using the following default parameters, to produce the contiguous sequence SEQ ID NO:135. Mismatch penalty=−2; gap initiation penalty <0; gap extension penalty <0; minimum length of matching word=14; minimum SWAT score=30; bandwidth=14; use raw SW scores, "No"; index word size=10; maximum gap size =30; number of initial bases to be converted to 'N', 0; vector segment length=60; Mismatch penalty for scoring degenerate end sequence=−2; Min. score for converting degenerate end sequence to 'N', 20; Minimum size of confirming segment=8; Amount by which confirming segments are trimmed=1; Penalty for confirming matches=−5; Min. SWAT score for confirming matches=30; LLR cutoff for displaying discrepancies.=20; Minimum segment size=8; Spacing between nodes=4; Split/reassemble initial 'greedy' assembly, "No".

Translation of SEQ ID NO:135 using MACDNASIS PRO software (version 1.0, Hitachi Software Engineering) using default parameters of the program elucidated the putative protein coding region, SEQ ID NO:136. The nucleic acid and amino acid sequences were queried against databases such as the LIFESEQ (Incyte), GenBank, and SwissProt databases using BLAST. Motifs, HMM algorithms, and alignments with BLOCKS, PRINTS, Prosite, and PFAM databases were used to perform functional analyses; the antigenic index (Jameson-Wolf analysis) was determined using LASERGENE software (version 1.62d1, DNASTAR). BLAST2 analysis of SEQ ID NOs:135 and 136 using the human EST LIFESEQ database (Incyte) identified Incyte Clone Numbers 746355H1 (SEQ ID NO:137) and 1294663H1 (SEQ ID NO:138) which were assembled with their respective clustered clones to produce SEQ ID NOs:37 and 38 which encoded SEQ ID NOs:51 and 52, respectively.

Functional analysis of SEQ ID NO:136 using BLOCKS, PRINTS, Prosite, PFAM, Motifs, and HMM algorithms identified a potential protein kinase C phosphorylation site at residue S84 (Motifs); a potential signal peptide from residue M1 through residue A33 (SPScan); a potential transmembrane domain from residue P37 through residue L56 (HMM TM), a sodium/neurotransmitter symporter signature from residue G34 through A53, a sodium/alanine symporter signature from G34 through A53, and an asparaginase/glutaminase family signature from residue W64 through residue G75 (BOCKS and PRINTS).

Functional analysis of SEQ ID NO:51 using BLOCKS, PRINTS, Prosite, PFAM, Motifs, and HMM algorithms identified a potential protein kinase C phosphorylation site at residue S83 (Motifs); a potential signal peptide sequence from residue M1 through residue A52 (SPScan); a sodium/alanine symporter signature from residue G33 through residue A52, an asparaginase/glutaminase family signature from residue W63 through residue G74, and a channel-forming colicin domain from residue K31 through residue G49 (BLOCKS and PRINTS). Functional analysis of SEQ ID NO:52 using BLOCKS, PRINTS, Prosite, PFAM, Motifs, and HMM algorithms identified a potential signal peptide sequence from residue M1 through A53 (SPScan); a sodium/alanine symporter signature from residue G34 through residue A53, a 6-phosphogluconate dehydrogenase family signature from residue G15 through residue A40, an FAD-dependant glycerol-3-phosphate dehydrogenase family signature from residue Y18 through residue Y30, and a vacuolar ATP synthetase 16 kDa subunit signature from residue L39 through residue G65 (BLOCKS and PRINTS).

What is claimed is:

1. A method for detecting or diagnosing the effect of a toxic compound or molecule associated with increased or decreased levels of nucleic acid molecules in a mammalian subject comprising:

a) treating a mammalian subject with a toxic compound or molecule;

b) obtaining a sample containing nucleic acids from the mammalian subject treated with the toxic compound or molecule;

c) contacting the sample with a microarray comprising a plurality of nucleic acid molecules consisting of SEQ ID NOs:1–47 or fragments thereof under conditions for the formation of one or more hybridization complexes, wherein the fragments are polynucleotides consisting of the first sixty consecutive nucleotides of a polynucleotide selected from SEQ ID NOs:1–47; and d) detecting the hybridization complexes, wherein the presence, absence or change in amount of the hybridization complex, as compared with the hybridization complexes formed from nucleic acid molecules from an untreated mammalian subject, is indicative of a metabolic response to the toxic compound or molecule.

2. The method of claim 1 wherein:

a) the sample is a tissue chosen from liver, kidney, brain, spleen, pancreas, and lung;

b) the sample is liver tissue;

c) the toxic compound or molecule which elicits the metabolic response induces at least a 2-fold change in the amount of at least one of the nucleic acid molecules of the sample;

d) the toxic compound is a peroxisome proliferator;

e) the toxic compound is a hypolipidemic drug; and f) the toxic compound is clofibrate or one of its corresponding metabolites.

3. The method of claim 1 wherein:

a) the sample is a tissue chosen from liver, kidney, brain, spleen, pancreas, and lung;

b) the sample is liver tissue;

c) the toxic compound or molecule which elicits the metabolic response induces at least a 2-fold change in the amount of at least one of the nucleic acid molecules of the sample;

d) the toxic compound is acetominophen or one of its corresponding metabolites.

4. The method of claim 1 wherein:

a) the sample is a tissue chosen from liver, kidney, brain, spleen, pancreas, and lung;

b) the sample is liver tissue;

c) the toxic compound or molecule which elicits the metabolic response induces at least a 2-fold change in the amount of at least one of the nucleic acid molecules of the sample;

d) the toxic compound is a polycyclic aromatic hydrocarbon;

e) the toxic compound is a diol epoxide; and f) the toxic compound is benzo(a)pyrene, or one of its corresponding metabolites.

5. A method for detecting or diagnosing a toxicological response to a test compound or molecule in a mammalian subject, the method comprising:

a) treating a mammalian subject with a test compound or molecule;

b) obtaining a sample containing nucleic acids from the mammalian subject treated with the test compound or molecule;

c) contacting the sample with a microarray comprising a plurality of nucleic acid molecules of SEQ ID NOs:1–47, or a fragment thereof, under conditions for the formation of one or more hybridization complexes;

d) detecting the hybridization complexes, wherein the presence, absence or change in amount of the hybridization complex, as compared with the hybridization complexes formed from nucleic acid molecules from a normal or untreated mammalian subject, is indicative of a toxic response to the test compound or molecule.

6. The method of claim 5 wherein the test compound which elicits the metabolic response is a compound with a previously known metabolic response.

7. The method of claim 5 wherein the test compound which elicits the metabolic response is a compound with a previously unknown metabolic response.

* * * * *

SEQUENCE LISTING

```
<160> NUMBER OF SEQ ID NOS: 138

<210> SEQ ID NO 1
<211> LENGTH: 285
<212> TYPE: DNA
<213> ORGANISM: Rattus norvegicus
<220> FEATURE:
<221> NAME/KEY: misc_feature
<223> OTHER INFORMATION: Incyte ID No: 700305024H2
<220> FEATURE:
<221> NAME/KEY: unsure
<222> LOCATION: 68
<223> OTHER INFORMATION: a, t, c, g, or other
```

<400> SEQUENCE: 1

```
agagttctag cctcacttta agatgcttct ttctctcaga attaaaggac tcgttttact      60
aagcgtantt ccaaagcatg ttacttacat tccttcttgc tatccacaga cctggtaatt     120
aactctatca catggtttct actctctaat ggagaacagg agaaaaatga gtcccaagct     180
tcccaatcag aattttaaat cttgactttt tttcccaaat catttaactg gagatgaaca     240
gaccaaggca ggaaaaagaa acaaggttc tagagatcat ttgac                      285
```

<210> SEQ ID NO 2
<211> LENGTH: 291
<212> TYPE: DNA
<213> ORGANISM: Rattus norvegicus
<220> FEATURE:
<221> NAME/KEY: misc_feature
<223> OTHER INFORMATION: Incyte ID No: 700306220H1

<400> SEQUENCE: 2

```
ggctgcggtg ccttcggtcg cgcgtacacg ttgcatctcc tagcttcctc ctgaaccccg      60
ttttacgttc gcggcgggga aaacagcctg acgagtagac tgcagctcct gggagatggc     120
ggcgctgtgc cttacggtga acgccggaaa ccctccactg gaagctctgc tggcagtgga     180
gcatgtgaaa ggtgatgtca gcatttctgt ggaagaaggg aaggagaatc ttcttcgggt     240
ttctgagagt gtggtgttca ctgacacaaa ttcaatcctg cgctacttgg c              291
```

<210> SEQ ID NO 3
<211> LENGTH: 293
<212> TYPE: DNA
<213> ORGANISM: Rattus norvegicus
<220> FEATURE:
<221> NAME/KEY: misc_feature
<223> OTHER INFORMATION: Incyte ID No: 700510669H1
<220> FEATURE:
<221> NAME/KEY: unsure
<222> LOCATION: 51, 56-57, 179
<223> OTHER INFORMATION: a, t, c, g, or other

<400> SEQUENCE: 3

```
aggacctgtc cttacatatt gtggcctgaa gggacaaaat atgaggagtt naatannagg      60
acaattccac tgtttatttt ccttggtgct aaattaaaga atcaagccct tgttcgagcc     120
tttgaaattt tggcctactt tatttcagac actcaaaata caaatgccaa caaatggtnc     180
tgatatattt gagagtggga aggaatctct gatgtttaaa tttcactgtt gatctttcaa     240
aatggactag gcttaggatt acaatgaacc ttttgtcctt tgtcagtgtt tcg            293
```

<210> SEQ ID NO 4
<211> LENGTH: 260
<212> TYPE: DNA
<213> ORGANISM: Rattus norvegicus
<220> FEATURE:
<221> NAME/KEY: misc_feature
<223> OTHER INFORMATION: Incyte ID No: 700525676H1
<220> FEATURE:
<221> NAME/KEY: unsure
<222> LOCATION: 22, 75, 229
<223> OTHER INFORMATION: a, t, c, g, or other

<400> SEQUENCE: 4

```
gcagctcgga ctagtcagag gnctctggcg agggtggcat cgggatgccg tccgaagtca      60
cccacagtga cggangcccg ggtgcgaggg tctgcgcgca acgtcaggta cttagctccc     120
tgtggtatac tgatgaacag aaccctgca ccgtgggcct cagttttgcc taaagagatc      180
tgtgcaagaa ccttcttcag aatcactaca ccattagtaa ataagcgana ggagtattca     240
gagaggagaa ttatagggta                                                 260
```

<210> SEQ ID NO 5
<211> LENGTH: 290
<212> TYPE: DNA
<213> ORGANISM: Rattus norvegicus
<220> FEATURE:
<221> NAME/KEY: misc_feature
<223> OTHER INFORMATION: Incyte ID No: 700535332H1
<220> FEATURE:
<221> NAME/KEY: unsure
<222> LOCATION: 179
<223> OTHER INFORMATION: a, t, c, g, or other

<400> SEQUENCE: 5

```
aagggccagt tgcatccgca cccagtgctt gtaccttgaa ctcatttctt cctgactgct        60
agaggcctgt gtgttcttaa ctgctccgac ctctcctcca caggtgcagg cctggtgtgg       120
tctccaaagt gactgaacaa tgcagaagga cagtggccca ctggttcctt tacattatna       180
tggtttcggc tatgcggccc tggtggctac tggtgggatt attggctatg caaaagcagg       240
tatgtgccgt ccctggctgc tggatcttct ttgggggcct ggcaggctgg                  290
```

<210> SEQ ID NO 6
<211> LENGTH: 287
<212> TYPE: DNA
<213> ORGANISM: Rattus norvegicus
<220> FEATURE:
<221> NAME/KEY: misc_feature
<223> OTHER INFORMATION: Incyte ID No: 700536004H1

<400> SEQUENCE: 6

```
attatgtaaa taatgagcaa gatcaaatta acaaagacta gttacccagc attccgcatc        60
tagtcagttt tgtcatgggg cagttcaagc tgccacctga aacatcact aggctctcag        120 ggttcttggc accactcacc caagttacat ccaccagatt attttcagtc ttcacaagta       180
tcaccatgca tagtgggatt ttcagccatg aataaagggc gtgcgttttg ccatatcagt       240
ctctaaaata acctttgcta atcaatgcag tgagttgcta aggttta                     287
```

<210> SEQ ID NO 7
<211> LENGTH: 264
<212> TYPE: DNA
<213> ORGANISM: Rattus norvegicus
<220> FEATURE:
<221> NAME/KEY: misc_feature
<223> OTHER INFORMATION: Incyte ID No: 700640924H1
<220> FEATURE:
<221> NAME/KEY: unsure
<222> LOCATION: 239-240
<223> OTHER INFORMATION: a, t, c, g, or other -continued

```
<400> SEQUENCE: 7
gtgatgaaat gaggtatctc aaatccactg acagataaga aaacagggtt agagggaaag        60
tcacctctgt cacgtagagg cagaatatat gaacttaact ctagtttcca tgtctgtctt       120
tattaccttc atctttctac ttcctggcca caggcatttc acttaattga gcctaatgtc       180
agtatctgtg tgtgtcaatg tcgttaccac attctgatga agctaaaaaa taaaatttnn       240
tttgggccaa aaaaaaaaa aagg                                                264

<210> SEQ ID NO 8
<211> LENGTH: 238
<212> TYPE: DNA
<213> ORGANISM: Rattus norvegicus
<220> FEATURE:
<221> NAME/KEY: misc_feature
<223> OTHER INFORMATION: Incyte ID No: 700775760H1
<220> FEATURE:
<221> NAME/KEY: unsure
<222> LOCATION: 3, 26, 50, 53, 74, 100, 168, 228
<223> OTHER INFORMATION: a, t, c, g, or other

<400> SEQUENCE: 8
ganaccgaca ttttaatggt tcttangagg accaccacta gagtcaaggn ganaatggga        60
tgacgcgtgt tgcngtcctg ctgattctga caagagctgn tcactatgac agacagatgg      120
actgaatgga ctagaattat gtgaatctgt attatttaca gttggtancc aagagcatcg      180
atactcttta gagaggcagg ttaaataaag gattaagtat ttaggatntg aaatttat        238

<210> SEQ ID NO 9
<211> LENGTH: 112
<212> TYPE: DNA
<213> ORGANISM: Rattus norvegicus
<220> FEATURE:
<221> NAME/KEY: misc_feature
<223> OTHER INFORMATION: Incyte ID No: 700132084H1
<220> FEATURE:
<221> NAME/KEY: unsure
<222> LOCATION: 94-96, 101, 104-105, 109-110
<223> OTHER INFORMATION: a, t, c, g, or other

<400> SEQUENCE: 9
ctatgcccaa ggaaaaggct ccagaacaca ttcccttct cttcattgcc ttcccatcaa         60
gcaaggatcc aacctgggag gaccgattcc cagnnncggg ncannaagnn gg               112

<210> SEQ ID NO 10
<211> LENGTH: 238
<212> TYPE: DNA
<213> ORGANISM: Rattus norvegicus
<220> FEATURE:
<221> NAME/KEY: misc_feature
<223> OTHER INFORMATION: Incyte ID No: 700176719H1

<400> SEQUENCE: 10
tcttggtccc ttcacctgac ctccggtgct ccaacgggcg gcagaatgga agaaggtgag        60
gacccaggaa gtctgattaa agtgatccac ttgctggtct tgtctggtgt ctggggcatg      120
cagatgtggg tgacctttgc ctcaggcttc ctgcttttcc ggagcctccc gaggcacacg      180
tttggacttg tgcagagcaa gctcttccca gtctattttc acgtctcctt gggttgtg        238

<210> SEQ ID NO 11
<211> LENGTH: 247
<212> TYPE: DNA
<213> ORGANISM: Rattus norvegicus
```

```
<220> FEATURE:
<221> NAME/KEY: misc_feature
<223> OTHER INFORMATION: Incyte ID No: 701195696H1

<400> SEQUENCE: 11
ggatctttct gggcgagcaa cccgcaaaac gttgtgcatt gcgttgaaaa ggtgcatctg      60
gttcccgatt ctactcccca cccgcgaccg cacacagcaa acatgaccca gcagccgcct    120
gacgttgagg aggatgactg tctttctgaa taccaccacc tcttctgccc ggaccttctc    180
caggacaaag tggcttttat cactggtggt ggttctggga ttggcttccg gatcgccgag    240
attttca                                                              247

<210> SEQ ID NO 12
<211> LENGTH: 256
<212> TYPE: DNA
<213> ORGANISM: Rattus norvegicus
<220> FEATURE:
<221> NAME/KEY: misc_feature
<223> OTHER INFORMATION: Incyte ID No: 700483259H1
<220> FEATURE:
<221> NAME/KEY: unsure
<222> LOCATION: 70
<223> OTHER INFORMATION: a, t, c, g, or other

<400> SEQUENCE: 12
gtgacgtaca tggaaaacaa agcctacggg gacaggctca agccgcagac agcagcaagt     60
aaagcgcctn cggccctgaa gcatggcagc tatcccttcc agcggctcgc tcgtggctac    120
ccatgactac tatcggcgta agtagcccct cgccagcccc gcccagggct ggcccagggc    180
tctgtggctg acccgcctcc ccttcccagg acgtctgggc tcctcgtcca gcaacagctc    240
cggcggaagt gcagag                                                    256

<210> SEQ ID NO 13
<211> LENGTH: 285
<212> TYPE: DNA
<213> ORGANISM: Rattus norvegicus
<220> FEATURE:
<221> NAME/KEY: misc_feature
<223> OTHER INFORMATION: Incyte ID No: 700607235H1

<400> SEQUENCE: 13
ctgaagaccc accatgtctc tgctgactac tgtactactt ctctggggtt tcattctggg     60
cccagcaact gacacagcct gtatattcaa ggaagcctcg gaaaacagtc ccttgcccag    120
gccctggctt tctgccaatc cagtgccctg gatcacacct ggcctgagga cattcctgct    180
gtgccagggg acagtgcggg atgtagtctt catgctgagg cggaaggag atgatggttt     240 cctggcgata gtccaacaga tgttttctg agggagctg gaccc                      285

<210> SEQ ID NO 14
<211> LENGTH: 293
<212> TYPE: DNA
<213> ORGANISM: Rattus norvegicus
<220> FEATURE:
<221> NAME/KEY: misc_feature
<223> OTHER INFORMATION: Incyte ID No: 700609074H1
<220> FEATURE:
<221> NAME/KEY: unsure
<222> LOCATION: 16, 179
<223> OTHER INFORMATION: a, t, c, g, or other

<400> SEQUENCE: 14
ggcgtggagt tggagnagag cgtcaggcgc ctccgggaga agtttcatgg aaaagtgtcc     60
```

| | |
|---|---|
| cccaagaagg cagggctct tatgaggaag tttggcagcg accacactgg agttgggcgc | 120 |
| tctatcgtgt acgggctcaa gcagaaagat ggacaggagc tgagcaacga tttggacgnc | 180 |
| caggacccac cagaggacat gaagcaggac caagatatcc aggcagtagc cacctctctg | 240 |
| ttgcccctga cgcaagccaa tcttcgaatg ttccaaagag cccaagatga cct | 293 |

<210> SEQ ID NO 15
<211> LENGTH: 268
<212> TYPE: DNA
<213> ORGANISM: Rattus norvegicus
<220> FEATURE:
<221> NAME/KEY: misc_feature
<223> OTHER INFORMATION: Incyte ID No: 700627890H1
<220> FEATURE:
<221> NAME/KEY: unsure
<222> LOCATION: 7, 11, 40, 53, 150
<223> OTHER INFORMATION: a, t, c, g, or other

<400> SEQUENCE: 15

| | |
|---|---|
| gtacaangag ngccggggct tgggtctagt tggaggggan gcagtggcca gtncagggct | 60 |
| cagatgagag agttagccga gttaggggca gctactagga tgggggcagg aggagaagcg | 120 |
| gggctaacta taaagaagac tagatttcgn cacagtgggt atgtggaagg cagcttttcaa | 180 |
| accgcccttg tcaaacaaca cagggccagc agccttcaag accaggctat ccctgccgtc | 240 |
| tgctggcatg ggggcacttg taccgtcc | 268 |

<210> SEQ ID NO 16
<211> LENGTH: 265
<212> TYPE: DNA
<213> ORGANISM: Rattus norvegicus
<220> FEATURE:
<221> NAME/KEY: misc_feature
<223> OTHER INFORMATION: Incyte ID No: 700629293H1
<220> FEATURE:
<221> NAME/KEY: unsure
<222> LOCATION: 62, 264
<223> OTHER INFORMATION: a, t, c, g, or other

<400> SEQUENCE: 16

| | |
|---|---|
| atgacctta acttttctaa aaatgtgaag ttttgtactt atatatatca gctaaagtat | 60 |
| tntagcattc tttagtgtac ttagtttgat gccactttta gtgtttttgt tgcttttgtc | 120 |
| tgatttttat gaatgttcat tttaagactc cttgttgaaa tgggacagtt tcgttctttg | 180 |
| ataagcccga gaagaggatt cccttgggtg ttgacctcct ctgcatgatg tgcccaagca | 240 |
| tctgaactgc aaccaaggcc tttnc | 265 |

<210> SEQ ID NO 17
<211> LENGTH: 267
<212> TYPE: DNA
<213> ORGANISM: Mus musculus
<220> FEATURE:
<221> NAME/KEY: misc_feature
<223> OTHER INFORMATION: Incyte ID No: 701322438H1
<220> FEATURE:
<221> NAME/KEY: unsure
<222> LOCATION: 29, 200, 224
<223> OTHER INFORMATION: a, t, c, g, or other

<400> SEQUENCE: 17

| | |
|---|---|
| acctgccctt acatattgtg gcctgaagng acaaatatg agaagttcaa tgaaaagata | 60 |
| attccccctt tcaggaaaga tgttctctta ttttacttgg cgctaaatca aagaatcaag | 120 |
| cctttgttca agcctttgca attttggcct attttatttc agagagcaaa tggatggtat | 180 |

```
atatttggga gtgggaaggn tctttgattt ttaaatttca ctgntgagct ttcaaataga      240
ctaggcctta ggattacaat gaacaac                                         267

<210> SEQ ID NO 18
<211> LENGTH: 239
<212> TYPE: DNA
<213> ORGANISM: Mus musculus
<220> FEATURE:
<221> NAME/KEY: misc_feature
<223> OTHER INFORMATION: Incyte ID No: 701082352H2
<220> FEATURE:
<221> NAME/KEY: unsure
<222> LOCATION: 120
<223> OTHER INFORMATION: a, t, c, g, or other

<400> SEQUENCE: 18
atttcttagt ggggcaagga cctgcccttta catattgtgg cctgaaggga caaaatatga     60
gaagttcaat gaaaagataa ttccccctttt caggaaagat gttctcttat tttacttggn   120
gctaaatcaa agaatccagc cctttgttca agcctttgca attttggcct attttatttc    180
agagagcaaa tggttgttat atatttggga gtgggaagga atcttgattt ttaaatttc     239

<210> SEQ ID NO 19
<211> LENGTH: 244
<212> TYPE: DNA
<213> ORGANISM: Mus musculus
<220> FEATURE:
<221> NAME/KEY: misc_feature
<223> OTHER INFORMATION: Incyte ID No: 701423834H1
<220> FEATURE:
<221> NAME/KEY: unsure
<222> LOCATION: 149, 191, 242
<223> OTHER INFORMATION: a, t, c, g, or other

<400> SEQUENCE: 19
gtctcctgag tgcttaaatt acaggtgtgt accactaaac caaccctaag aatccatttt     60
aaaatgtcag tcactttaga tttcttagtg gggcaaggac ctgcccttac atattgtggc   120
ctgaagggac aaaatatgag aagttcaang aaaagataat tccccctttc aggaaagatg   180
ttctcttatt ntacttggtg ctaaatcaaa gaatcaagcc tttgttcaag cctttgcaat   240 tntg                                                                 244

<210> SEQ ID NO 20
<211> LENGTH: 240
<212> TYPE: DNA
<213> ORGANISM: Mus musculus
<220> FEATURE:
<221> NAME/KEY: misc_feature
<223> OTHER INFORMATION: Incyte ID No: 701423842H1
<220> FEATURE:
<221> NAME/KEY: unsure
<222> LOCATION: 79, 89, 151, 153, 156, 158, 160, 199, 225
<223> OTHER INFORMATION: a, t, c, g, or other

<400> SEQUENCE: 20
gtctcctgag tgcttaaatt acaggtgtgt accactaaac caaccctaag aatccatttt     60
aaaatgtcag tcactttana tttcttagng gggcaaggac ctgcccttac atattggggc   120
ctgaagggac aaaatatgag aagttcaatg nanagntnan tccccctttc aggaaagatg   180
gtctcttatt ttacttggng ctaaatcaaa gaatcaagcc tttgntcaag cctttgcaat   240

<210> SEQ ID NO 21
<211> LENGTH: 224
<212> TYPE: DNA
```

<213> ORGANISM: Mus musculus
<220> FEATURE:
<221> NAME/KEY: misc_feature
<223> OTHER INFORMATION: Incyte ID No: 701090430H1
<220> FEATURE:
<221> NAME/KEY: unsure
<222> LOCATION: 203
<223> OTHER INFORMATION: a, t, c, g, or other

<400> SEQUENCE: 21

```
ggcagctcgg accagtcaga gggccctggc gagggtggca tcgggtgcc atccgaagtc      60
gaccaccgtg acggaagccc cggcgcgggg gtctgcgcgc gacgtcagac acttagctgc   120
ctgtggtgta ctgataaaca gaacccttcc accgtgtgct gcagttttgc ctaaagagat   180
ctgtgcgaga actttcttca gantctctgc gccactagta aata                    224
```

<210> SEQ ID NO 22
<211> LENGTH: 249
<212> TYPE: DNA
<213> ORGANISM: Mus musculus
<220> FEATURE:
<221> NAME/KEY: misc_feature
<223> OTHER INFORMATION: Incyte ID No: 700966369H1
<220> FEATURE:
<221> NAME/KEY: unsure
<222> LOCATION: 12, 26, 34, 47, 70, 78, 234
<223> OTHER INFORMATION: a, t, c, g, or other

<400> SEQUENCE: 22

```
gcttttatgt ancccaatca gagcancgac cagnaaaatt gcaagtnttg agaggcacac      60
agcagaagan ctgcagantt ctgcttgatt ggcatctatc gttcctcctg agcagcaacc   120
cacagtagat aggaaaaagg tgtttgacag gcctggctaa gctcttgcgg agccactggc   180
atcagatggc gaagggactt gctgccaggt tgctgtctgt tggacagaag ctcngatgag   240
gtgtgctgg                                                          249
```

<210> SEQ ID NO 23
<211> LENGTH: 260
<212> TYPE: DNA
<213> ORGANISM: Mus musculus
<220> FEATURE:
<221> NAME/KEY: misc_feature
<223> OTHER INFORMATION: Incyte ID No: 700828522H1

<400> SEQUENCE: 23

```
caggcctggt gtggtctcca aagcgactga acaatgcaga aagacagtgg cccattgatg      60
cctttacatt attttggttt cggctatgca gccctggttg ctaccggtgg gattattggc   120
tatgccaaag caggtagtgt gccgtccctg gctgctgac tcttcttcgg gggcctggca   180
ggcctggggg cctaccagct gtctcaggat cccaggaatg tgtgggtttt cctagctaca   240
tctgggacct tggccggaat                                              260
```

<210> SEQ ID NO 24
<211> LENGTH: 246
<212> TYPE: DNA
<213> ORGANISM: Mus musculus
<220> FEATURE:
<221> NAME/KEY: misc_feature
<223> OTHER INFORMATION: Incyte ID No: 701250723H1

<400> SEQUENCE: 24

```
ctcggcttct cgctgtctgc tcgcgccctc gtcctacagc acaggcctcc cggctccggc      60
tccggctcca gtgttggttg ggtgcaggcc tggtgtggtc tccaaagcga ctgaacaatg   120
```

```
cagaaagaca gtggcccatt gatgccttta cattattttg gtttcggcta tgcagccctg    180
gttgctaccg gtgggattat tggctatgcc aaagcaggta gtgtgccgtc cctggctgct    240
ggactc                                                                246
```

```
<210> SEQ ID NO 25
<211> LENGTH: 252
<212> TYPE: DNA
<213> ORGANISM: Mus musculus
<220> FEATURE:
<221> NAME/KEY: misc_feature
<223> OTHER INFORMATION: Incyte ID No: 701254093H1

<400> SEQUENCE: 25
acctcggctt ctcgctgtct gctcgcgccc tcgtcctaca gcacaggcct cccggctccg     60
gcttccggct ccagtgttgg ttgggatgcc tttacattat tttggtttcg gctatgcagc    120
cctggttgct accggtggga ttattggcta tgccaaagca ggtagtgtgc cgtccctggc    180
tgctggactc ttcttcgggg gcctggcagg cctgggggct accagctgtc tcaggatccc    240
aggaatgtgt gg                                                         252
```

```
<210> SEQ ID NO 26
<211> LENGTH: 237
<212> TYPE: DNA
<213> ORGANISM: Mus musculus
<220> FEATURE:
<221> NAME/KEY: misc_feature
<223> OTHER INFORMATION: Incyte ID No: 701423901H1
<220> FEATURE:
<221> NAME/KEY: unsure
<222> LOCATION: 224, 232
<223> OTHER INFORMATION: a, t, c, g, or other

<400> SEQUENCE: 26
attttggttt cggctatgca gccctggttg ctaccggtgg gattattggc tatgccaaag     60
caggtagtgt gccgccctgg ctgctggact cttcttcggg ggcctggcag gcctgggggcc    120 taccagctgt ctcaggatcc caggaatgtg tgggttttcc tagctacatc tgggaccttg    180
ccggaattat ggggatgaga ttctacaact cggggaaatt tatnctgcag gntaatc        237
```

```
<210> SEQ ID NO 27
<211> LENGTH: 274
<212> TYPE: DNA
<213> ORGANISM: Mus musculus
<220> FEATURE:
<221> NAME/KEY: misc_feature
<223> OTHER INFORMATION: Incyte ID No: 701251161H1

<400> SEQUENCE: 27
ggtgtttcgt gggttatctt tgcaaatggg ctccgcggcc tagcgccctg gtggcctaaa     60
aacgaagcct gcaaggaagg ggttctccgc cgagcgcctc ggtcctgaag catggcagcc    120
atcccttcca gcggctcgct cgtggctacc catgactact atcggcgtaa gtagcccctc    180
gccagccccg cccagggctg gcccagggcc ctgtggctga cccgcctccc cttcccagga    240
cgcctgggct cctcgtccag cagcagctcc ggcg                                 274
```

```
<210> SEQ ID NO 28
<211> LENGTH: 141
<212> TYPE: DNA
<213> ORGANISM: Mus musculus
<220> FEATURE:
<221> NAME/KEY: misc_feature
```

```
<223> OTHER INFORMATION: Incyte ID No: 701085115H2
<220> FEATURE:
<221> NAME/KEY: unsure
<222> LOCATION: 15, 49, 67, 94, 105
<223> OTHER INFORMATION: a, t, c, g, or other

<400> SEQUENCE: 28
aaagtgtccc ccaanaaggc aggggctctt atgaggaagt ttggcagcna ccacaccgga      60
gttgggngct ctatcgtgta tggtgtcaag cagnaagacg gacangagct gatgcaacga    120
cctggacgct caggacccac c                                              141

<210> SEQ ID NO 29
<211> LENGTH: 274
<212> TYPE: DNA
<213> ORGANISM: Mus musculus
<220> FEATURE:
<221> NAME/KEY: misc_feature
<223> OTHER INFORMATION: Incyte ID No: 701387375H1
<220> FEATURE:
<221> NAME/KEY: unsure
<222> LOCATION: 103, 131, 203-204, 232, 239, 250, 256, 262
<223> OTHER INFORMATION: a, t, c, g, or other

<400> SEQUENCE: 29
ggagggctcg ctcttggggc tagtggtggg gaggcagtgg ccagttcagg gctcagatga      60
gagaggtggc agaattagag gcagccacta ggatgggggt gcnaggagaa gcggggctaa    120
gtataaagga nactagattt tgggacagtg gacgtgtgga aggcagcttc caaagcgcct    180
ttaacaatcc acaaagaacc agnngctttc aagaccaggc tatccctgct gnctgctgna    240
cttggacgtn caggangcac angtttcaca ggcg                                274

<210> SEQ ID NO 30
<211> LENGTH: 257
<212> TYPE: DNA
<213> ORGANISM: Mus musculus
<220> FEATURE:
<221> NAME/KEY: misc_feature
<223> OTHER INFORMATION: Incyte ID No: 701389479H1
<220> FEATURE:
<221> NAME/KEY: unsure
<222> LOCATION: 43, 52, 63, 134, 165, 168, 192, 216, 251, 253
<223> OTHER INFORMATION: a, t, c, g, or other

<400> SEQUENCE: 30
agggctcgct cttggggcta gtggtgggga ggcagtggcc agtcagggc tnagatgaga       60 gangtggcag aattagaggc agccactagg atgggggtgc gaggagaagc ggggctaagt    120
ataaaggaga ctanattttg ggacagtgga cgtgtggaag gcagnttnca aagcgccttt    180
aacaatccac anagaaccag cagctttcaa gaccangcta tccctgctgc tgctgcactt    240
gacgtcagga ngnacaa                                                   257

<210> SEQ ID NO 31
<211> LENGTH: 246
<212> TYPE: DNA
<213> ORGANISM: Mus musculus
<220> FEATURE:
<221> NAME/KEY: misc_feature
<223> OTHER INFORMATION: Incyte ID No: 701389530H1
<220> FEATURE:
<221> NAME/KEY: unsure
<222> LOCATION: 33, 41, 64, 75, 222
<223> OTHER INFORMATION: a, t, c, g, or other

<400> SEQUENCE: 31
```

-continued

```
caaggagggc tcgctcttgg ggctagtggt ggngaggcag nggccagttc agggctcaga      60
tganagaggc ggcanaatta gaggcagcca ctaggatggg ggtgccgagg agaagcgggg     120
ctaagtataa aggagactag attttgggac agtggacgtg tggaaggcag cttccaaagc    180
gcctttaaca atccacaaag aaccagcagc tttcaagacc angctatccc tgctgctgct    240
gcactt                                                                246
```

```
<210> SEQ ID NO 32
<211> LENGTH: 258
<212> TYPE: DNA
<213> ORGANISM: Mus musculus
<220> FEATURE:
<221> NAME/KEY: misc_feature
<223> OTHER INFORMATION: Incyte ID No: 701388372H1
<220> FEATURE:
<221> NAME/KEY: unsure
<222> LOCATION: 17, 25, 58, 102, 115, 158, 195, 204
<223> OTHER INFORMATION: a, t, c, g, or other

<400> SEQUENCE: 32
```

```
gagggctcgc tcttggnggc taagnggtgg ggagtcagtg ccacgttca gggctcanat      60 gagagaggtg gcagaattag aggcagccac taggatgggg gngccaggag aagcnggcta    120
agtataaagg agactagatt ttgggacagt ggacgtgngg aaggcagctt ccaaagcgcc    180
tttaacaatc cacanagaac cagnagcttt caaagaccag gctatccctc tgctgctggc    240
acttgacgtc cagaaggc                                                  258
```

```
<210> SEQ ID NO 33
<211> LENGTH: 257
<212> TYPE: DNA
<213> ORGANISM: Mus musculus
<220> FEATURE:
<221> NAME/KEY: misc_feature
<223> OTHER INFORMATION: Incyte ID No: 701270715H1
<220> FEATURE:
<221> NAME/KEY: unsure
<222> LOCATION: 248
<223> OTHER INFORMATION: a, t, c, g, or other

<400> SEQUENCE: 33
```

```
gttttctcat gaattgtttt tgcattgttg ataaagctag tatacccttt ggccttagcc     60
tataaatttt aaatatataa acaaaatatt aaagatgtag ttaattttaa atgaccttta    120
acttttctaa aaatgtgaag ttttgtactt acatatcatc taaagtatta tagcatttttt   180 aagtgtactt agtttgatgc cacttttagt gttttgttgc ttttgtctga ttttttgtaa    240
tgttcatnta agactcc                                                   257
```

```
<210> SEQ ID NO 34
<211> LENGTH: 4850
<212> TYPE: DNA
<213> ORGANISM: Homo sapiens
<220> FEATURE:
<221> NAME/KEY: misc_feature
<223> OTHER INFORMATION: Incyte ID No: 2302721CB1

<400> SEQUENCE: 34
```

```
cgcacacgtt gcatcttctt cctttcgcgg ggtcctccgt agttctggca cgagccaggc     60
gtactgacag gtggaccagc ggactggtgg agatggcgac gctctctctg accgtgaatt    120
caggagaccc tccgctagga gctttgctgg cagtagaaca cgtgaaagac gatgtcagca    180
tttccgttga agaagggaaa gagaatattc ttcatgtttc tgaaaatgtg atattcacag    240
```

```
atgtgaattc tatacttcgc tacttggcta gagttgcaac tacagctggg ttatatggct     300
ctaatctgat ggaacatact gagattgatc actggttgga gttcagtgct acaaaattat     360
cttcatgtga ttcctttact tctacaatta atgaactcaa tcattgcctg tctctgagaa     420
catacttagt tggaaactcc ttgagtttag cagatttatg tgtttgggcc accctaaaag     480
gaaatgctgc ctggcaagaa cagttgaaac agaagaaagc tccagttcat gtaaaacgtt     540
ggtttggctt tcttgaagcc cagcaggcct tccagtcagt aggtaccaag tgggatgttt     600
caacaaccaa agctcgagtg gcacctgaga aaaagcaaga tgttgggaaa tttgttgagc     660
ttccaggtgc ggagatggga aaggttaccg tcagatttcc tccagaggcc agtggttact     720
tacacattgg gcatgcaaaa gctgctcttc tgaaccagca ctaccaggtt aactttaaag     780
ggaaactgat catgagattt gatgacacaa atcctgaaaa agaaaaggaa gattttgaga     840
aggttatctt ggaagatgtt gcaatgttgc atatcaaacc agatcaattt acttatactt     900
cggatcattt tgaaactata atgaagtatg cagagaagct aattcaagaa gggaaggctt     960
atgtggatga tactcctgct gaacagatga agcagaacg tgagcagagg atagaatcta    1020
aacatagaaa aacccctatt gagaagaatc tacaaatgtg ggaagaaatg aaaaaaggga    1080
gccagtttgg tcagtcctgt tgtttgcgag caaaaattga catgagtagt aacaatggat    1140
gcatgagaga tccaaccctt tatcgctgca aaattcaacc acatccaaga actggaaata    1200
aatacaatgt ttatccaaca tatgattttg cctgccccat agttgacagc atcgaaggtg    1260
ttacacatgc cctgagaaca acagaatacc atgacagaga tgagcagttt tactggatta    1320
ttgaagcttt aggcataaga aaaccatata tttgggaata tagtcggcta aatctcaaca    1380
acacagtgct atccaaaaga aaactcacat ggtttgtcaa tgaaggacta gtagatggat    1440
gggatgaccc aagatttcct acggttcgtg tgtactgag aagagggatg acagttgaag    1500
gactgaaaca gtttattgct gctcagggct cctcacgttc agtcgtgaac atggagtggg    1560
acaaaatctg ggcgtttaac aaaaaggtta ttgacccagt ggctccacga tatgttgcat    1620
tactgaagaa agaagtgatc ccagtgaatg tacctgaagc tcaggaggag atgaaagaag    1680
tagccaaaca cccaaagaat cctgaggttg gcttgaagcc tgtgtggtat agtcccaaag    1740
ttttcattga aggtgctgat gcagagactt tttcggaggg tgagatggtt acatttataa    1800
attggggcaa cctcaacatt acaaaaatac acaaaaatgc agatggaaaa atcatatctc    1860
ttgatgcaaa gttgaatttg gaaaacaaag actacaagaa aaccactaag gtcacttggc    1920
ttgcagagac tacacatgct cttcctattc cagtaatctg tgtcacttat gagcacttga    1980
tcacaaagcc agtgctagga aaagacgagg acttaagca gtatgtcaac aagaacagta    2040
agcatgaaga gctaatgcta ggggatccct gccttaagga tttgaaaaaa ggagatatta    2100
tacaactcca gagaagagga ttcttcatat gtgatcaacc ttatgaacct gttagcccat    2160
atagttgcaa ggaagccccg tgtgttttga tatacattcc tgatgggcac acaaaggaaa    2220
tgccaacatc agggtcaaag gaaaagacca agtagaagc cacaaaaaat gagacctctg    2280
ctccttttaa ggaaagacca acaccttctc tgaataataa ttgtactaca tctgaggatt    2340
ccttggtcct ttacaataga gtggctgttc aaggagatgt ggttcgtgaa ttaaaagcca    2400
agaaagcacc aaaggaagat gtagatgcag ctgtaaaaca gcttttgtct ttgaaagctg    2460
aatataagga gaaactggc caggaatata aacctggaaa ccctcctgct gaaataggac    2520
agaatatttc ttctaattcc tcagcaagta ttctggaaag taaatctctg tatgatgaag    2580
ttgctgcaca agggaggtg gttcgtaagc taaaagctga aaatcccct aaggctaaaa    2640
```

-continued

```
taaatgaagc tgtagaatgc ttactgtccc tgaaggctca gtataaagaa aaaactggga   2700
aggagtacat acctggtcag cccccattat ctcaaagttc ggattcaagc ccaaccagaa   2760
attctgaacc tgctggttta gaaacaccag aagcgaaagt actttttgac aaagtagctt   2820
ctcaagggga agtagttcgg aaacttaaaa ctgaaaaagc ccctaaggat caagtagata   2880
tagctgttca agaactcctt cagctaaagg cacagtacaa gtctttgata ggagtagagt   2940
ataagcctgt gtcggccact ggagctgagg acaaagataa gaagaagaaa gaaaaagaaa   3000
ataaatctga aaagcagaat aagcctcaga aacaaaatga tggccaaagg aaagaccctt   3060
ctaaaaacca aggaggtggg ctctcatcaa gtggagcagg agaagggcag ggccctaaga   3120
aacagaccag gttgggtctt gaggcaaaaa aagaagaaaa tcttgctgat tggtattctc   3180
aggtcatcac aaagtcagaa atgattgaat accatgacat aagtggctgt tatattcttc   3240
gtccctgggc ctatgccatt tgggaagcca tcaaggactt ttttgatgct gagatcaaga   3300
aacttggtgt tgaaaactgc tacttcccca tgtttgtgtc tcaaagtgca ttagagaaag   3360
agaagactca tgttgctgac tttgccccag aggttgcttg ggttacaaga tctggcaaaa   3420
ccgagctggc agaaccaatt gccattcgtc ctactagtga aacagtaatg tatcctgcat   3480
atgcaaaatg ggtacagtca cacagagacc tgcccatcaa gctcaatcag tggtgcaatg   3540
tggtgcgttg ggaattcaag catcctcagc ctttcctacg tactcgtgaa tttctttggc   3600
aggaagggca cagtgctttt gctaccatgg aagaggcagc ggaagaggtc ttgcagatac   3660
ttgacttata tgctcaggta tatgaagaac tcctggcaat tcctgttgtt aaaggaagaa   3720
agacggaaaa ggaaaaattt gcaggaggag actatacaac tacaatagaa gcatttatat   3780
ctgctagtgg aagagctatc cagggaggaa catcacatca tttagggcag aatttttcca   3840
aaatgtttga aatcgttttt gaagatccaa agataccagg agagaagcaa tttgcctatc   3900
aaaactcctg ggtctgaca actcgaacta ttggtgttat gaccatggtt catggggaca   3960
acatgggttt agtattacca ccccgtgtag catgtgttca ggtggtgatt attccttgtg   4020
gcattaccaa tgcactttct gaagaagaca aagaagcgct gattgcaaaa tgcaatgatt   4080
atcgaaggcg attactcagt gttaacatcc gcgttagagc tgatttacga gataattatt   4140
ctccaggttg gaaattcaat cactgggagc tcaagggagt tcccattaga cttgaagttg   4200
ggccacgtga tatgaagagc tgtcagtttg tagccgtcag acgagatact ggagaaaagc   4260
tgacagttgc tgaaaatgag gcagagacta aacttcaagc tattttggaa gacatccagg   4320
tcaccctttt cacaagggct tctgaagacc ttaagactca tatggttgtg gctaatacaa   4380
tggaagactt tcagaagata ctagattctg gaaagattgt tcagattcca ttctgtgggg   4440
aaattgactg tgaggactgg atcaaaaaga ccactgccag ggatcaagat cttgaacctg   4500
gtgctccatc catgggagct aaaagccttt gcatcccctt caaaccactc tgtgaactgc   4560
agcctggagc caaatgtgtc tgtggcaaga accctgccaa gtactacacc ttatttggtc   4620
gcagctactg agggatgaac gaaagccccc tcttcaactc ctctcacttt ttaaagcatt   4680
gatattagta tcttctcaga tacagaccat tttatgattt tttaaaaagt aaaagttcta   4740
aaatgaagtc acacaggaca attattctta tgcctaagtt aacagtggat aaaagacttt   4800
tctgtaaaca actccagtaa taaatatcat gaactaaaaa aaaaaaaaaa              4850
```

<210> SEQ ID NO 35
<211> LENGTH: 1762
<212> TYPE: DNA

-continued

```
<213> ORGANISM: Homo sapiens
<220> FEATURE:
<221> NAME/KEY: misc_feature
<223> OTHER INFORMATION: Incyte ID No: 2742442CB1

<400> SEQUENCE: 35
attgcgcgag cgcacgggaa aagcgattgg tcggtcagga gagagaggtg tgtcctggcg      60
ggcccgcagc tccgattggc cgacaggctg acggaacgt ttacggtcag cgtgtgtcag     120
cgacgtgcaa ccgggaaggg aagaaggggc gtgtcaggct gcgcaggcgg ccagtccatt    180
ggctggaaga gaccggagcc gggctccggg cccgaccaga ggagggcggt gctgcagggc    240
tggtccggga ggtgacgacc ggcttcggag agtctatcat ggcagctcgg actggtcata    300
cggccttgag aagggtagtc tcgggatgcc gtccgaagtc ggcgacagcg gccggggcgc    360
aggcgcccgt gcggaatggc agatatttag cttcctgtgg tatactgatg agcagaactc    420
ttccactaca tacctcaatt tgcctaagg agatatgtgc acgaactttc ttcaaaatca    480
ctgcaccatt aataaacaaa aggaaagaat attcagagag aagaatttta ggatattcaa    540
tgcaggaaat gtatgatgta gtatcgggag tggaggatta caagcatttt gttccttggt    600
gcaaaaaatc agatgttata tcaagagat ctggatattg taaaacaaga ttagaaattg    660
gatttccacc tgtgttggag cgatatacat cagtagtaac cttggtgaaa cctcatttag    720
taaaggcatc ttgtactgat gggagacttt tcaatcattt ggagactatt tggtgttta    780
gcccaggtct tcctggctac ccaagaactt gtaccttgga ttttcaatt tcttttgaat    840
ttcgatcact tctacattcc cagcttgcca cactctttt tgatgaagtt gtgaagcaga    900
tggtagctgc ctttgaaaga agagcatgta agctgtatgg tccagaaaca aatatacctc    960
gggagttaat gcttcatgaa gtccatcaca cataaaggca aaaagaact ggtgccacct    1020
gcttctgact ttagtttgtt cacttttagg aagtattttc atgacatgtt ttcagaagcc    1080
agaaagcatt tgttaaacgc agctttggtt ataaacctgc accattgaaa atttgcacat    1140
agaatataga ctcacttgta catagaatta tttcttcaag tataattcaa ataatatgg    1200
acattatcat gttctgcatt acaataatgg gatgtcatca ccattgctag aatactggca    1260
tgattcttct gagcagaagt tgaaactgta aatttaaacc ttttaattat caccttacct    1320
gaaagaggtt agttaagata ttcacacagt atgtattata ttaaccatat cacacttaag    1380
ttattaaatt cagactattt gtaacttatt gttataggc ctgccgtatg gcttaggata    1440
tttgagtaat catatattta aagtaaaaac tttgggctgg gcacagtggc tcacacctgt    1500
aatcccagca cttggggaag ctgaggtggg cagatcagtt gaggtcagga gttctagacc    1560
agcctggtca acatggcgaa accccatctc tactaaaaat acaaaaatta gctgggcgtg    1620
gtggcacaca cctgtaatcc cagttacttg ggaggctgag gcacaagaat cgcttgaacc    1680
cgggaggcgg aggttgcagt tagccaagat cgccctgctg cactccagcc tgggcaacag    1740
agggagactc tgtctccaaa aa                                             1762
```

```
<210> SEQ ID NO 36
<211> LENGTH: 2862
<212> TYPE: DNA
<213> ORGANISM: Homo sapiens
<220> FEATURE:
<221> NAME/KEY: misc_feature
<223> OTHER INFORMATION: Incyte ID No: 3511087CB1

<400> SEQUENCE: 36
ctaagctcag aattcggctc gagtgctttt atttgctggt gttgaaagta gttcagccaa      60
```

```
acccatgaca gcttcatgaa tttaatcac atctttttt cttccgcagc cgtcagcttt     120
agtcagagga ccccttcaga cagccagtgt ctctcctagc atgccctttt cggcatcgct    180
gttaggaacc ttacccattg gtgcgaggta tgctcctcca ccctccttct cagaattta    240
tccacctttg acttcatcct tagaagattt ttgttcttct ttaaattcat tttcaatgag    300
tgaatccaaa cgagatctgt ccacctcaac ttctagagag ggaacaccgc ttaacaacag    360
taattcttcc cttttactta tgaatggacc aggtagtttg tttgcttcag agaattcct     420
gggaatttca agtcagccta gaaatgactt tggaaacttt tttggaagtg cagttaccaa    480
accatcttca tcagtgactc caagacatcc cctcgaagga acccatgaat gagacaagc     540
ttgccagatc tgttttgtaa atcaggccc taagttaatg gatttcactt accatgctaa     600
catagatcat aagtgtaaga agatatttt aatcggtagg ataaagaatg ttgaagataa    660
atcatggaaa aaatacgtc caagaccaac aaaaacaaat tatgaaggac catattatat    720
atgtaaagat gttgctgctg aggaggaatg tagatattca ggccactgca cgtttgctta    780
ttgccaagag gagatagatg tgtggacact ggagcgaaaa ggagcattca gccgggaggc    840
tttctttggc ggcaatggaa agattaacct tactgtgttc aaacttctcc aggagcatct    900
tgggaatttt atattccttt gtgagaaatg ttttgatcat aagcctagaa tgataagtaa    960
aagaaataaa gataattcta ctgcttgttc tcacccggtt acaaagcatg agtttgaaga   1020
caataagtgc cttgtccaca ttttgcgaga gacaacagta aaatactcca aaatacgttc   1080
ttttcatggt cagtgtcagc ttgatttatg tcgacatgaa gttcggtatg ctgtttaag    1140
ggaagatgag tgcttttatg cccatagtct tgtggaactg aaagtctgga taatgcaaaa   1200
tgaaacaggt atctcacatg atgctattgc tcaagagtct aaacgatatt ggcagaattt   1260
ggaagcaaat gtacctggag cgcaggtact tggtaatcaa ataatgcctg gatttcttaa   1320
tatgaagata aagtttgtgt gcgcccagtg tctgagaaac ggtcaagtca ttgaaccaga   1380
caaaaacaga aaatattgta gtgcaaaagc aaggcattcg tggaccaaag accggcgtgc   1440
gatgagagtg atgtctattg aacgtaagaa gtggatgaac atccgtcctc tccccacaaa   1500
gaaacaaatg cctttacagt ttgatctgtg caaccatatt gcttctggga aaaaatgtca   1560
atatgttgga aactgttcct tgctcatag tcctgaggaa agagaagttt ggacttacat    1620
gaaggagaat gggatacaag atatggagca atttacgaa ctatggctca agagtcaaaa   1680
aaatgaaaaa agtgaagaca tagccagtca gtcaaacaag gaaaatggaa aacaaattca   1740
catgccaaca gattatgctg aagttacagt ggactttcac tgctggatgt gtgggaaaaa   1800
ctgcaacagt gagaagcagt ggcagggcca catctcctcc gagaagcaca agagaaggt    1860
tttccacacc gaggacgacc agtactgctg gcagcaccgc ttcccaacag gctatttcag   1920
tatttgtgat aggtatatga atggcacctg cccagaagga acagctgta aatttgcaca    1980
tggaaatgcc gaacttcatg aatgggaaga agaagagat gccctaaaga tgaagctcaa    2040
caaagcacga aaagatcact taattggccc aaatgataat gactttggaa atatagttt    2100
tttgtttaaa gatttaaact aatatgctgg cttttatgta tgatacctaa tcagagcatt    2160
gaccagaaaa attgaaagtg ttctgaggca catagcagag gagctgcaga tttcctgctt    2220
gtattggcgt atatcgttcc tcctgagcag caacccacag taggtaggaa aatgggctgt    2280
ttcacaggcc tggccacgct ctcacggaac cactggcatc agatggtgaa gtgactgcta    2340
cccggttgcc atctgttgaa cagacttttg gatgaagtgt gttggggaag aggataaggt    2400
```

-continued

| | |
|---|---|
| tatatctagg acaactcttt gagttggtcc ttcatataag aatcgtgacg gtaagagaat | 2460 |
| aaacacttgt actgggatca gaatacatga tggatgaaat tctttacatg ttttagcaga | 2520 |
| atgaatttgt ttaatataat aaagtttgct acttatctgt atgtaggttg ctaaaaagga | 2580 |
| ttttcttaac tcagatttta agccaaataa ccatttaaca ctagtatttg ttaaatgggg | 2640 |
| tattttctg tatttgtatg tttcactata ataagggaat taaggataat gtgcattgag | 2700 |
| aatattttga aaaataattg actcaaattt tatttcttgg tcttttgctg tttaaatgat | 2760 |
| gattttgaaa gattaaacct gtactgttgg tattgtgtta gtgtatggac caatactgcc | 2820 |
| tgtaataaag attttatata tagatgcaaa aaaaaaaaaa aa | 2862 |

<210> SEQ ID NO 37
<211> LENGTH: 1263
<212> TYPE: DNA
<213> ORGANISM: Homo sapiens
<220> FEATURE:
<221> NAME/KEY: misc_feature
<223> OTHER INFORMATION: Incyte ID No: 1968009CB1

<400> SEQUENCE: 37

| | |
|---|---|
| ccgtccccat tctctgaccg cccctctccc ggtacactgc gcaggcacaa cagagccgct | 60 |
| cccctctcct cgccccgcca ccgggacgga gagcgcccgc cgctgcattt ccggcgacac | 120 |
| ctcgcagtca ttcctgcggc ttgcgcgccc ttgtagacag ccggggcctt cgtgagaccg | 180 |
| cttgttttct gcaggtgcag gcctgggta gtctcctgtc tggacagaga agagaaaat | 240 |
| gcaggacact ggctcagtag tgcctttgca ttggtttggc tttggctacg cagcactggt | 300 |
| tgcttctggt gggatcattg gctatgtaaa agcaggcagc gtgccgtccc tggctgcagg | 360 |
| gctgctcttt ggcagtctag ccggcctggg tgcttaccag ctgtctcagg atccaaggaa | 420 |
| cgtttgggtt ttcctagcta catctggtac cttggctggc attatgggaa tgaggttcta | 480 |
| ccactctgga aaattcatgc ctgcaggttt aattgcaggt gccagtttgc tgatggtcgc | 540 |
| caaagttgga gttagtatgt tcaacagacc ccattagcag aagtcatgtt ccagcttaga | 600 |
| ctgatgaaga attaaaaatc tgcatcttcc actattttca atatattaag agaaataagt | 660 |
| gcagcatttt tgcatctgac attttaccta aaaaaaaaga caccaaactt ggcagagagg | 720 |
| tggaaaatca gtcatgatta caaacctaca gaggtggcga gtatgtaaca caagagctta | 780 |
| ataagaccct catagagctt gattcttgta tattgatgaa gaattaaaaa tctgcatctt | 840 |
| ccactatttt caatatatta agagaaataa gtgcagcatt tttgcatctg acattttacc | 900 |
| taaaaaaaaa gacaccaaac ttggcagaga ggtggaaaat cagtcatgat tacaaaccta | 960 |
| cagaggtggc gagtatgtaa cacaagagct taataagacc ctcatagagc ttgattcttg | 1020 |
| tatattgatg ttgtctttc tttctgtatc tgtaggtaaa tctcaagggt aaaatgttag | 1080 |
| gtgtcagctt tcagggctct gaaacccat tccctgctct gaggaacagt gtgaaaaaaa | 1140 |
| gtcttttagg agatttacaa tatctgttct tttgctcatc ttagaccaca gactgacttt | 1200 |
| gaaattatgt taagtgaaat atcaatgaaa ataaagttta ctataaataa taaaaaaaaa | 1260 |
| aaa | 1263 |

<210> SEQ ID NO 38
<211> LENGTH: 978
<212> TYPE: DNA
<213> ORGANISM: Homo sapiens
<220> FEATURE:
<221> NAME/KEY: misc_feature
<223> OTHER INFORMATION: Incyte ID No: 1923127CB1

<400> SEQUENCE: 38

```
ctcgagccgc gcggcccegg ggcgcacgcg cacgcaatcg cgtttccgga gagacctggc      60
tgctgtgtcc cgcggcttgc gctccgtagt ggactccgcg ggccttcggc agatgcaggc     120
ctggggtagt ctcctttctg gactgagaag agaagaatgg agaagcccct cttcccatta     180
gtgcctttgc attggtttgg ctttggctac acagcactgg ttgtttctgg tgggatcgtt     240
ggctatgtaa aaacaggcag cgtgccgtcc ctggctgcag gctgctctt cggcagtcta      300
gccggcctgg gtgcttacca gctgtatcag gatccaagga acgtttgggg tttcctagcc     360
gctacatctg ttactttgt tggtgttatg ggaatgagat cctactacta tggaaaattc      420
atgcctgtag gtttaattgc aggtgccagt ttgctgatgg ccgccaaagt tggagttcgt     480
atgttgatga catctgatta gcagaagtca tgttccagct tggactcatg aaggattaaa     540
aatctgcatc ttccactatt tcaatgtat taagagaaat aagtgcagca tttttgcatc      600
tgacatttta cctaaaaaaa aaagacacc aaatttggcg gaggggtgga aaatcagttg      660
ttaccattat aaccctacag aggtggtgag catgtaacat gagcttattg agaccatcat     720
agagatcgat tcttgtatat tgattttatc tctttctgta tctataggta aatctcaagg     780
gtaaaatgtt aggtgttgac attgagaacc ctgaaacccc attccctgct cagaggaaca     840
gtgtgaaaaa aaatctcttg agagatttag aatatctttt cttttgctca tcttagacca     900
cagactgact ttgaaattat gttaagtgaa atatcaatga aataaagtt tactataaat      960
aataaaaaaa aaaaaaaa                                                   978
```

<210> SEQ ID NO 39
<211> LENGTH: 851
<212> TYPE: DNA
<213> ORGANISM: Homo sapiens
<220> FEATURE:
<221> NAME/KEY: misc_feature
<223> OTHER INFORMATION: Incyte ID No: 3123954CB1
<220> FEATURE:
<221> NAME/KEY: unsure
<222> LOCATION: 595, 600
<223> OTHER INFORMATION: a, t, c, g, or other

<400> SEQUENCE: 39

```
cggcacgcgt ggggtccgcg cgtgcgcacc ccgcgcgcgc ctctctgtcg tggcgcggct      60
tcccgcggtc ttctctgcaa atgggctccg tggcctagcg ccccgtccc cgccaccgt       120
gatcgtgcgc cgaggcccgc gagggtgtcgc cgcccagatc ccaccagcca gcaagctaaa    180
gcatggcggc catcccctcc agcggctcgc tcgtggccac ccacgactac taccggcgcc    240
gcctgggttc cacttccagc aacagctcct gcagcagtac cgagtgcccc ggggaagcca    300
ttccccaccc cccaggtctc cccaaggctg acccgggtca ttggtgggcc agcttctttt    360
tcgggaagtc caccctcccg ttcatggcca cggtgttgga gtccgcagag cactcggaac    420
ctccccaggc ctccagcagc atgaccgcct gtggcctggc tcgggacgcc ccgaggaagc    480
agcccggcgg tcagtccagc acagccagcg ctgggccccc gtcctgacct gagcggttac    540
caccagcccc aggcctgcgg aggcgctagt ccaccagagc cctcccgc ccctntcccn       600
aatccgcatc cctcgccccc ctcccccacct cccacccccc accctgtaaa ctaggcggct   660
gcagcaagca gacctttcgca tcaacacagc agacaccaaa aaccagtgag agccccgctc   720
tctaccgccc ggccccagca ctcgctagct ttcctgacac ctggaactgt gcacctggca    780
ccaagcggaa aataaactcc aagcagccag taaaaaaaaa aaaaaaaaaa aaaaaaaaa     840
```
aaaaaaaaag g    851

<210> SEQ ID NO 40
<211> LENGTH: 1907
<212> TYPE: DNA
<213> ORGANISM: Homo sapiens
<220> FEATURE:
<221> NAME/KEY: misc_feature
<223> OTHER INFORMATION: Incyte ID No: 1321844CB1

<400> SEQUENCE: 40

| | | | | | |
|---|---|---|---|---|---|
| tggaccgacg | ggcgcaccca | ggtaggggggg | cggctgagcc | gcgcagtgcg | gaccctcgcg | 60 |
| gggaactgcg | ccgccgccac | catgtctcag | gaaggtgtgg | agctggagaa | gagcgtccgg | 120 |
| ggcctccggg | agaagtttca | tgggaaggta | tcctccaaga | aggcggggc | tctgatgagg | 180 |
| aaattcggca | gcgaccacac | gggagtgggg | cgctccatcg | tgtacgggt | aaagcaaaaa | 240 |
| gatggccaag | aactaagtaa | cgatctggat | gcccaggatc | caccagaaga | tatgaagcag | 300 |
| gaccgggaca | ttcaggcagt | ggcgacctcc | ctcctgccac | tgacagaagc | caacctacgc | 360 |
| atgtttcaac | gtgcccagga | cgaccttatc | cctgctgtgg | accggcagtt | tgcctgctcc | 420 |
| tcctgcgacc | acgtctggtg | gcgccgcgtg | cccagcggca | aggaggtatc | ccggtgccgg | 480 |
| aaatgccgga | agcgctacga | gccagtgcca | gctgacaaga | tgtgggcct | ggctgagttc | 540 |
| cactgcccga | agtgtcggca | caacttccgg | ggctgggcac | agatggggtc | cccgtcccc | 600 |
| tgctacgggt | gcggcttccc | cgtgtatcca | acacggatcc | tccccccgcg | ctgggaccgg | 660 |
| gacccggatc | gccgcagcac | ccacactcac | tcctgctcag | ctgccgactg | ctacaaccgg | 720 |
| cgagagcccc | acgtgcctgg | gacatcctgt | gctcacccca | agagccggaa | gcagaaccac | 780 |
| ctgcccaaag | tgctccaccc | cagcaaccct | cacattagca | gtggctccac | tgtggccacc | 840 |
| tgcttgagcc | agggtggcct | cctggaagac | ctggacaacc | tcatcctgga | ggacctgaag | 900 |
| gaggaggagg | aggaagagga | ggaggtggag | gacgaggagg | gcgggcccag | ggagtgaccc | 960 |
| ctgccaggtg | cagatacaaa | ccagacacgg | tctgtggcta | ctttgtgtta | ttataagata | 1020 |
| tgagctcaaa | ccgagatatg | aatgaccttg | gggagccatc | tgaggccaag | atattgacgg | 1080 |
| gggggattcc | tgggtcccat | tttcagcgcc | cagggtcaca | gatccacagt | gggaagttct | 1140 |
| gtgggacaca | ttggcactga | gccacaaaga | aggtgtggcc | agaacaactt | gggctcctgc | 1200 |
| tgaccaatgt | cctctagggc | ctaggggaca | gaggaacaca | gagtcacagc | ttcaggggcc | 1260 |
| gaatgagcat | ggcggccttc | ctgagagaat | atgccccacc | acgaaactca | gcccagtaga | 1320 |
| caccatcctg | gtagcggctt | cggtagtggc | cgccgtggtg | ccacacaccg | ttgaggttgg | 1380 |
| agtgggcaca | ggcatggtac | caccagcctc | cccgctggta | caggggcacag | ttacctgagg | 1440 |
| ggagagagag | agtccatgtc | ctctcaccag | aataaaagcc | tctacctgca | cctcacagtg | 1500 |
| caaggctttt | gccaggcatc | ccctggcccc | tcccattctt | attgaataca | agccctgatc | 1560 |
| ttccatctcc | tcagcaaaaa | aataggagcc | ctggcccccc | aactttcttc | agagtaatag | 1620 |
| ccttaattcc | ttccctatct | ccttaccaaa | gtacaagtca | catctttccc | accttttctg | 1680 |
| caaactagga | gtctaccgtt | cattccttta | tcaaagaaaa | gtatctactt | cctttctaga | 1740 |
| ataagagtac | tagctctcac | cctctgccct | ttacttgaac | aggagtcttg | attcttttt | 1800 |
| tgcctcatca | gagaaggaat | ctggactccc | catcccccca | ccaggataaa | agtcctgacc | 1860 |
| tttgttctct | tgacggaata | aaagcttgct | tatccttaaa | aaaaaa | | 1907 |

-continued

```
<210> SEQ ID NO 41
<211> LENGTH: 408
<212> TYPE: DNA
<213> ORGANISM: Homo sapiens
<220> FEATURE:
<221> NAME/KEY: misc_feature
<223> OTHER INFORMATION: Incyte ID No: 375724.3

<400> SEQUENCE: 41
tttgtattaa acacatgttt atttacaacg tggagagaga ataagggggca gttaaggcca      60 cttctcctg tgaaacactg caaaatatgt acataagtac aacctaatat aggcaaaggt      120
tctaaaaatc atctttcttg gcttcacgta attgagtatc agtcggggag tggagagcgg      180
ctgccgatag caccaggcca tgcaggccac gctaacaagg gcgtgtgcat tcactttttc      240
attgagctgc cctcagagct gctgccgagc tgagccctgc acgggcccag gtgtgcgccg      300
ccagaagacg tcggtgcgaa ggctgtcgtt catgtaattc catgaggtct ggaccaggtg      360
ttggttacgc tcacactcta acacctgaag gtacataacg attatctt                   408

<210> SEQ ID NO 42
<211> LENGTH: 3689
<212> TYPE: DNA
<213> ORGANISM: Homo sapiens
<220> FEATURE:
<221> NAME/KEY: misc_feature
<223> OTHER INFORMATION: Incyte ID No: 375724.9
<220> FEATURE:
<221> NAME/KEY: unsure
<222> LOCATION: 3665, 3669, 3672, 3679, 3681
<223> OTHER INFORMATION: a, t, c, g, or other

<400> SEQUENCE: 42
tgggtccccc aggagagcct ctaaggtcac acagggtgcc cactgcagac aggctatagt      60
gcatggtgcc tcctccctga caaccacctc cacttcacac cagccacagc aaggaacttt      120
ggcaccagca tggatctctg cctgctgccg atggcatgac tgtcgaacag gtggtgttcc      180
atcagttctt tataccaagt cctttgtgaa gcattccaca gagcatgtgt caatggcctg      240
tgtccacctg gcttccaaga tagaagaggc cccaagacgc atacgggacg tcatcaatgt      300
gtttcaccgc cttcgacagc tgagagacaa aaaataatcg ttatgtacct tcaggtgtta      360
gagtgtgagc gtaaccaaca cctggtccag acctcatggg tagcctctga gggtaagtga      420
ctaagacttc tcctctgctg tccaagcgct ttggtgcagg gacagcggca tcttcagcca      480
atccagtgca ggctctccac cgaaggctgg ctctagactg gtgacccctt gttgaaatgg      540
gacagttggc agcggctctg atgagcccga agagaggcct gcccttgggt gcggagtctc      600
cctccgcacg atgctcccac gcgtccaact tgcacccaag gggcttttcc ctcttccaag      660
tggactcctt caaggaagct gcagctcggt cagcagagaa ggggcctgcc gccagcgccc      720
tggaggaaga ggaagaggaa cccaagagga tggcttgtct cccagcagcc acaccggctt      780
tgtgctcagc cagttcattt gagtttgcat gtttctctgc actatggatt ttgagcattt      840
agatttcttt aatcaaaagc gttttagtga ctccagtaga cattttcttt ctgaggcatc      900
gtgctttgca tgagagcagg ccaaggttga ggggaaaagt aaagttaaag tcggttctct      960
ttcatagcaa cacgtattgt ctgacattca gccagctttt tttttttctaa taatttctgt     1020 gcctttctgt cctgtatttta ctgtatttag aaaaagcagc tagaatattt ctccattaac     1080
tcttgagatt cacaggactg tctagctctg agtcctagca atagactcct tagaggagta     1140
gtacgtttat ctagattttc tctagataat gcaggcggaa gacctgggtt ccccgggtgg     1200
```

-continued

```
ggcattgcag ttcttcctgt gtttggcttc caggaattac atgaacgaca gccttcgcac      1260
cgacgtcttc gtggcggttc cagccagaga gcatcgcctg tgcctgcatt tatcttgctg      1320
cccggacgct ggagatccct ttgcccaatc gtccccattg gtttcttttg tttggagcaa      1380
ctgaagaaga aattcaggaa atctgcttaa agatcttgca gctttatgct cggaaaaagg      1440
ttgatctcac acacctggag ggtgaagtgg aaaaaagaaa gcacgctatc gaagagggca      1500
aaggcccaag cccggggcct gttgcctggg ggcacacagg tgctggatgg tacctcgggg      1560
ttctctcctg cccccaagct ggtggaatcc cccaaagaag gtaaagggag caagccttcc      1620
ccactgtctg tgaagaacac caagaggagg ctggagggcg ccaagaaagc caaggcggac      1680
agccccgtga acggcttgcc aaaggggcga gagagtcgga gtcggagccg gagccgtgag      1740
cagagctact cgaggtcccc atcccgatca gcgtctgcct aagaggagga aaagtgacag      1800
cggctccaca tctggtgggt ccaagttcgc agagccgctc ccggagcagg agtgactccc      1860
caccgagaca ggcccccgc agcgctccct acaaaggctc tgagattcgg ggctcccgga      1920
agtccaagga ctgcaagtac ccccagaagc acacaagtc tcggagcccg gagttcttcc      1980
cgttctcgaa gcaggtcact gggagcgggc ggataatccg ggaaaataca agaagaaaag      2040
tcattactac agagatcagc gacgagagcg ctcgaggtcg tatgaacgca caggccgtcg      2100
ctatgagcgg gaccaccctg gcacagcag gcatcggagg tgaggcgggg ttgcagtgac      2160
tggtggccgc aagcccttcc ctggggagta cctgatggct gcccttttgac ccccggtggc      2220 tgccctttga ccccgggtg tgctctcagc gcaagtggtc ctagaacagg attcttttg      2280 gaaatgtctg tcgactggac cttggtggat ttggaaatgg aactgaggga ccggtgacac      2340
gtgcttcaga ccggtctggg gtgcggcgca cacctgggcc cgtgcagggc tcagctcggc      2400
agcagctctg agggcagctc aatgaaaaag tgaatgcaca cgcccttgtt ggcgtggcct      2460
ggcatggcct ggtgctatcg gcagccgctc tccactcccc gactgatact caattacgtg      2520
aagccaagaa agatgatttt tagaaccttt gcctatatta ggttgtactt atgtacatat      2580
tttgcagtgt ttcacaggag aaagtggcct taactgcccc ttattctctc tccacgttgt      2640
aaataaacat gtgtttaata caagttaaag ctatgtatga aaactcagaa cttgaatccc      2700
gtcagcttaa aacttgtgta gggaatcctg acttttaaaa tgtgagggta tttggatctg      2760
tgttgaaagt cgtatatttt tatctgtgcg gtgctgagtg caggccacca gctcctaaat      2820
agaggttccc tatatgcgcg tatgacatgg tgaataaaca caactctctc cactcaggac      2880
atccggagcg ttatggacgt ggtaggtggt cgttctgtgt gcttgtgaaa gtgtccaggc      2940
gtgtgcacag ccagtgcggc ccacttccgg gctccttgct ccctgctgta ctgaagtttt      3000
ggattttgca tccaatcctg tgtgcctgcc cttctgccga agcttgtgag gggcctgagt      3060
cctctgccca tcaggatgac aggctccttc ctgcagggcc ataggaggga agttttggaa      3120
acacagaatg attccaaggt gctctcgttc ctgagggga ctggtttgta acccatgaca      3180
tctgtgggcg agagaggcag ctgggagcag gacacttgga gggtcacccc acgggggtgg      3240
cacctgcact ctgagtgccc ccactgtca tcagctgcct cttaccgtgg acacagtttt      3300
ggttttgggg actaggggc cccactcctg gtggtaccgt ttggacttac tagggcagtg      3360
ggacatatag gccggggcta gtgggataac ggggagttac gcctgatgac tttttttgatg      3420 gaatcctgca ttagatagct ggtgggaccc cccctcaga attggggaac tgaggagact      3480
ccagggaggg tgtccttcca gggagagcag ctatgagggg cccctagct tcctgtgcct      3540 ggaagtaaga gaaccagtaa aaggccatac acacctgtac ccaagagacc gctctccatt      3600
```

```
tgctttcttt ttttactaaa taattgtaaa atattattat gacataaaga accatttaag    3660
gccanaaana anaagactna naaaaaaag                                      3689

<210> SEQ ID NO 43
<211> LENGTH: 3136
<212> TYPE: DNA
<213> ORGANISM: Homo sapiens
<220> FEATURE:
<221> NAME/KEY: misc_feature
<223> OTHER INFORMATION: Incyte ID No: 1867333CB1

<400> SEQUENCE: 43
cgacgccggc gtgatgtggc ttccgctggt gctgctcctg gctgtgctgc tgctggccgt      60
cctctgcaaa gtttacttgg gactattctc tggcagctcc ccgaatcctt tctccgaaga    120
tgtcaaacgg cccccagcgc ccctggtaac tgacaaggag gccaggaaga aggttctcaa    180
acaagctttt tcagccaacc aagtgccgga gaagctggat gtggtggtaa ttggcagtgg    240
ctttgggggc ctggctgcag ctgcaattct agctaaagct ggcaagcgag tcctggtgct    300
ggaacaacat accaaggcag ggggctgctg tcatacccttt ggaaagaatg gccttgaatt    360
tgacacagga atccattaca ttgggcgtat ggaagagggc agcattggcc gttttatctt    420
ggaccagatc actgaagggc agctggactg gctcccctg tcctctcctt ttgacatcat    480
ggtactggaa gggcccaatg ccgaaagga gtaccccatg tacagtggag agaaagccta    540
cattcagggc ctcaaggaga gtttccaca ggaggaagct atcattgaca gtatataaa     600 gctggttaag gtggtatcca gtggagcccc tcatgccatc ctgttgaaat tcctcccatt    660
gcccgtggtt cagctcctcg acaggtgtgg gctgctgact cgtttctctc cattccttca    720
agcatccacc cagagcctgg ctgaggtcct gcagcagctg ggggcctcct ctgagctcca    780
ggcagtactc agctacatct tccccactta cggtgtcacc cccaaccaca gtgccttttc    840
catgcacgcc ctgctggtca accactacat gaaaggaggc ttttatcccc gagggggttc    900
cagtgaaatt gccttccaca ccatccctgt gattcagcgg gctgggggcg ctgtcctcac    960
aaaggccact gtgcagagtg tgttgctgga ctcagctggg aaagcctgtg gtgtcagtgt    1020
gaagaagggg catgagctgg tgaacatcta ttgcccccatc gtggtctcca acgcaggact    1080
gttcaacacc tatgaacacc tactgccggg gaacgcccgc tgcctgccag gtgtgaagca    1140
gcaactgggg acggtgcggc ccggcttagg catgacctct gttttcatct gcctgcgagg    1200
caccaaggaa gacctgcatc tgccgtccac caactactat gtttactatg cacggacat    1260 ggaccaggcg atgagcgct acgtctccat gcccagggaa gaggctgcgg aacacatccc    1320
tcttctcttc ttcgctttcc catcagccaa agatccgacc tgggaggacc gattcccagg    1380
ccggtccacc atgatcatgc tcataccac tgcctacgag tggtttgagg agtggcaggc    1440
ggagctgaag ggaaagcggg gcagtgacta tgagaccttc aaaaactcct ttgtggaagc    1500
ctctatgtca gtggtcctga aactgttccc acagctggag gggaaggtgg agagtgtgac    1560
tgcaggatcc ccactcacca accagttcta tctggctgct ccccgaggtg cctgctacgg    1620
ggctgaccat gacctgggcc gcctgcaccc ttgtgtgatg gcctccttga gggcccagag    1680
ccccatcccc aacctctatc tgacaggcca ggatatcttc acctgtggac tggtcggggc    1740
cctgcaaggt gccctgctgt gcagcagcgc atcctgaag cggaacttgt actcagacct    1800
taagaatctt gattctagga tccgggcaca gaagaaaaag aattagttcc atcagggagg    1860
agtcagagga atttgcccaa tggctggggc atctcccttg acttacccat aatgtctttc    1920
```

-continued

```
tgcattagtt ccttgcacgt ataaagcact ctaatttggt tctgatgcct gaagagaggc    1980
ctagtttaaa tcacaattcc gaatctgggg caatggaatc actgcttcca gctggggcag    2040
gtgagatctt tacgccttt ataacatgcc atccctacta ataggatatt gacttggata     2100
gcttgatgtc tcatgacgag cggcgctctg catccctcac ccatgcctcc taactcagtg    2160
atcaaagcga atattccatc tgtggataga acccctggca gtgttgtcag ctcaacctgg    2220
tgggttcagt tctgtcctga ggcttctgct ctcattcatt tagtgctacg ctgcacagtt    2280
ctacactgtc aagggaaaag ggagactaat gaggcttaac tcaaaacctg gcatggtttt    2340
tggttgccat tccataggtt tggagagctc tagatctctt ttgtgctggg ttcagtggct    2400
cttcagggga caggaaatgc ctgtgtctgg ccagtgtggt tctggagctt ggggtaaca    2460 gcaggatcca tcagttagta gggtgcatgt cagatgatca tatccaattc atatggaagt    2520
cccgggtctg tcttccttat catcggggtg gcagctggtt ctcaatgtgc cagcagggac    2580
tcagtacctg agcctcaatc aagccttatc caccaaatac acagggaagg gtgatgcagg    2640
gaagggtgac atcaggagtc agggcatgga ctggtaagat gaatactttg ctgggctgaa    2700
gcaggctgca gggcattcca gccaagggca cagcagggga cagtgcaggg aggtgtgggg    2760
taagggaggg aagtcacatc agaaaaggga aagccacgga atgtgtgtga agcccagaaa    2820
tggcatttgc agttaattag cacatgtgag ggttagacag gtaggtgaat gcaagctcaa    2880
ggtttggaaa aatgactttt cagttatgtc tttggtatca gacatacgaa aggtctcttt    2940
gtagttcgtg ttaatgtaac attaataaat ttattgattc cattgcttta acatttgaaa    3000
tttattttgg tttttgttc aagaaaacaa aactattatt gtgatggcat ttgcagaagc    3060
tcagtaaaac actatatact gaataacacc aaataagct ttaaaaaat aaaattaagt      3120 aattataaaa aaaaaa                                                    3136
```

<210> SEQ ID NO 44
<211> LENGTH: 1376
<212> TYPE: DNA
<213> ORGANISM: Homo sapiens
<220> FEATURE:
<221> NAME/KEY: misc_feature
<223> OTHER INFORMATION: Incyte ID No: 1461451CB1

<400> SEQUENCE: 44

```
ccacgcgtcc gcggacggtg ggtcgcccac gcgtccgccc acgcgtccgc ccacgcgtcc      60
gatgagatcc cggcctcagg gtggacgcag tggttctgca ctgaggccct cgtcatggtg     120
gcgcctgtgt ggtacttggt agcggcggct ctgctagtcg gctttatcct cttcctgact     180
cgcagccggg gccggcggc atcagccggc caagagccac tgcacaatga ggagctggca     240
ggagcaggcc gggtggccca gcctgggccc ctggagcctg aggagccgag agctggaggc     300
aggcctcggc gccggaggga cctgggcagc cgcctacagg cccagcgtcg agcccagcgg     360
gtggcctggg cagaagcaga tgagaacgag gaggaagctg tcatcctagc ccaggaggag     420
gaaggtgtcg agaagccagc ggaaactcac ctgtcgggga aaattggagc taagaaactg     480
cggaagctgg aggagaaaca agcgcgaaag gcccagcgtg aggcagagga ggctgaacgt     540
gaggagcgga aacgactcga gtcccagcgc gaagctgagt ggaagaagga ggaggagcgg     600
cttcgcctgg aggaggagca aaggaggag gaggagagga aggcccgcga ggagcaggcc     660
cagcgggagc atgaggagta cctgaaactg aaggaggcct ttgtggtgga ggaggaaggc     720
gtaggagaga ccatgactga ggaacagtcc cagagcttcc tgacagagtt catcaactac     780
```

```
atcaagcagt ccaaggttgt gctcttggaa gacctggctt cccaggtggg cctacgcact      840
caggacacca taaatcgcat ccaggacctg ctggctgagg ggactataac aggtgtgatt      900
gacgaccggg gcaagttcat ctacataacc ccagaggaac tggccgccgt ggccaacttc      960
atccgacagc ggggccgggt gtccatcgcc gagcttgccc aagccagcaa ctccctcatc     1020
gcctggggcc gggagtcccc tgcccaagcc ccagcctgac cccagtcctt ccctcttgga     1080
ctcagagttg gtgtggccta cctggctata catcttcatc cctccccacc atcctgggga     1140
agtgatggtg tggccaggca gttatagatt aaaggcctgt gagtactgct gagcttggtg     1200
tggcttggtg tggcagaagg cctggcctag gatcctagat aagcaggtga aatttaggct     1260
tcagaatata tccgagaggt ggggagggtc ccttggaagc tggtgaagtc ctgttcttat     1320
tatgaatcca ttcattcaag aaaatagcct gttgcacatt taaaaaaaaa aaaaaa        1376
```

<210> SEQ ID NO 45
<211> LENGTH: 649
<212> TYPE: DNA
<213> ORGANISM: Homo sapiens
<220> FEATURE:
<221> NAME/KEY: misc_feature
<223> OTHER INFORMATION: Incyte ID No: 2345712CB1

<400> SEQUENCE: 45

```
ctacgacccg attggcttcg ggctcagctg ggaggcggga cgaattattg gttgggggaa       60
acccacgagg ggacgcggcc gaggagggtc gctgtccacc cggggcgtg ggagtgaggt      120 accagattca gcccatttgg ccccgacgcc tctgttctcg gaatccgggt gctgcggatt      180
gaggtcccgg ttcctaacgg actgcaagat ggaggaaggc gggaacctag gaggcctgat      240
taagatggtc catctactgg tcttgtcagg tgcctggggc atgcaaatgt gggtgacctt      300
cgtctcaggc ttcctgcttt tccgaagcct tccccgacat accttcggac tagtgcagag      360
caaactcttc cccttctact tccacatctc catgggctgt gccttcatca acctctgcat      420
cttggcttca cagcatgctt gggctcagct cacattctgg gaggccagcc agctttacct      480
gctgttcctg agccttacgc tggccactgt caacgcccgc tggctggaac cccgcaccac      540
agctgccatg tgggccctgc aaaccgtgga aaggagcga ggcctgggtg gggaggtacc      600
aggcagccac cagggttccg atccctaccg ccagctgcga gagaaggac                  649
```

<210> SEQ ID NO 46
<211> LENGTH: 1554
<212> TYPE: DNA
<213> ORGANISM: Homo sapiens
<220> FEATURE:
<221> NAME/KEY: misc_feature
<223> OTHER INFORMATION: Incyte ID No: 1810320CB1

<400> SEQUENCE: 46

```
ctcccggttc caggcgagtt cgcagctgcg cgccgggtcc tggaggccga ggccgctccc       60
gcccgttgtc cccgcagtcc ccgacgggag cgccatggcc cagccgccgc ccgacgtgga      120
gggggacgac tgtctccccg cgtaccgcca cctcttctgc ccggacctgc tgcgggacaa      180
agtggccttc atcacaggag gcggctctgg gattgggttc cggattgctg agattttcat      240
gcggcacggc tgccatacgg tgattgccag taggagcctg ccgcgagtgc tgacggccgc      300
caggaagctg gctggggcca ccggccgcg ctgcctccct ctctctatgg acgtccgagc      360
gcccccagct gtcatggccg ccgtggacca ggctctgaag gagtttggca gaatcgacat      420
```

| | |
|---|---|
| tctcattaac tgtgcggccg ggaacttcct gtgccccgct ggcgccttgt ccttcaacgc | 480 |
| cttcaagacc gtgatggaca tcgataccag cggcaccttc aatgtgtctc gtgtgctcta | 540 |
| tgagaagttc ttccgggacc acggaggggt gatcgtgaac atcactgcca ccctggggaa | 600 |
| ccgggggcag gcgctccagg tgcatgcagg ctccgccaag gccgctgtgg acgcgatgac | 660 |
| gcggcacttg gctgtggagt ggggtcccca aaacatccgc gtcaacagcc tcgcccctgg | 720 |
| ccccatcagt ggcacagagg ggctccggcg actgggtggc cctcaggcca gcctgagcac | 780 |
| caaggtcact gccagcccgc tgcagaggct ggggaacaag accgagatcg cccacagcgt | 840 |
| gctctacctg gccagccctc tggcttccta cgtgacgggg gccgtgctgg tggccgatgg | 900 |
| cggggcatgg ttgacgttcc caaacggtgt caaagggctg ccggatttcg catccttctc | 960 |
| tgctaagctc taggaatctt ccggccgctg cttcctgccg cctcactcag ccaggtggag | 1020 |
| agcaccaatc tgaaccagca atgcctgcag cccagccccc tctctgaaca ctcagctatt | 1080 |
| actgcgcttt ccctccccac ggccccaact ccagggcagg agcaactgga cagtgggcct | 1140 |
| ggcccgtgga gctgccacgc aggtgcctga gggcaggtg ccacgcaggt gtctgaggac | 1200 |
| caggtgccac gcaggtggtg ggggtacaga caagatgctg ggatgtcccc tgccccatgg | 1260 |
| tcaagggtgt cctgcctgcc tgggtccagg gcctgaggga gccacatgga tcccgagact | 1320 |
| tgtgttctct tggctgaaaa cactgaggtg ctcccatctg tgcgtggccc atgagctggg | 1380 |
| atggtcctcc agctgcccac aaggtccgcc cctctgtctc tgcaccacct gtttgcataa | 1440 |
| acacactttg ctacaatctt gctagtgcgt tttcttaaaa gataatctat ttactgtaaa | 1500 |
| aataaattgg actttgcaaa agcttttaga aggaaaagaa agaggattaa aggg | 1554 |

<210> SEQ ID NO 47
<211> LENGTH: 1083
<212> TYPE: DNA
<213> ORGANISM: Homo sapiens
<220> FEATURE:
<221> NAME/KEY: misc_feature
<223> OTHER INFORMATION: Incyte ID No: 964996CB1

<400> SEQUENCE: 47

| | |
|---|---|
| gagccgtcag tcttacaaag tcgtgactgg caaaacctgg cgttaccaac ttaatcgcct | 60 |
| tgcagcacat gcctctgacc gccttcggca cgtccagatt ctgtgggaca tacagggtct | 120 |
| gggctcctct ggaaaccagg gacccgatgc cggagggtag cttggctctg gagcagcctg | 180 |
| ggactatagg aaggagggcc ctcctggacc cgggagcgga ccctggtggc ggtgaagccc | 240 |
| gatggcgtgc aacggcggct cgttggggac gtgatccagc gctttgagag gcggggcttc | 300 |
| acgctggtgg ggatgaagat gctgcaggca ccagagagcg tccttgccga gcactaccag | 360 |
| gacctgcgga ggaagccctt ctaccctgcc ctcatccgct acatgagctc tgggcctgtg | 420 |
| gtggccatgg tctgggaagg gtacaatgtc gtccgcgcct cgagggccat gattggacac | 480 |
| accgactcgg ctgaggctgc ccaggaacc ataaggggtt acttcagcgt ccacatcagc | 540 |
| aggaatgtca tccacgccag cgactccgtg gaggggggccc agcgggagat ccagctgtgg | 600 |
| ttccagagca gtgagctggt gagctgggca gatggggggcc agcacagcag catccaccca | 660 |
| gcctgaggct caagctgccc ttaccacccc atccccacg caggaccaac tacctccgtc | 720 |
| agcaagaacc caagcccaca tccaaacctg cctgtcccaa accacttact tccctgttca | 780 |
| cctctgcccc accccagccc agaggagttt gagccaccaa cttcagtgcc tttctgtacc | 840 |
| ccaagccagc acaagattgg accaatcctt tttgcaccaa agtgccggac aacctttgtg | 900 |

-continued

```
gtggggggggg gtcttcacat tatcataacc tctcctctaa agggggaggca ttaaaattca    960 ctgtgcccag cacatgggtg gtacactaat tatgacttcc cccagctctg aggtagaaat   1020
gacgccttta tgcaagttgt aaggagttga acagtaaaga ggaagttttg cacaaaaaaa   1080
aaa                                                                 1083
```

```
<210> SEQ ID NO 48
<211> LENGTH: 1512
<212> TYPE: PRT
<213> ORGANISM: Homo sapiens
<220> FEATURE:
<221> NAME/KEY: misc_feature
<223> OTHER INFORMATION: Incyte ID No: 2302721CD1

<400> SEQUENCE: 48
```

```
Met Ala Thr Leu Ser Leu Thr Val Asn Ser Gly Asp Pro Pro Leu
 1               5                  10                  15

Gly Ala Leu Leu Ala Val Glu His Val Lys Asp Asp Val Ser Ile
                20                  25                  30

Ser Val Glu Glu Gly Lys Glu Asn Ile Leu His Val Ser Glu Asn
                35                  40                  45

Val Ile Phe Thr Asp Val Asn Ser Ile Leu Arg Tyr Leu Ala Arg
            50                  55                  60

Val Ala Thr Thr Ala Gly Leu Tyr Gly Ser Asn Leu Met Glu His
        65                  70                  75

Thr Glu Ile Asp His Trp Leu Glu Phe Ser Ala Thr Lys Leu Ser
            80                  85                  90

Ser Cys Asp Ser Phe Thr Ser Thr Ile Asn Glu Leu Asn His Cys
            95                 100                 105

Leu Ser Leu Arg Thr Tyr Leu Val Gly Asn Ser Leu Ser Leu Ala
            110                 115                 120

Asp Leu Cys Val Trp Ala Thr Leu Lys Gly Asn Ala Ala Trp Gln
            125                 130                 135

Glu Gln Leu Lys Gln Lys Lys Ala Pro Val His Val Lys Arg Trp
            140                 145                 150

Phe Gly Phe Leu Glu Ala Gln Gln Ala Phe Gln Ser Val Gly Thr
            155                 160                 165

Lys Trp Asp Val Ser Thr Thr Lys Ala Arg Val Ala Pro Glu Lys
            170                 175                 180

Lys Gln Asp Val Gly Lys Phe Val Glu Leu Pro Gly Ala Glu Met
            185                 190                 195

Gly Lys Val Thr Val Arg Phe Pro Pro Glu Ala Ser Gly Tyr Leu
            200                 205                 210

His Ile Gly His Ala Lys Ala Ala Leu Leu Asn Gln His Tyr Gln
            215                 220                 225

Val Asn Phe Lys Gly Lys Leu Ile Met Arg Phe Asp Asp Thr Asn
            230                 235                 240

Pro Glu Lys Glu Lys Glu Asp Phe Glu Lys Val Ile Leu Glu Asp
            245                 250                 255

Val Ala Met Leu His Ile Lys Pro Asp Gln Phe Thr Tyr Thr Ser
            260                 265                 270

Asp His Phe Glu Thr Ile Met Lys Tyr Ala Glu Lys Leu Ile Gln
            275                 280                 285

Glu Gly Lys Ala Tyr Val Asp Asp Thr Pro Ala Glu Gln Met Lys
            290                 295                 300
```

-continued

```
Ala Glu Arg Glu Gln Arg Ile Glu Ser Lys His Arg Lys Asn Pro
            305                 310                 315
Ile Glu Lys Asn Leu Gln Met Trp Glu Met Lys Lys Gly Ser
            320                 325                 330
Gln Phe Gly Gln Ser Cys Cys Leu Arg Ala Lys Ile Asp Met Ser
            335                 340                 345
Ser Asn Asn Gly Cys Met Arg Asp Pro Thr Leu Tyr Arg Cys Lys
            350                 355                 360
Ile Gln Pro His Pro Arg Thr Gly Asn Lys Tyr Asn Val Tyr Pro
            365                 370                 375
Thr Tyr Asp Phe Ala Cys Pro Ile Val Asp Ser Ile Glu Gly Val
            380                 385                 390
Thr His Ala Leu Arg Thr Thr Glu Tyr His Asp Arg Asp Glu Gln
            395                 400                 405
Phe Tyr Trp Ile Ile Glu Ala Leu Gly Ile Arg Lys Pro Tyr Ile
            410                 415                 420
Trp Glu Tyr Ser Arg Leu Asn Leu Asn Asn Thr Val Leu Ser Lys
            425                 430                 435
Arg Lys Leu Thr Trp Phe Val Asn Glu Gly Leu Val Asp Gly Trp
            440                 445                 450
Asp Asp Pro Arg Phe Pro Thr Val Arg Gly Val Leu Arg Arg Gly
            455                 460                 465
Met Thr Val Glu Gly Leu Lys Gln Phe Ile Ala Ala Gln Gly Ser
            470                 475                 480
Ser Arg Ser Val Val Asn Met Glu Trp Asp Lys Ile Trp Ala Phe
            485                 490                 495
Asn Lys Lys Val Ile Asp Pro Val Ala Pro Arg Tyr Val Ala Leu
            500                 505                 510
Leu Lys Lys Glu Val Ile Pro Val Asn Val Pro Glu Ala Gln Glu
            515                 520                 525
Glu Met Lys Glu Val Ala Lys His Pro Lys Asn Pro Glu Val Gly
            530                 535                 540
Leu Lys Pro Val Trp Tyr Ser Pro Lys Val Phe Ile Glu Gly Ala
            545                 550                 555
Asp Ala Glu Thr Phe Ser Glu Gly Glu Met Val Thr Phe Ile Asn
            560                 565                 570
Trp Gly Asn Leu Asn Ile Thr Lys Ile His Lys Asn Ala Asp Gly
            575                 580                 585
Lys Ile Ile Ser Leu Asp Ala Lys Leu Asn Leu Glu Asn Lys Asp
            590                 595                 600
Tyr Lys Lys Thr Thr Lys Val Thr Trp Leu Ala Glu Thr Thr His
            605                 610                 615
Ala Leu Pro Ile Pro Val Ile Cys Val Thr Tyr Glu His Leu Ile
            620                 625                 630
Thr Lys Pro Val Leu Gly Lys Asp Glu Asp Phe Lys Gln Tyr Val
            635                 640                 645
Asn Lys Asn Ser Lys His Glu Glu Leu Met Leu Gly Asp Pro Cys
            650                 655                 660
Leu Lys Asp Leu Lys Lys Gly Asp Ile Ile Gln Leu Gln Arg Arg
            665                 670                 675
Gly Phe Phe Ile Cys Asp Gln Pro Tyr Glu Pro Val Ser Pro Tyr
            680                 685                 690
Ser Cys Lys Glu Ala Pro Cys Val Leu Ile Tyr Ile Pro Asp Gly
```

-continued

```
                695                 700                 705
His Thr Lys Glu Met Pro Thr Ser Gly Ser Lys Glu Lys Thr Lys
                710                 715                 720

Val Glu Ala Thr Lys Asn Glu Thr Ser Ala Pro Phe Lys Glu Arg
                725                 730                 735

Pro Thr Pro Ser Leu Asn Asn Asn Cys Thr Thr Ser Glu Asp Ser
                740                 745                 750

Leu Val Leu Tyr Asn Arg Val Ala Val Gln Gly Asp Val Val Arg
                755                 760                 765

Glu Leu Lys Ala Lys Lys Ala Pro Lys Glu Asp Val Asp Ala Ala
                770                 775                 780

Val Lys Gln Leu Leu Ser Leu Lys Ala Glu Tyr Lys Glu Lys Thr
                785                 790                 795

Gly Gln Glu Tyr Lys Pro Gly Asn Pro Pro Ala Glu Ile Gly Gln
                800                 805                 810

Asn Ile Ser Ser Asn Ser Ser Ala Ser Ile Leu Glu Ser Lys Ser
                815                 820                 825

Leu Tyr Asp Glu Val Ala Ala Gln Gly Glu Val Val Arg Lys Leu
                830                 835                 840

Lys Ala Glu Lys Ser Pro Lys Ala Lys Ile Asn Glu Ala Val Glu
                845                 850                 855

Cys Leu Leu Ser Leu Lys Ala Gln Tyr Lys Glu Lys Thr Gly Lys
                860                 865                 870

Glu Tyr Ile Pro Gly Gln Pro Pro Leu Ser Gln Ser Ser Asp Ser
                875                 880                 885

Ser Pro Thr Arg Asn Ser Glu Pro Ala Gly Leu Glu Thr Pro Glu
                890                 895                 900

Ala Lys Val Leu Phe Asp Lys Val Ala Ser Gln Gly Glu Val Val
                905                 910                 915

Arg Lys Leu Lys Thr Glu Lys Ala Pro Lys Asp Gln Val Asp Ile
                920                 925                 930

Ala Val Gln Glu Leu Leu Gln Leu Lys Ala Gln Tyr Lys Ser Leu
                935                 940                 945

Ile Gly Val Glu Tyr Lys Pro Val Ser Ala Thr Gly Ala Glu Asp
                950                 955                 960

Lys Asp Lys Lys Lys Glu Lys Glu Asn Lys Ser Glu Lys Gln
                965                 970                 975

Asn Lys Pro Gln Lys Gln Asn Asp Gly Gln Arg Lys Asp Pro Ser
                980                 985                 990

Lys Asn Gln Gly Gly Gly Leu Ser Ser Gly Ala Gly Glu Gly
                995                1000                1005

Gln Gly Pro Lys Lys Gln Thr Arg Leu Gly Leu Glu Ala Lys Lys
               1010                1015                1020

Glu Glu Asn Leu Ala Asp Trp Tyr Ser Gln Val Ile Thr Lys Ser
               1025                1030                1035

Glu Met Ile Glu Tyr His Asp Ile Ser Gly Cys Tyr Ile Leu Arg
               1040                1045                1050

Pro Trp Ala Tyr Ala Ile Trp Glu Ala Ile Lys Asp Phe Phe Asp
               1055                1060                1065

Ala Glu Ile Lys Lys Leu Gly Val Glu Asn Cys Tyr Phe Pro Met
               1070                1075                1080

Phe Val Ser Gln Ser Ala Leu Glu Lys Glu Lys Thr His Val Ala
               1085                1090                1095
```

-continued

```
Asp Phe Ala Pro Glu Val Ala Trp Val Thr Arg Ser Gly Lys Thr
                1100                1105                1110
Glu Leu Ala Glu Pro Ile Ala Ile Arg Pro Thr Ser Glu Thr Val
            1115                1120                1125
Met Tyr Pro Ala Tyr Ala Lys Trp Val Gln Ser His Arg Asp Leu
            1130                1135                1140
Pro Ile Lys Leu Asn Gln Trp Cys Asn Val Val Arg Trp Glu Phe
            1145                1150                1155
Lys His Pro Gln Pro Phe Leu Arg Thr Arg Glu Phe Leu Trp Gln
            1160                1165                1170
Glu Gly His Ser Ala Phe Ala Thr Met Glu Glu Ala Ala Glu Glu
            1175                1180                1185
Val Leu Gln Ile Leu Asp Leu Tyr Ala Gln Val Tyr Glu Glu Leu
            1190                1195                1200
Leu Ala Ile Pro Val Val Lys Gly Arg Lys Thr Glu Lys Glu Lys
            1205                1210                1215
Phe Ala Gly Gly Asp Tyr Thr Thr Thr Ile Glu Ala Phe Ile Ser
            1220                1225                1230
Ala Ser Gly Arg Ala Ile Gln Gly Gly Thr Ser His His Leu Gly
            1235                1240                1245
Gln Asn Phe Ser Lys Met Phe Glu Ile Val Phe Glu Asp Pro Lys
            1250                1255                1260
Ile Pro Gly Glu Lys Gln Phe Ala Tyr Gln Asn Ser Trp Gly Leu
            1265                1270                1275
Thr Thr Arg Thr Ile Gly Val Met Thr Met Val His Gly Asp Asn
            1280                1285                1290
Met Gly Leu Val Leu Pro Pro Arg Val Ala Cys Val Gln Val Val
            1295                1300                1305
Ile Ile Pro Cys Gly Ile Thr Asn Ala Leu Ser Glu Glu Asp Lys
            1310                1315                1320
Glu Ala Leu Ile Ala Lys Cys Asn Asp Tyr Arg Arg Arg Leu Leu
            1325                1330                1335
Ser Val Asn Ile Arg Val Arg Ala Asp Leu Arg Asp Asn Tyr Ser
            1340                1345                1350
Pro Gly Trp Lys Phe Asn His Trp Glu Leu Lys Gly Val Pro Ile
            1355                1360                1365
Arg Leu Glu Val Gly Pro Arg Asp Met Lys Ser Cys Gln Phe Val
            1370                1375                1380
Ala Val Arg Arg Asp Thr Gly Glu Lys Leu Thr Val Ala Glu Asn
            1385                1390                1395
Glu Ala Glu Thr Lys Leu Gln Ala Ile Leu Glu Asp Ile Gln Val
            1400                1405                1410
Thr Leu Phe Thr Arg Ala Ser Glu Asp Leu Lys Thr His Met Val
            1415                1420                1425
Val Ala Asn Thr Met Glu Asp Phe Gln Lys Ile Leu Asp Ser Gly
            1430                1435                1440
Lys Ile Val Gln Ile Pro Phe Cys Gly Glu Ile Asp Cys Glu Asp
            1445                1450                1455
Trp Ile Lys Lys Thr Thr Ala Arg Asp Gln Asp Leu Glu Pro Gly
            1460                1465                1470
Ala Pro Ser Met Gly Ala Lys Ser Leu Cys Ile Pro Phe Lys Pro
            1475                1480                1485
```

-continued

Leu Cys Glu Leu Gln Pro Gly Ala Lys Cys Val Cys Gly Lys Asn
                1490                1495                1500

Pro Ala Lys Tyr Tyr Thr Leu Phe Gly Arg Ser Tyr
                1505                1510

<210> SEQ ID NO 49
<211> LENGTH: 238
<212> TYPE: PRT
<213> ORGANISM: Homo sapiens
<220> FEATURE:
<221> NAME/KEY: misc_feature
<223> OTHER INFORMATION: Incyte ID No: 2742442CD1

<400> SEQUENCE: 49

Met Ala Ala Arg Thr Gly His Thr Ala Leu Arg Arg Val Val Ser
 1               5                  10                  15

Gly Cys Arg Pro Lys Ser Ala Thr Ala Ala Gly Ala Gln Ala Pro
                20                  25                  30

Val Arg Asn Gly Arg Tyr Leu Ala Ser Cys Gly Ile Leu Met Ser
                35                  40                  45

Arg Thr Leu Pro Leu His Thr Ser Ile Leu Pro Lys Glu Ile Cys
                50                  55                  60

Ala Arg Thr Phe Phe Lys Ile Thr Ala Pro Leu Ile Asn Lys Arg
                65                  70                  75

Lys Glu Tyr Ser Glu Arg Arg Ile Leu Gly Tyr Ser Met Gln Glu
                80                  85                  90

Met Tyr Asp Val Val Ser Gly Val Glu Asp Tyr Lys His Phe Val
                95                  100                 105

Pro Trp Cys Lys Lys Ser Asp Val Ile Ser Lys Arg Ser Gly Tyr
                110                 115                 120

Cys Lys Thr Arg Leu Glu Ile Gly Phe Pro Pro Val Leu Glu Arg
                125                 130                 135

Tyr Thr Ser Val Val Thr Leu Val Lys Pro His Leu Val Lys Ala
                140                 145                 150

Ser Cys Thr Asp Gly Arg Leu Phe Asn His Leu Glu Thr Ile Trp
                155                 160                 165

Cys Phe Ser Pro Gly Leu Pro Gly Tyr Pro Arg Thr Cys Thr Leu
                170                 175                 180

Asp Phe Ser Ile Ser Phe Glu Phe Arg Ser Leu Leu His Ser Gln
                185                 190                 195

Leu Ala Thr Leu Phe Phe Asp Glu Val Val Lys Gln Met Val Ala
                200                 205                 210

Ala Phe Glu Arg Arg Ala Cys Lys Leu Tyr Gly Pro Glu Thr Asn
                215                 220                 225

Ile Pro Arg Glu Leu Met Leu His Glu Val His His Thr
                230                 235

<210> SEQ ID NO 50
<211> LENGTH: 653
<212> TYPE: PRT
<213> ORGANISM: Homo sapiens
<220> FEATURE:
<221> NAME/KEY: misc_feature
<223> OTHER INFORMATION: Incyte ID No: 3511087CD1

<400> SEQUENCE: 50

Met Pro Phe Ser Ala Ser Leu Leu Gly Thr Leu Pro Ile Gly Ala
 1               5                  10                  15

-continued

```
Arg Tyr Ala Pro Pro Ser Phe Ser Glu Phe Tyr Pro Leu
             20                  25                  30

Thr Ser Ser Leu Glu Asp Phe Cys Ser Leu Asn Ser Phe Ser
             35                  40                  45

Met Ser Glu Ser Lys Arg Asp Leu Ser Thr Ser Thr Ser Arg Glu
             50                  55                  60

Gly Thr Pro Leu Asn Asn Ser Asn Ser Ser Leu Leu Met Asn
             65                  70                  75

Gly Pro Gly Ser Leu Phe Ala Ser Glu Asn Phe Leu Gly Ile Ser
             80                  85                  90

Ser Gln Pro Arg Asn Asp Phe Gly Asn Phe Phe Gly Ser Ala Val
             95                 100                 105

Thr Lys Pro Ser Ser Val Thr Pro Arg His Pro Leu Glu Gly
            110                 115                 120

Thr His Glu Leu Arg Gln Ala Cys Gln Ile Cys Phe Val Lys Ser
            125                 130                 135

Gly Pro Lys Leu Met Asp Phe Thr Tyr His Ala Asn Ile Asp His
            140                 145                 150

Lys Cys Lys Lys Asp Ile Leu Ile Gly Arg Ile Lys Asn Val Glu
            155                 160                 165

Asp Lys Ser Trp Lys Lys Ile Arg Pro Arg Pro Thr Lys Thr Asn
            170                 175                 180

Tyr Glu Gly Pro Tyr Tyr Ile Cys Lys Asp Val Ala Ala Glu Glu
            185                 190                 195

Glu Cys Arg Tyr Ser Gly His Cys Thr Phe Ala Tyr Cys Gln Glu
            200                 205                 210

Glu Ile Asp Val Trp Thr Leu Glu Arg Lys Gly Ala Phe Ser Arg
            215                 220                 225

Glu Ala Phe Phe Gly Gly Asn Gly Lys Ile Asn Leu Thr Val Phe
            230                 235                 240

Lys Leu Leu Gln Glu His Leu Gly Glu Phe Ile Phe Leu Cys Glu
            245                 250                 255

Lys Cys Phe Asp His Lys Pro Arg Met Ile Ser Lys Arg Asn Lys
            260                 265                 270

Asp Asn Ser Thr Ala Cys Ser His Pro Val Thr Lys His Glu Phe
            275                 280                 285

Glu Asp Asn Lys Cys Leu Val His Ile Leu Arg Glu Thr Thr Val
            290                 295                 300

Lys Tyr Ser Lys Ile Arg Ser Phe His Gly Gln Cys Gln Leu Asp
            305                 310                 315

Leu Cys Arg His Glu Val Arg Tyr Gly Cys Leu Arg Glu Asp Glu
            320                 325                 330

Cys Phe Tyr Ala His Ser Leu Val Glu Leu Lys Val Trp Ile Met
            335                 340                 345

Gln Asn Glu Thr Gly Ile Ser His Asp Ala Ile Ala Gln Glu Ser
            350                 355                 360

Lys Arg Tyr Trp Gln Asn Leu Glu Ala Asn Val Pro Gly Ala Gln
            365                 370                 375

Val Leu Gly Asn Gln Ile Met Pro Gly Phe Leu Asn Met Lys Ile
            380                 385                 390

Lys Phe Val Cys Ala Gln Cys Leu Arg Asn Gly Gln Val Ile Glu
            395                 400                 405

Pro Asp Lys Asn Arg Lys Tyr Cys Ser Ala Lys Ala Arg His Ser
```

```
                          410                 415                 420
Trp Thr Lys Asp Arg Arg Ala Met Arg Val Met Ser Ile Glu Arg
                    425                 430                 435
Lys Lys Trp Met Asn Ile Arg Pro Leu Pro Thr Lys Lys Gln Met
                    440                 445                 450
Pro Leu Gln Phe Asp Leu Cys Asn His Ile Ala Ser Gly Lys Lys
                    455                 460                 465
Cys Gln Tyr Val Gly Asn Cys Ser Phe Ala His Ser Pro Glu Glu
                    470                 475                 480
Arg Glu Val Trp Thr Tyr Met Lys Glu Asn Gly Ile Gln Asp Met
                    485                 490                 495
Glu Gln Phe Tyr Glu Leu Trp Leu Lys Ser Gln Lys Asn Glu Lys
                    500                 505                 510
Ser Glu Asp Ile Ala Ser Gln Ser Asn Lys Glu Asn Gly Lys Gln
                    515                 520                 525
Ile His Met Pro Thr Asp Tyr Ala Glu Val Thr Val Asp Phe His
                    530                 535                 540
Cys Trp Met Cys Gly Lys Asn Cys Asn Ser Glu Lys Gln Trp Gln
                    545                 550                 555
Gly His Ile Ser Ser Glu Lys His Lys Glu Lys Val Phe His Thr
                    560                 565                 570
Glu Asp Asp Gln Tyr Cys Trp Gln His Arg Phe Pro Thr Gly Tyr
                    575                 580                 585
Phe Ser Ile Cys Asp Arg Tyr Met Asn Gly Thr Cys Pro Glu Gly
                    590                 595                 600
Asn Ser Cys Lys Phe Ala His Gly Asn Ala Glu Leu His Glu Trp
                    605                 610                 615
Glu Glu Arg Arg Asp Ala Leu Lys Met Lys Leu Asn Lys Ala Arg
                    620                 625                 630
Lys Asp His Leu Ile Gly Pro Asn Asp Asn Asp Phe Gly Lys Tyr
                    635                 640                 645
Ser Phe Leu Phe Lys Asp Leu Asn
                    650

<210> SEQ ID NO 51
<211> LENGTH: 112
<212> TYPE: PRT
<213> ORGANISM: Homo sapiens
<220> FEATURE:
<221> NAME/KEY: misc_feature
<223> OTHER INFORMATION: Incyte ID No: 1968009CD1

<400> SEQUENCE: 51

Met Gln Asp Thr Gly Ser Val Val Pro Leu His Trp Phe Gly Phe
  1               5                  10                  15
Gly Tyr Ala Ala Leu Val Ala Ser Gly Ile Ile Gly Tyr Val
                   20                  25                  30
Lys Ala Gly Ser Val Pro Ser Leu Ala Ala Gly Leu Leu Phe Gly
                   35                  40                  45
Ser Leu Ala Gly Leu Gly Ala Tyr Gln Leu Ser Gln Asp Pro Arg
                   50                  55                  60
Asn Val Trp Val Phe Leu Ala Thr Ser Gly Thr Leu Ala Gly Ile
                   65                  70                  75
Met Gly Met Arg Phe Tyr His Ser Gly Lys Phe Met Pro Ala Gly
                   80                  85                  90
```

```
Leu Ile Ala Gly Ala Ser Leu Leu Met Val Ala Lys Val Gly Val
                95                 100                 105

Ser Met Phe Asn Arg Pro His
                110

<210> SEQ ID NO 52
<211> LENGTH: 114
<212> TYPE: PRT
<213> ORGANISM: Homo sapiens
<220> FEATURE:
<221> NAME/KEY: misc_feature
<223> OTHER INFORMATION: Incyte ID No: 1923127CD1

<400> SEQUENCE: 52

Met Glu Lys Pro Leu Phe Pro Leu Val Pro Leu His Trp Phe Gly
  1               5                  10                  15

Phe Gly Tyr Thr Ala Leu Val Val Ser Gly Gly Ile Val Gly Tyr
                20                  25                  30

Val Lys Thr Gly Ser Val Pro Ser Leu Ala Ala Gly Leu Leu Phe
                35                  40                  45

Gly Ser Leu Ala Gly Leu Gly Ala Tyr Gln Leu Tyr Gln Asp Pro
                50                  55                  60

Arg Asn Val Trp Gly Phe Leu Ala Ala Thr Ser Val Thr Phe Val
                65                  70                  75

Gly Val Met Gly Met Arg Ser Tyr Tyr Tyr Gly Lys Phe Met Pro
                80                  85                  90

Val Gly Leu Ile Ala Gly Ala Ser Leu Leu Met Ala Ala Lys Val
                95                 100                 105

Gly Val Arg Met Leu Met Thr Ser Asp
                110

<210> SEQ ID NO 53
<211> LENGTH: 114
<212> TYPE: PRT
<213> ORGANISM: Homo sapiens
<220> FEATURE:
<221> NAME/KEY: misc_feature
<223> OTHER INFORMATION: Incyte ID No: 3123954CD1

<400> SEQUENCE: 53

Met Ala Ala Ile Pro Ser Ser Gly Ser Leu Val Ala Thr His Asp
  1               5                  10                  15

Tyr Tyr Arg Arg Leu Gly Ser Thr Ser Asn Ser Ser Cys
                20                  25                  30

Ser Ser Thr Glu Cys Pro Gly Glu Ala Ile Pro His Pro Pro Gly
                35                  40                  45

Leu Pro Lys Ala Asp Pro Gly His Trp Trp Ala Ser Phe Phe Phe
                50                  55                  60

Gly Lys Ser Thr Leu Pro Phe Met Ala Thr Val Leu Glu Ser Ala
                65                  70                  75

Glu His Ser Glu Pro Pro Gln Ala Ser Ser Met Thr Ala Cys
                80                  85                  90

Gly Leu Ala Arg Asp Ala Pro Arg Lys Gln Pro Gly Gly Gln Ser
                95                 100                 105

Ser Thr Ala Ser Ala Gly Pro Pro Ser
                110

<210> SEQ ID NO 54
<211> LENGTH: 291
```

-continued

```
<212> TYPE: PRT
<213> ORGANISM: Homo sapiens
<220> FEATURE:
<221> NAME/KEY: misc_feature
<223> OTHER INFORMATION: Incyte ID No: 1321844CD1

<400> SEQUENCE: 54
```

| Met | Ser | Gln | Glu | Gly | Val | Glu | Leu | Glu | Lys | Ser | Val | Arg | Gly | Leu |
|---|---|---|---|---|---|---|---|---|---|---|---|---|---|---|
| 1 | | | | 5 | | | | | 10 | | | | | 15 |

| Arg | Glu | Lys | Phe | His | Gly | Lys | Val | Ser | Lys | Lys | Ala | Gly | Ala |
|---|---|---|---|---|---|---|---|---|---|---|---|---|---|
| | | | 20 | | | | | 25 | | | | | 30 |

| Leu | Met | Arg | Lys | Phe | Gly | Ser | Asp | His | Thr | Gly | Val | Gly | Arg | Ser |
|---|---|---|---|---|---|---|---|---|---|---|---|---|---|---|
| | | | 35 | | | | | 40 | | | | | | 45 |

| Ile | Val | Tyr | Gly | Val | Lys | Gln | Lys | Asp | Gly | Gln | Glu | Leu | Ser | Asn |
|---|---|---|---|---|---|---|---|---|---|---|---|---|---|---|
| | | | 50 | | | | | 55 | | | | | | 60 |

| Asp | Leu | Asp | Ala | Gln | Asp | Pro | Pro | Glu | Asp | Met | Lys | Gln | Asp | Arg |
|---|---|---|---|---|---|---|---|---|---|---|---|---|---|---|
| | | | | 65 | | | | 70 | | | | | | 75 |

| Asp | Ile | Gln | Ala | Val | Ala | Thr | Ser | Leu | Leu | Pro | Leu | Thr | Glu | Ala |
|---|---|---|---|---|---|---|---|---|---|---|---|---|---|---|
| | | | | 80 | | | | 85 | | | | | | 90 |

| Asn | Leu | Arg | Met | Phe | Gln | Arg | Ala | Gln | Asp | Leu | Ile | Pro | Ala |
|---|---|---|---|---|---|---|---|---|---|---|---|---|---|
| | | | 95 | | | | | 100 | | | | | 105 |

| Val | Asp | Arg | Gln | Phe | Ala | Cys | Ser | Ser | Cys | Asp | His | Val | Trp | Trp |
|---|---|---|---|---|---|---|---|---|---|---|---|---|---|---|
| | | | | 110 | | | | 115 | | | | | | 120 |

| Arg | Arg | Val | Pro | Gln | Arg | Lys | Glu | Val | Ser | Arg | Cys | Arg | Lys | Cys |
|---|---|---|---|---|---|---|---|---|---|---|---|---|---|---|
| | | | | 125 | | | | 130 | | | | | | 135 |

| Arg | Lys | Arg | Tyr | Glu | Pro | Val | Pro | Ala | Asp | Lys | Met | Trp | Gly | Leu |
|---|---|---|---|---|---|---|---|---|---|---|---|---|---|---|
| | | | | 140 | | | | 145 | | | | | | 150 |

| Ala | Glu | Phe | His | Cys | Pro | Lys | Cys | Arg | His | Asn | Phe | Arg | Gly | Trp |
|---|---|---|---|---|---|---|---|---|---|---|---|---|---|---|
| | | | | 155 | | | | 160 | | | | | | 165 |

| Ala | Gln | Met | Gly | Ser | Pro | Ser | Pro | Cys | Tyr | Gly | Cys | Gly | Phe | Pro |
|---|---|---|---|---|---|---|---|---|---|---|---|---|---|---|
| | | | | 170 | | | | 175 | | | | | | 180 |

| Val | Tyr | Pro | Thr | Arg | Ile | Leu | Pro | Pro | Arg | Trp | Asp | Arg | Asp | Pro |
|---|---|---|---|---|---|---|---|---|---|---|---|---|---|---|
| | | | | 185 | | | | 190 | | | | | | 195 |

| Asp | Arg | Arg | Ser | Thr | His | Thr | His | Ser | Cys | Ser | Ala | Ala | Asp | Cys |
|---|---|---|---|---|---|---|---|---|---|---|---|---|---|---|
| | | | | 200 | | | | 205 | | | | | | 210 |

| Tyr | Asn | Arg | Arg | Glu | Pro | His | Val | Pro | Gly | Thr | Ser | Cys | Ala | His |
|---|---|---|---|---|---|---|---|---|---|---|---|---|---|---|
| | | | | 215 | | | | 220 | | | | | | 225 |

| Pro | Lys | Ser | Arg | Lys | Gln | Asn | His | Leu | Pro | Lys | Val | Leu | His | Pro |
|---|---|---|---|---|---|---|---|---|---|---|---|---|---|---|
| | | | | 230 | | | | 235 | | | | | | 240 |

| Ser | Asn | Pro | His | Ile | Ser | Ser | Gly | Ser | Thr | Val | Ala | Thr | Cys | Leu |
|---|---|---|---|---|---|---|---|---|---|---|---|---|---|---|
| | | | | 245 | | | | 250 | | | | | | 255 |

| Ser | Gln | Gly | Gly | Leu | Leu | Glu | Asp | Leu | Asp | Asn | Leu | Ile | Leu | Glu |
|---|---|---|---|---|---|---|---|---|---|---|---|---|---|---|
| | | | | 260 | | | | 265 | | | | | | 270 |

| Asp | Leu | Lys | Glu | Glu | Glu | Glu | Glu | Glu | Glu | Val | Glu | Asp | Glu |
|---|---|---|---|---|---|---|---|---|---|---|---|---|---|
| | | | 275 | | | | | 280 | | | | | 285 |

| Glu | Gly | Gly | Pro | Arg | Glu |
|---|---|---|---|---|---|
| | | | 290 | | |

```
<210> SEQ ID NO 55
<211> LENGTH: 610
<212> TYPE: PRT
<213> ORGANISM: Homo sapiens
<220> FEATURE:
<221> NAME/KEY: misc_feature
<223> OTHER INFORMATION: Incyte ID No: 1867333CD1

<400> SEQUENCE: 55
```

```
Met Trp Leu Pro Leu Val Leu Leu Leu Ala Val Leu Leu Ala
 1               5                  10                  15

Val Leu Cys Lys Val Tyr Leu Gly Leu Phe Ser Gly Ser Ser Pro
                20                  25                  30

Asn Pro Phe Ser Glu Asp Val Lys Arg Pro Ala Pro Leu Val
                35                  40                  45

Thr Asp Lys Glu Ala Arg Lys Lys Val Leu Lys Gln Ala Phe Ser
                50                  55                  60

Ala Asn Gln Val Pro Glu Lys Leu Asp Val Val Ile Gly Ser
                65                  70                  75

Gly Phe Gly Gly Leu Ala Ala Ala Ala Ile Leu Ala Lys Ala Gly
                80                  85                  90

Lys Arg Val Leu Val Leu Glu Gln His Thr Lys Ala Gly Gly Cys
                95                  100                 105

Cys His Thr Phe Gly Lys Asn Gly Leu Glu Phe Asp Thr Gly Ile
                110                 115                 120

His Tyr Ile Gly Arg Met Glu Glu Gly Ser Ile Gly Arg Phe Ile
                125                 130                 135

Leu Asp Gln Ile Thr Glu Gly Gln Leu Asp Trp Ala Pro Leu Ser
                140                 145                 150

Ser Pro Phe Asp Ile Met Val Leu Glu Gly Pro Asn Gly Arg Lys
                155                 160                 165

Glu Tyr Pro Met Tyr Ser Gly Glu Lys Ala Tyr Ile Gln Gly Leu
                170                 175                 180

Lys Glu Lys Phe Pro Gln Glu Glu Ala Ile Ile Asp Lys Tyr Ile
                185                 190                 195

Lys Leu Val Lys Val Val Ser Ser Gly Ala Pro His Ala Ile Leu
                200                 205                 210

Leu Lys Phe Leu Pro Leu Pro Val Val Gln Leu Leu Asp Arg Cys
                215                 220                 225

Gly Leu Leu Thr Arg Phe Ser Pro Phe Leu Gln Ala Ser Thr Gln
                230                 235                 240

Ser Leu Ala Glu Val Leu Gln Gln Leu Gly Ala Ser Ser Glu Leu
                245                 250                 255

Gln Ala Val Leu Ser Tyr Ile Phe Pro Thr Tyr Gly Val Thr Pro
                260                 265                 270

Asn His Ser Ala Phe Ser Met His Ala Leu Leu Val Asn His Tyr
                275                 280                 285

Met Lys Gly Gly Phe Tyr Pro Arg Gly Gly Ser Ser Glu Ile Ala
                290                 295                 300

Phe His Thr Ile Pro Val Ile Gln Arg Ala Gly Gly Ala Val Leu
                305                 310                 315

Thr Lys Ala Thr Val Gln Ser Val Leu Leu Asp Ser Ala Gly Lys
                320                 325                 330

Ala Cys Gly Val Ser Val Lys Lys Gly His Glu Leu Val Asn Ile
                335                 340                 345

Tyr Cys Pro Ile Val Val Ser Asn Ala Gly Leu Phe Asn Thr Tyr
                350                 355                 360

Glu His Leu Leu Pro Gly Asn Ala Arg Cys Leu Pro Gly Val Lys
                365                 370                 375

Gln Gln Leu Gly Thr Val Arg Pro Gly Leu Gly Met Thr Ser Val
                380                 385                 390

Phe Ile Cys Leu Arg Gly Thr Lys Glu Asp Leu His Leu Pro Ser
```

-continued

```
                395                 400                 405
Thr Asn Tyr Tyr Val Tyr Asp Thr Asp Met Asp Gln Ala Met
                410                 415                 420
Glu Arg Tyr Val Ser Met Pro Arg Glu Glu Ala Ala Glu His Ile
                425                 430                 435
Pro Leu Leu Phe Phe Ala Phe Pro Ser Ala Lys Asp Pro Thr Trp
                440                 445                 450
Glu Asp Arg Phe Pro Gly Arg Ser Thr Met Ile Met Leu Ile Pro
                455                 460                 465
Thr Ala Tyr Glu Trp Phe Glu Trp Gln Ala Glu Leu Lys Gly
                470                 475                 480
Lys Arg Gly Ser Asp Tyr Glu Thr Phe Lys Asn Ser Phe Val Glu
                485                 490                 495
Ala Ser Met Ser Val Val Leu Lys Leu Phe Pro Gln Leu Glu Gly
                500                 505                 510
Lys Val Glu Ser Val Thr Ala Gly Ser Pro Leu Thr Asn Gln Phe
                515                 520                 525
Tyr Leu Ala Ala Pro Arg Gly Ala Cys Tyr Gly Ala Asp His Asp
                530                 535                 540
Leu Gly Arg Leu His Pro Cys Val Met Ala Ser Leu Arg Ala Gln
                545                 550                 555
Ser Pro Ile Pro Asn Leu Tyr Leu Thr Gly Gln Asp Ile Phe Thr
                560                 565                 570
Cys Gly Leu Val Gly Ala Leu Gln Gly Ala Leu Leu Cys Ser Ser
                575                 580                 585
Ala Ile Leu Lys Arg Asn Leu Tyr Ser Asp Leu Lys Asn Leu Asp
                590                 595                 600
Ser Arg Ile Arg Ala Gln Lys Lys Lys Asn
                605                 610

<210> SEQ ID NO 56
<211> LENGTH: 352
<212> TYPE: PRT
<213> ORGANISM: Homo sapiens
<220> FEATURE:
<221> NAME/KEY: misc_feature
<223> OTHER INFORMATION: Incyte ID No: 1461451CD1

<400> SEQUENCE: 56

Pro Arg Val Arg Gly Arg Trp Val Ala His Ala Ser Ala His Ala
 1               5                  10                  15
Ser Ala His Ala Ser Asp Glu Ile Pro Ala Ser Gly Trp Thr Gln
                20                  25                  30
Trp Phe Cys Thr Glu Ala Leu Val Met Val Ala Pro Val Trp Tyr
                35                  40                  45
Leu Val Ala Ala Leu Leu Val Gly Phe Ile Leu Phe Leu Thr
                50                  55                  60
Arg Ser Arg Gly Arg Ala Ala Ser Ala Gly Gln Glu Pro Leu His
                65                  70                  75
Asn Glu Glu Leu Ala Gly Ala Gly Arg Val Ala Gln Pro Gly Pro
                80                  85                  90
Leu Glu Pro Glu Glu Pro Arg Ala Gly Arg Pro Arg Arg
                95                  100                 105
Arg Asp Leu Gly Ser Arg Leu Gln Ala Gln Arg Ala Gln Arg
                110                 115                 120
```

-continued

```
Val Ala Trp Ala Glu Ala Asp Glu Asn Glu Glu Ala Val Ile
            125                 130                 135

Leu Ala Gln Glu Glu Gly Val Glu Lys Pro Ala Glu Thr His
            140                 145                 150

Leu Ser Gly Lys Ile Gly Ala Lys Lys Leu Arg Lys Leu Glu
            155                 160                 165

Lys Gln Ala Arg Lys Ala Gln Arg Glu Ala Glu Ala Glu Arg
            170                 175                 180

Glu Glu Arg Lys Arg Leu Glu Ser Gln Arg Glu Ala Glu Trp Lys
            185                 190                 195

Lys Glu Glu Glu Arg Leu Arg Leu Glu Glu Gln Lys Glu Glu
            200                 205                 210

Glu Glu Arg Lys Ala Arg Glu Gln Ala Gln Arg Glu His Glu
            215                 220                 225

Glu Tyr Leu Lys Leu Lys Glu Ala Phe Val Val Glu Glu Gly
            230                 235                 240

Val Gly Glu Thr Met Thr Glu Glu Gln Ser Gln Ser Phe Leu Thr
            245                 250                 255

Glu Phe Ile Asn Tyr Ile Lys Gln Ser Lys Val Val Leu Leu Glu
            260                 265                 270

Asp Leu Ala Ser Gln Val Gly Leu Arg Thr Gln Asp Thr Ile Asn
            275                 280                 285

Arg Ile Gln Asp Leu Leu Ala Glu Gly Thr Ile Thr Gly Val Ile
            290                 295                 300

Asp Asp Arg Gly Lys Phe Ile Tyr Ile Thr Pro Glu Glu Leu Ala
            305                 310                 315

Ala Val Ala Asn Phe Ile Arg Gln Arg Gly Arg Val Ser Ile Ala
            320                 325                 330

Glu Leu Ala Gln Ala Ser Asn Ser Leu Ile Ala Trp Gly Arg Glu
            335                 340                 345

Ser Pro Ala Gln Ala Pro Ala
            350

<210> SEQ ID NO 57
<211> LENGTH: 216
<212> TYPE: PRT
<213> ORGANISM: Homo sapiens
<220> FEATURE:
<221> NAME/KEY: misc_feature
<223> OTHER INFORMATION: Incyte ID No: 2345712CD1

<400> SEQUENCE: 57

Tyr Asp Pro Ile Gly Phe Gly Leu Ser Trp Glu Ala Gly Arg Ile
  1               5                  10                  15

Ile Gly Trp Gly Lys Pro Thr Arg Gly Arg Gly Arg Gly Ser
             20                  25                  30

Leu Ser Thr Arg Gly Arg Gly Ser Glu Val Pro Asp Ser Ala His
             35                  40                  45

Leu Ala Pro Thr Pro Leu Phe Ser Glu Ser Gly Cys Cys Gly Leu
             50                  55                  60

Arg Ser Arg Phe Leu Thr Asp Cys Lys Met Glu Glu Gly Gly Asn
             65                  70                  75

Leu Gly Gly Leu Ile Lys Met Val His Leu Leu Val Leu Ser Gly
             80                  85                  90

Ala Trp Gly Met Gln Met Trp Val Thr Phe Val Ser Gly Phe Leu
             95                 100                 105
```

```
Leu Phe Arg Ser Leu Pro Arg His Thr Phe Gly Leu Val Gln Ser
                110                 115                 120

Lys Leu Phe Pro Phe Tyr Phe His Ile Ser Met Gly Cys Ala Phe
                125                 130                 135

Ile Asn Leu Cys Ile Leu Ala Ser Gln His Ala Trp Ala Gln Leu
                140                 145                 150

Thr Phe Trp Glu Ala Ser Gln Leu Tyr Leu Leu Phe Leu Ser Leu
                155                 160                 165

Thr Leu Ala Thr Val Asn Ala Arg Trp Leu Glu Pro Arg Thr Thr
                170                 175                 180

Ala Ala Met Trp Ala Leu Gln Thr Val Glu Lys Glu Arg Gly Leu
                185                 190                 195

Gly Gly Glu Val Pro Gly Ser His Gln Gly Ser Asp Pro Tyr Arg
                200                 205                 210

Gln Leu Arg Glu Lys Asp
                215

<210> SEQ ID NO 58
<211> LENGTH: 292
<212> TYPE: PRT
<213> ORGANISM: Homo sapiens
<220> FEATURE:
<221> NAME/KEY: misc_feature
<223> OTHER INFORMATION: Incyte ID No: 1810320CD1

<400> SEQUENCE: 58

Met Ala Gln Pro Pro Asp Val Glu Gly Asp Cys Leu Pro
  1               5                  10                  15

Ala Tyr Arg His Leu Phe Cys Pro Asp Leu Arg Asp Lys Val
                 20                  25                  30

Ala Phe Ile Thr Gly Gly Gly Ser Gly Ile Gly Phe Arg Ile Ala
                 35                  40                  45

Glu Ile Phe Met Arg His Gly Cys His Thr Val Ile Ala Ser Arg
                 50                  55                  60

Ser Leu Pro Arg Val Leu Thr Ala Ala Arg Lys Leu Ala Gly Ala
                 65                  70                  75

Thr Gly Arg Arg Cys Leu Pro Leu Ser Met Asp Val Arg Ala Pro
                 80                  85                  90

Pro Ala Val Met Ala Ala Val Asp Gln Ala Leu Lys Glu Phe Gly
                 95                 100                 105

Arg Ile Asp Ile Leu Ile Asn Cys Ala Ala Gly Asn Phe Leu Cys
                110                 115                 120

Pro Ala Gly Ala Leu Ser Phe Asn Ala Phe Lys Thr Val Met Asp
                125                 130                 135

Ile Asp Thr Ser Gly Thr Phe Asn Val Ser Arg Val Leu Tyr Glu
                140                 145                 150

Lys Phe Phe Arg Asp His Gly Gly Val Ile Val Asn Ile Thr Ala
                155                 160                 165

Thr Leu Gly Asn Arg Gly Gln Ala Leu Gln Val His Ala Gly Ser
                170                 175                 180

Ala Lys Ala Ala Val Asp Ala Met Thr Arg His Leu Ala Val Glu
                185                 190                 195

Trp Gly Pro Gln Asn Ile Arg Val Asn Ser Leu Ala Pro Gly Pro
                200                 205                 210

Ile Ser Gly Thr Glu Gly Leu Arg Arg Leu Gly Gly Pro Gln Ala
```

-continued

```
                    215                 220                 225
Ser Leu Ser Thr Lys Val Thr Ala Ser Pro Leu Gln Arg Leu Gly
                230                 235                 240

Asn Lys Thr Glu Ile Ala His Ser Val Leu Tyr Leu Ala Ser Pro
                245                 250                 255

Leu Ala Ser Tyr Val Thr Gly Ala Val Leu Val Ala Asp Gly Gly
                260                 265                 270

Ala Trp Leu Thr Phe Pro Asn Gly Val Lys Gly Leu Pro Asp Phe
                275                 280                 285

Ala Ser Phe Ser Ala Lys Leu
                290

<210> SEQ ID NO 59
<211> LENGTH: 158
<212> TYPE: PRT
<213> ORGANISM: Homo sapiens
<220> FEATURE:
<221> NAME/KEY: misc_feature
<223> OTHER INFORMATION: Incyte ID No: 964996CD1

<400> SEQUENCE: 59

Glu Gly Gly Pro Ser Trp Thr Arg Glu Arg Thr Leu Val Ala Val
  1               5                  10                  15

Lys Pro Asp Gly Val Gln Arg Arg Leu Val Gly Asp Val Ile Gln
                 20                  25                  30

Arg Phe Glu Arg Arg Gly Phe Thr Leu Val Gly Met Lys Met Leu
                 35                  40                  45

Gln Ala Pro Glu Ser Val Leu Ala Glu His Tyr Gln Asp Leu Arg
                 50                  55                  60

Arg Lys Pro Phe Tyr Pro Ala Leu Ile Arg Tyr Met Ser Ser Gly
             65                  70                  75

Pro Val Val Ala Met Val Trp Glu Gly Tyr Asn Val Val Arg Ala
                 80                  85                  90

Ser Arg Ala Met Ile Gly His Thr Asp Ser Ala Glu Ala Ala Pro
                 95                 100                 105

Gly Thr Ile Arg Gly Tyr Phe Ser Val His Ile Ser Arg Asn Val
                110                 115                 120

Ile His Ala Ser Asp Ser Val Glu Gly Ala Gln Arg Glu Ile Gln
                125                 130                 135

Leu Trp Phe Gln Ser Ser Glu Leu Val Ser Trp Ala Asp Gly Gly
                140                 145                 150

Gln His Ser Ser Ile His Pro Ala
                155

<210> SEQ ID NO 60
<211> LENGTH: 559
<212> TYPE: DNA
<213> ORGANISM: Rattus norvegicus
<220> FEATURE:
<221> NAME/KEY: misc_feature
<223> OTHER INFORMATION: Incyte ID No: 701884305H1

<400> SEQUENCE: 60
ggaaacctaa acgcgcgtgc gcttcttcca cgccacggaa accgtgcagg cctggtgtgg      60
tctccaaagt gactgaacaa tgcagaagga cagtggccca ctggttcctt tacattatta    120
tggtttcggc tatgcggccc tggtggctac tggtgggatt attggctatg caaaagcagg    180
tagtgtgccg tccctggctg ctggactctt ctttgggggc ctggcaggcc tgggtgccta    240
```

```
ccagctgtct caggacccca ggaacgtgtg ggttttccta gctacgtctg ggactttggc      300
tggcattatg gggatgagat tctacaactc tgggaaattt atgcctgcag gtttgatcgc      360
gggagccagt ttgctgatgg ttgccaaact tggacttagt atgttgagtt caccccatcc      420
gtagtagcca tagtcctgcg tgggctcatg atgagttgac actctccagt cctccacatt      480
accacgctga agagataaga acagcaaaga cctacactga gcacatggag gcgaagacgt      540
ggttactata gtgaccgtc                                                  559
```

<210> SEQ ID NO 61
<211> LENGTH: 326
<212> TYPE: DNA
<213> ORGANISM: Rattus norvegicus
<220> FEATURE:
<221> NAME/KEY: misc_feature
<223> OTHER INFORMATION: Incyte ID No: 701607951H1

<400> SEQUENCE: 61

```
gtgttgggtg tgttcttact ttgcggattt taccaccctg gaattgttcc gtacgcgcag      60
gcgcgcgggc gctctcccgt gcactctctg ctgagctagc ggactgcccg cctctctaaa     120
acgtcctgta actgcggttc cgggagtgga aacctaaacg cgcgtgcgct tcttccacgc     180
cacggaaacc gtgcaggcct ggtgtggtct ccaaagtgac tgaacaatgc agaaggacag     240 tgcccactg gttcctttac attattatgg tttcggctat gcggccctgg tggctactgg     300
tgggattatt ggctatgcaa aagcag                                         326
```

<210> SEQ ID NO 62
<211> LENGTH: 333
<212> TYPE: DNA
<213> ORGANISM: Rattus norvegicus
<220> FEATURE:
<221> NAME/KEY: misc_feature
<223> OTHER INFORMATION: Incyte ID No: 701644253H1
<220> FEATURE:
<221> NAME/KEY: unsure
<222> LOCATION: 84, 97, 135, 317
<223> OTHER INFORMATION: a, t, c, g, or other

<400> SEQUENCE: 62

```
aacgtcctgt aactgcggtt ccgggagtgg aaacctaaac gcgcgtgcgc tttcttccac      60
gccacggaaa accgtgcagg cctngtgtgg tctccanagt gactgaacaa tgcagaagga     120
cagtggccca ctggntcctt tacattatta tggtttcggc tatgcggccc tggtggctac     180
tggtgggatt attggctatg caaaagcagg tagtgtgccg tccctggctg ctggactctt     240 ctttggggc ctggcaggcc tggtgcctta ccagctgtct caggacccca ggaacgtgtg     300
ggttttccta gctacgnctg ggactttggc tgg                                 333
```

<210> SEQ ID NO 63
<211> LENGTH: 318
<212> TYPE: DNA
<213> ORGANISM: Rattus norvegicus
<220> FEATURE:
<221> NAME/KEY: misc_feature
<223> OTHER INFORMATION: Incyte ID No: 701513151H1
<220> FEATURE:
<221> NAME/KEY: unsure
<222> LOCATION: 46, 48
<223> OTHER INFORMATION: a, t, c, g, or other

<400> SEQUENCE: 63

```
cttactttgc ggattttacc accctggaat tgttccgtac gcgcangngc gcggggctct      60
```

```
cccgtgcact ctctgctgag ctagcggact gcccgcctct ctaaaacgtc ctgtaactgc    120
ggttccggga gtggaaacct aaacgcgcgt gcgcttcttc cacgccacgg aaaccgtgca    180
ggcctggtgt ggtctccaaa gtgactgaac aatgcagaag gacagtggcc cactggttcc    240
tttacattat tatggtttcg gctatgcggc cctggtggct actggtggga ttattggcta    300
tgcaaaagca ggtagtgt                                                 318
```

<210> SEQ ID NO 64
<211> LENGTH: 315
<212> TYPE: DNA
<213> ORGANISM: Rattus norvegicus
<220> FEATURE:
<221> NAME/KEY: misc_feature
<223> OTHER INFORMATION: Incyte ID No: 701652337H1
<220> FEATURE:
<221> NAME/KEY: unsure
<222> LOCATION: 5, 38
<223> OTHER INFORMATION: a, t, c, g, or other

<400> SEQUENCE: 64

```
cagcncaggc ctccgggctc cagctccggt gttgggtnca ggcctggtgt ggtctccaaa     60
gtgactgaac aatgcagaag gacagtggcc cactggttcc tttacattat tatggtttcg    120
gctatgcggc cctggtggct actggtggga ttattggcta tgcaaaagca ggtagtgtgc    180
cgtccctggc tgctggactc ttctttgggg gcctggcagg cctgggtgcc taccagctgt    240
ctcaggaccc caggaacgtg tgggttttcc tagctacgtc tgggactttg gctggcatat    300
ggggatgaga ttcta                                                    315
```

<210> SEQ ID NO 65
<211> LENGTH: 313
<212> TYPE: DNA
<213> ORGANISM: Rattus norvegicus
<220> FEATURE:
<221> NAME/KEY: misc_feature
<223> OTHER INFORMATION: Incyte ID No: 701562183H1
<220> FEATURE:
<221> NAME/KEY: unsure
<222> LOCATION: 307
<223> OTHER INFORMATION: a, t, c, g, or other

<400> SEQUENCE: 65

```
ggtctccaaa gtgactgaac aatgcagaag gacagtggcc cactggttcc tttacattat     60
tatggtttcg gctatgcggc cctggtggct actggtggga ttattggcta tgcaaaagca    120
ggtagtgtgc cgtccctggc tgctggactc ttctttgggg gcctggcagg cctgggtgcc    180
taccagctgt ctcaggaccc caggaacgtg tgggttttcc tagctacgtc tgggactttg    240
gctggcatta tggggatgag attctacaac tctgggaaat ttatgcctgc aggtttgatc    300
gcgggancat ttt                                                      313
```

<210> SEQ ID NO 66
<211> LENGTH: 304
<212> TYPE: DNA
<213> ORGANISM: Rattus norvegicus
<220> FEATURE:
<221> NAME/KEY: misc_feature
<223> OTHER INFORMATION: Incyte ID No: 700227356H1

<400> SEQUENCE: 66

```
cgccgtcgtc ctccagcgca ggcctccggg ctccagctcc ggtgttgggt gcaggcctgg     60
tgtggtctcc aaagtgactg aacaatgcag aaggacagtg gcccactggt tcctttacat    120
```

```
tattatggtt tcggctatgc ggccctggtg gctactggtg ggattattgg ctatgcaaaa    180
gcaggtagtg tgccgtccct ggctgctgga ctcttctttg ggggcctggc aggcctgggt    240
gcctaccagc tgtctcagga ccccaggaac gtgtgggttt cctagctac gtctgggact    300 ttgg                                                                 304
```

<210> SEQ ID NO 67
<211> LENGTH: 327
<212> TYPE: DNA
<213> ORGANISM: Rattus norvegicus
<220> FEATURE:
<221> NAME/KEY: misc_feature
<223> OTHER INFORMATION: Incyte ID No: 701649802H1
<220> FEATURE:
<221> NAME/KEY: unsure
<222> LOCATION: 133
<223> OTHER INFORMATION: a, t, c, g, or other

<400> SEQUENCE: 67

```
ctccggtgtt gggtgcaggc ctggtgtggt ctccaaagtg actgaacaat gcagaaggac     60
agtggaccac tggttcctta cattattatg gtttcggcta tgcggccctg gtggctactg    120
gtgggattat tgncttttgca aaagcaggta gtgtgccgtc cctggctgtt ggactcttct    180
ttgggggcct ggcaggcctg ggtgcctacc agctgtctca ggaccccagg aacgtgtggg    240
ttttcctagc tacgtctggg actttggctg gcattatggg gatgagattc tacaactctg    300
ggaaatttat gcctgcagtt tgatcgc                                        327
```

<210> SEQ ID NO 68
<211> LENGTH: 305
<212> TYPE: DNA
<213> ORGANISM: Rattus norvegicus
<220> FEATURE:
<221> NAME/KEY: misc_feature
<223> OTHER INFORMATION: Incyte ID No: 700226414H1
<220> FEATURE:
<221> NAME/KEY: unsure
<222> LOCATION: 17
<223> OTHER INFORMATION: a, t, c, g, or other

<400> SEQUENCE: 68

```
gccgtcgtcc tccagcncag gcctccgggc tccagctccg gtgttgggtg caggcctggt     60
gtggtctcca aagtgactga acaatgcaga aggacagtgg cccactggtt cctttacatt    120
attatggttt cggctatgcg gccctggtgg ctactggtgg gattattggc tatgcaaaag    180
caggtagtgt gccgtccctg gctgctggac tcttctttgg ggcctggca ggcctgggtg    240 cctaccagct gtctcaggac cccaggaagt gtgggttttc tagctacgt ctgggacttg    300 gctgg                                                                305
```

<210> SEQ ID NO 69
<211> LENGTH: 295
<212> TYPE: DNA
<213> ORGANISM: Rattus norvegicus
<220> FEATURE:
<221> NAME/KEY: misc_feature
<223> OTHER INFORMATION: Incyte ID No: 700275094H1
<220> FEATURE:
<221> NAME/KEY: unsure
<222> LOCATION: 10, 16
<223> OTHER INFORMATION: a, t, c, g, or other

<400> SEQUENCE: 69

```
tcctccagcn caggcntccg ggctccagct ccggtgttgg gtgcaggcct ggtgtggtct     60
```

```
ccaaagtgac tgaacaatgc agaaggacag tggcccactg gttcctttac attattatgg    120
tttcggctat gcggccctgg tggctactgg tgggattatt ggctatgcaa aagcaggtag    180
tgtgccgtcc ctggctgctg gactcttctt tgggggcct ggcaggcctg ggtgcctacc    240
agctgtctca ggaccccagg aacgtgtggg ttttcctagc tacgtctggg atttg         295
```

<210> SEQ ID NO 70
<211> LENGTH: 301
<212> TYPE: DNA
<213> ORGANISM: Rattus norvegicus
<220> FEATURE:
<221> NAME/KEY: misc_feature
<223> OTHER INFORMATION: Incyte ID No: 700226425H1

<400> SEQUENCE: 70

```
cctgacctct gttcctgtgc tcccgccgtc gtcctccagc gcaggcctcc gggctccagc    60
tccggtgttg ggtgcaggcc tggtgtggtc tccaaagtga ctgaacaatg cagaaggaca    120
gtggcccact ggttcccttta cattattatg gtttcggcta tgcggccctg gtggctactg    180
gtgggattat tggctatgca aaagcaggta gtgtgccgtc cctggctgct ggactcttct    240
ttgggggcct ggcaggcctg ggtgcctacc agctgtctca ggaccccagg aacgtgtggg    300
t                                                                   301
```

<210> SEQ ID NO 71
<211> LENGTH: 282
<212> TYPE: DNA
<213> ORGANISM: Rattus norvegicus
<220> FEATURE:
<221> NAME/KEY: misc_feature
<223> OTHER INFORMATION: Incyte ID No: 700275207H1

<400> SEQUENCE: 71

```
tcctccagcg caggcctccg ggctccagct ccggtgttgg gtgcaggcct ggtgtggtct    60
ccaaagtgac tgaacaatgc agaaggacag tggcccactg gttcctttac attattatgg    120
tttcggctat gcggccctgg tggctactgg tgggattatt ggctatgcaa aagcaggtag    180
tgtgccgtcc ctggctgctg gactcttctt tgggggcctg gcaggcctgg gtgcctacca    240
gctgtctcag gaccccagga acgtgtgggt tttcctagct ac                      282
```

<210> SEQ ID NO 72
<211> LENGTH: 282
<212> TYPE: DNA
<213> ORGANISM: Rattus norvegicus
<220> FEATURE:
<221> NAME/KEY: misc_feature
<223> OTHER INFORMATION: Incyte ID No: 701507568H1

<400> SEQUENCE: 72

```
cgccgtcgtc ctccagcgca ggcctccggg ctccagctcc ggtgttgggt gcaggcctgg    60
tgtggtctcc aaagtgactg aacaatgcag aaggacagtg gcccactggt tcctttacat    120
tattatggtt tcggctatgc ggccctggtg ctactggtg gattattgg ctatgcaaaa    180 gcaggtagtg tgccgtccct ggctgctgga ctcttctttg ggggcctggc aggcctgggt    240
gcctaccagc tgtctcagga ccccaggaac gtgtgggttt tc                      282
```

<210> SEQ ID NO 73
<211> LENGTH: 281
<212> TYPE: DNA
<213> ORGANISM: Rattus norvegicus

```
<220> FEATURE:
<221> NAME/KEY: misc_feature
<223> OTHER INFORMATION: Incyte ID No: 700300118H1

<400> SEQUENCE: 73
cgccgtcgtc ctccagcgca ggcctccggg ctccagctcc ggtgttgggt gcaggcctgg      60
tgtggtctcc aaagtgactg aacaatgcag aaggacagtg gcccactggt tcctttacat     120
tattatggtt tcggctatgc ggccctggtg gctactggtg ggattattgg ctatgcaaaa     180
gcaggtagtg tgccgtccct ggctgctgga ctcttctttg ggggcctggc aggcctgggt     240
gcctaccagc tgtctcagga ccccaggaac gtgtgggttt t                         281

<210> SEQ ID NO 74
<211> LENGTH: 292
<212> TYPE: DNA
<213> ORGANISM: Rattus norvegicus
<220> FEATURE:
<221> NAME/KEY: misc_feature
<223> OTHER INFORMATION: Incyte ID No: 700301710H1
<220> FEATURE:
<221> NAME/KEY: unsure
<222> LOCATION: 5
<223> OTHER INFORMATION: a, t, c, g, or other

<400> SEQUENCE: 74
cctgnacctc tgttcctgtg ctcccgccgt cgtcctccag cgcaggcctc cgggctccag      60
ctccggtgtt gggtgcaggc ctggtgtggt ctccaaagtg actgaacaat gcagaaggac     120
agtggcccac tggttccttt acattattat ggtttcggct atgcggccct ggtggctact     180
ggtgggatta ttggctatgc aaaagcaggt agtgtgccgt ccctggctgc tggactcttc     240
tttgggggcc tggcaggcct gggtgcctac cagctgtctc aggaccccag ga             292

<210> SEQ ID NO 75
<211> LENGTH: 289
<212> TYPE: DNA
<213> ORGANISM: Rattus norvegicus
<220> FEATURE:
<221> NAME/KEY: misc_feature
<223> OTHER INFORMATION: Incyte ID No: 700064344H1
<220> FEATURE:
<221> NAME/KEY: unsure
<222> LOCATION: 266, 284
<223> OTHER INFORMATION: a, t, c, g, or other

<400> SEQUENCE: 75
cagcgcaggc ctccgggctc cagctccggt gttgggtgtg ttcttacttt gcggattta      60 ccaccctgga attgttccgt acgcgcaggc gcgcgggcgc tctcccgtgc actctctgct    120
gagctagcgg actgcccgcc tctctaaaac gtcctgtaac tgcggttccg ggagtggaaa    180
cctaaacgcg cgtgcgcttc ttccacgcca cggaaaccgt gcaggcctgg tgtggtctcc    240
aaagtgatga acatgcagaa ggacantggc ccactggttc ttanatatt                289

<210> SEQ ID NO 76
<211> LENGTH: 276
<212> TYPE: DNA
<213> ORGANISM: Rattus norvegicus
<220> FEATURE:
<221> NAME/KEY: misc_feature
<223> OTHER INFORMATION: Incyte ID No: 701423273H1
<220> FEATURE:
<221> NAME/KEY: unsure
<222> LOCATION: 50
<223> OTHER INFORMATION: a, t, c, g, or other
```

<400> SEQUENCE: 76

```
agcgcaggcc tcagggctcc agctccggtg ttgggtgcag gcctggtgtn gtctccaaag      60
tgactgaaca atgcagaagg acagtgggcc actggttcct ttacattatt atggtttcgg     120
ctatgcggcc ctggtggcta ctggtgggat tattggctat gcaaaagcag gtagtgtgcc     180
gtccctggct gctggactct tctttggggg cctggcaggc ctgggtgcct accagctgtc     240
tcaggacccc aggaacgtgt gggttttcct agctac                               276
```

<210> SEQ ID NO 77
<211> LENGTH: 293
<212> TYPE: DNA
<213> ORGANISM: Rattus norvegicus
<220> FEATURE:
<221> NAME/KEY: misc_feature
<223> OTHER INFORMATION: Incyte ID No: 700225847H1
<220> FEATURE:
<221> NAME/KEY: unsure
<222> LOCATION: 16, 229
<223> OTHER INFORMATION: a, t, c, g, or other

<400> SEQUENCE: 77

```
ccgtcgtcct ccagcncagg cctccgggct ccagctccgg tgttgggtgc aggcctggtg      60
tggtctccaa agtgactgaa caatgcagaa ggacagtggg ccactggttc ctttacatta     120
ttatggtttc ggctatgcgg ccctggtggc tactggtggg attattggct atgcaaaagc     180
aggtagtgtg ccgtccctgg ctgctggact ctctttgggg cctggcang cctgggtgcc     240
taccagctgt ctcaggaccc cagaacgtgt gggtttccta gctacgtctg gga            293
```

<210> SEQ ID NO 78
<211> LENGTH: 274
<212> TYPE: DNA
<213> ORGANISM: Rattus norvegicus
<220> FEATURE:
<221> NAME/KEY: misc_feature
<223> OTHER INFORMATION: Incyte ID No: 701462776H1
<220> FEATURE:
<221> NAME/KEY: unsure
<222> LOCATION: 109
<223> OTHER INFORMATION: a, t, c, g, or other

<400> SEQUENCE: 78

```
tgctcccgcc gtcgtcctcc agcgcaggcc tccgggctcc agctccggtg ttgggtgcag      60
gcctggtgtg gtctccaaag tgactgaaca atgcagaagg acagtggcnc actggttcct    120
ttacattatt atggtttcgg ctatgcggcc ctggtggcta ctggtgggat tattggctat    180
gcaaaagcag gtagtgtgcc gtccctggct gctggactct tctttggggg cctggcaggc    240
ctgggtgcct accagctgtc tcaggacccc agga                                 274
```

<210> SEQ ID NO 79
<211> LENGTH: 282
<212> TYPE: DNA
<213> ORGANISM: Rattus norvegicus
<220> FEATURE:
<221> NAME/KEY: misc_feature
<223> OTHER INFORMATION: Incyte ID No: 700916803H1
<220> FEATURE:
<221> NAME/KEY: unsure
<222> LOCATION: 46
<223> OTHER INFORMATION: a, t, c, g, or other

<400> SEQUENCE: 79

```
gtgctcccgc cgtcgtcctc cagcgcaggc ctccgggctc cagctnccgg tgttgggtgt      60
```

```
gttcttactt tgcggatttt accaccctgg aattgttccg tacgcgcagg cgcgcgggc    120 tctcccgtgc actctctgct gagctagcgg actgcccgcc tctctaaaac gtcctgtaac    180
tgcggttccg ggagtggaaa cctaaacgcg cgtgcgcttc ttccacgcca cggaaaccgt    240
gcaggcctgg tgtggtctcc aaagtgactg aacaatgcag aa                      282

<210> SEQ ID NO 80
<211> LENGTH: 280
<212> TYPE: DNA
<213> ORGANISM: Rattus norvegicus
<220> FEATURE:
<221> NAME/KEY: misc_feature
<223> OTHER INFORMATION: Incyte ID No: 700478141H1

<400> SEQUENCE: 80
gccgtcgtcc tccagcgcag gcctccgggc tccagctccg gtgttgggtg caggcctggt     60
gtggtctcca aagtgatgaa caatgcagaa ggacagtggc ccactggttc ctttacatta    120
ttatggtttc ggctatgcgg ccctggtggc tactggtggg attattggct atgcaaaagc    180
aggtagtgtg ccgtccctgg ctgctggact cttctttggg ggcctggcag gcctgggtgc    240
ctaccagctg tctcaggacc ccaggaacgt gtgggttttc                          280

<210> SEQ ID NO 81
<211> LENGTH: 299
<212> TYPE: DNA
<213> ORGANISM: Rattus norvegicus
<220> FEATURE:
<221> NAME/KEY: misc_feature
<223> OTHER INFORMATION: Incyte ID No: 701646690H1
<220> FEATURE:
<221> NAME/KEY: unsure
<222> LOCATION: 2, 8, 56, 70, 73, 80, 99, 113, 115, 121, 161, 186,
      191, 277
<223> OTHER INFORMATION: a, t, c, g, or other

<400> SEQUENCE: 81
tncctccngg ctccagctcc ggtgttgggt gcaggcctgg tgtggtctcc aaagtnactg     60
aacaatgcan aangacagtn gcccactggt tcctttacnt tattatggtt tcngntatgc    120
ngccctggtg gctactggtg ggattattgg ctatgcaaaa ncaggtagtg tgccgtccct    180
ggctgntgga ntcttctttg gggcctggca ggcctgggt gcctaccagc tgtctcagga     240
ccccaggaac gtgtgggttt tcctagctac gtctggnact ttggctggca tatggggat     299

<210> SEQ ID NO 82
<211> LENGTH: 286
<212> TYPE: DNA
<213> ORGANISM: Rattus norvegicus
<220> FEATURE:
<221> NAME/KEY: misc_feature
<223> OTHER INFORMATION: Incyte ID No: 701624261H1
<220> FEATURE:
<221> NAME/KEY: unsure
<222> LOCATION: 18, 45-46, 171-172
<223> OTHER INFORMATION: a, t, c, g, or other

<400> SEQUENCE: 82
tctcctccac aggtgcangc ctggtgtggt ctccaaagtg actgnncaat gcagaaggac     60
agtggcccac tggttccttt acattattat ggtttcggct atgcggccct ggtggctact    120
ggtgggatta ttggctatgc aaaagcaggt agtgtgccgt ccctggctgc nngactcttc    180
tttgggggcc tggcaggcct gggtgcctac cagctgtctc aggaccccag gaacgtgtgg    240
gttttcctag ctacgtctgg gactttggct ggcattatgg ggatga                   286
```

<210> SEQ ID NO 83
<211> LENGTH: 266
<212> TYPE: DNA
<213> ORGANISM: Rattus norvegicus
<220> FEATURE:
<221> NAME/KEY: misc_feature
<223> OTHER INFORMATION: Incyte ID No: 700912920H1

<400> SEQUENCE: 83
gcagaaggac agtggcccac tggttccttt acattattat ggtttcggct atgcggccct      60
ggtggctact ggtgggatta ttggctatgc aaaagcaggt agtgtgccgt ccctggctgc     120
tggactcttc tttgggggcc tggcaggcct gggtgcctac cagctgtctc aggacvccag     180
gaacgtgtgg gttttcctag ctacgtctgg gactttggct ggcattatgg ggatgagatt     240
ctacaactct gggaaattta tgcctg                                          266

<210> SEQ ID NO 84
<211> LENGTH: 262
<212> TYPE: DNA
<213> ORGANISM: Rattus norvegicus
<220> FEATURE:
<221> NAME/KEY: misc_feature
<223> OTHER INFORMATION: Incyte ID No: 701482566H1

<400> SEQUENCE: 84
ctggctgctg gactcttctt tgggggcctg gcaggcctgg gtgcctacca gctgtctcag      60
gaccccagga acgtgtgggt tttcctagct acgtctggga ctttggctgg cattatgggg     120
atgagattct acaactctgg gaaatttatg cctgcaggtt tgatcgcggg agccagtttg     180
ctgatggttg ccaaacttgg acttagtatg ttgagttcac cccatccgta gtagccatag     240
ccctgcgtgg gctcatgatg ag                                              262

<210> SEQ ID NO 85
<211> LENGTH: 285
<212> TYPE: DNA
<213> ORGANISM: Rattus norvegicus
<220> FEATURE:
<221> NAME/KEY: misc_feature
<223> OTHER INFORMATION: Incyte ID No: 700270272H1
<220> FEATURE:
<221> NAME/KEY: unsure
<222> LOCATION: 33, 72, 75
<223> OTHER INFORMATION: a, t, c, g, or other

<400> SEQUENCE: 85
ctgttcctgt gctcccgccg tcgtcctcca gcncaggcct ccgggctcca gctccggtgt      60
tgggtgcagg cntgntgtgg tctccaaagt gactgaacaa tgcagaagga cagtggccca     120
ctggttcctt tacattatta tggtttcggc tatgcggccc tggtggctac tggtgggatt     180
attggctatg caaaagcagg tagtgtgccg tccctggcct gctggactct ctttgggg      240 cctgcaggc ctgggtgcct accagctgtc tcaggacccc aggaa                      285

<210> SEQ ID NO 86
<211> LENGTH: 268
<212> TYPE: DNA
<213> ORGANISM: Rattus norvegicus
<220> FEATURE:
<221> NAME/KEY: misc_feature
<223> OTHER INFORMATION: Incyte ID No: 700628520H1
<220> FEATURE:
<221> NAME/KEY: unsure
<222> LOCATION: 8

-continued

<223> OTHER INFORMATION: a, t, c, g, or other

<400> SEQUENCE: 86

| ctccagcnca ggcctccggg ctccagctcc ggtgttgggt gcaggcctgg tgtggtctcc | 60 |
| aaagtgactg aacaatgcag aaggacagtg gcccactggt tcctttacat tattatggtt | 120 |
| tcggctatgc ggccctggtg gctactggtg ggattattgg ctatgcaaaa gcaggtagtg | 180 |
| tgccgtccct ggctgctgga ctcttctttg ggggcctggc aggcctgggt gcctaccagc | 240 |
| tgtctcagga ccccaggaac gtgtgggt | 268 |

<210> SEQ ID NO 87
<211> LENGTH: 269
<212> TYPE: DNA
<213> ORGANISM: Rattus norvegicus
<220> FEATURE:
<221> NAME/KEY: misc_feature
<223> OTHER INFORMATION: Incyte ID No: 700534975H1
<220> FEATURE:
<221> NAME/KEY: unsure
<222> LOCATION: 129
<223> OTHER INFORMATION: a, t, c, g, or other

<400> SEQUENCE: 87

| tgctcccgcc gtcgtcctcc agcgcaggcc tccgggctcc agctccggtg ttgggtgcag | 60 |
| gcctggtgtg gtctccaaag tgactgaaca atgcagaagg acagtggctc actggttcct | 120 |
| ttacattant atggtttcgg ctatgcggcc ctggtggcta ctggtgggat tattggctat | 180 |
| gcaaaagcag gtagtgtgcc gtccctggct gctggactct ctttgggggg cctggcaggc | 240 |
| ctgggtgcct accagctgtc tcaggaccc | 269 |

<210> SEQ ID NO 88
<211> LENGTH: 262
<212> TYPE: DNA
<213> ORGANISM: Rattus norvegicus
<220> FEATURE:
<221> NAME/KEY: misc_feature
<223> OTHER INFORMATION: Incyte ID No: 700176004H1
<220> FEATURE:
<221> NAME/KEY: unsure
<222> LOCATION: 6, 43
<223> OTHER INFORMATION: a, t, c, g, or other

<400> SEQUENCE: 88

| tatgcngccc tggtggctac tggtgggatt attggctatg canaagcagg tagtgtgccg | 60 |
| tccctggctg ctggactctt ctttgggggc ctggcaggcc tgggtgccta ccagctgtct | 120 |
| caggacccca ggaacgtgtg ggttttccta gctacgtctg gactttggc tggcattatg | 180 |
| gggatgagat tctacaactc tgggaaattt atgcctgcag gtttgatcgc gggagccagt | 240 |
| ttgctgatgg ttgccaaact tg | 262 |

<210> SEQ ID NO 89
<211> LENGTH: 349
<212> TYPE: DNA
<213> ORGANISM: Rattus norvegicus
<220> FEATURE:
<221> NAME/KEY: misc_feature
<223> OTHER INFORMATION: Incyte ID No: 701609236H1
<220> FEATURE:
<221> NAME/KEY: unsure
<222> LOCATION: 48-49, 315, 344
<223> OTHER INFORMATION: a, t, c, g, or other

<400> SEQUENCE: 89

-continued

| | |
|---|---|
| cgtacgcgca ggcgcgcggg gctctcccgt gcactctctg gctgagcnng cggactgccc | 60 |
| gcctctctaa aacgtcctgt aactgcggtt ccgggagtgg aaacctaaac gcgcgtgcgc | 120 |
| ttcttccacg ccacggaaac cgtgcaggcc tggtgtggtc tccaaagtga ctgaacaatg | 180 |
| cagaaggaca gtggcccact ggttcccttta cattattatg gtttcggcta tgcggccctg | 240 |
| gtggctactg gtgggatatt ggctatgcaa aagcagtatg tgccgtccct ggctgctgga | 300 |
| ctctcttggg ggctngcagc ctggtgctaa caactgtctc agancccag | 349 |

<210> SEQ ID NO 90
<211> LENGTH: 263
<212> TYPE: DNA
<213> ORGANISM: Rattus norvegicus
<220> FEATURE:
<221> NAME/KEY: misc_feature
<223> OTHER INFORMATION: Incyte ID No: 701473437H1
<220> FEATURE:
<221> NAME/KEY: unsure
<222> LOCATION: 4, 49
<223> OTHER INFORMATION: a, t, c, g, or other

<400> SEQUENCE: 90

| | |
|---|---|
| agcncaggcc tccgggctcc agctccggtg ttgggtgcag gcctggtgng gtctccaaag | 60 |
| tgactgaaca atgcagaagg acagtggccc actggttcct ttacattatt atggtttcgg | 120 |
| ctatgcggcc ctggtggcta ctggtgggat tattggctat gcaaaagcag gtagtgtgcc | 180 |
| gtccctggct gctggactct ctttggggg cctggcaggc ctgggtgcct accagctgtc | 240 |
| tcaggacccc aggaacgtgt ggg | 263 |

<210> SEQ ID NO 91
<211> LENGTH: 303
<212> TYPE: DNA
<213> ORGANISM: Rattus norvegicus
<220> FEATURE:
<221> NAME/KEY: misc_feature
<223> OTHER INFORMATION: Incyte ID No: 701606089H1
<220> FEATURE:
<221> NAME/KEY: unsure
<222> LOCATION: 86, 96, 150, 187, 206, 215, 218, 244, 270, 289, 299
<223> OTHER INFORMATION: a, t, c, g, or other

<400> SEQUENCE: 91

| | |
|---|---|
| gcgcaggcct ccggggctcc agctccggtg ttgggtgcag gcctggtgtg gtctccaaag | 60 |
| tgactgaaca atgcagaagg acgttngccc actggntcct ttacattatt atggtttcgg | 120 |
| ctatgcggcc ctggtggcta ctggtgggan tattggctat gcaaaagcag gtagtgtgcc | 180 |
| gtccctngct gctggactct ctttngggg cctgncangc ctgggtgcct accagctgtc | 240 |
| tcangacccc aggaacgtgt gggttttccn agctacgtct gggatttgnc tggcatatng | 300 |
| gga | 303 |

<210> SEQ ID NO 92
<211> LENGTH: 273
<212> TYPE: DNA
<213> ORGANISM: Rattus norvegicus
<220> FEATURE:
<221> NAME/KEY: misc_feature
<223> OTHER INFORMATION: Incyte ID No: 701736525H2

<400> SEQUENCE: 92

| | |
|---|---|
| taactgctcc gacctctcct ccacaggtgc aggcctggtg tggtctccaa agtgactgaa | 60 |
| caatgcagaa ggacagtggc ccactggttc ctttacatta ttatggtttc ggctatgcgg | 120 |

-continued

| | |
|---|---|
| ccctggtggc tactggtggg attattggct atgcaaaagc aggtagtgtg ccgtccctgg | 180 |
| ctgctggact cttctttggg ggcctggcag gcctgggtgc ctaccagctg tctcaggacc | 240 |
| ccaggaacgt gtgggttttc ctagctacgt ctg | 273 |

<210> SEQ ID NO 93
<211> LENGTH: 262
<212> TYPE: DNA
<213> ORGANISM: Rattus norvegicus
<220> FEATURE:
<221> NAME/KEY: misc_feature
<223> OTHER INFORMATION: Incyte ID No: 701532848H1
<220> FEATURE:
<221> NAME/KEY: unsure
<222> LOCATION: 2, 9, 22, 25, 104
<223> OTHER INFORMATION: a, t, c, g, or other

<400> SEQUENCE: 93

| | |
|---|---|
| cngccgtcnt cctccagcgc angcntccgg gctccagctc cggtgttggg tgcaggcctg | 60 |
| gtgtggtctc caaagtgact gaacaatgca gaaggacagt ggcncactgg ttcctttaca | 120 |
| ttattatggt ttcggctatg cggccctggt ggctactggt gggattattg gctatgcaaa | 180 |
| agcaggtagt gtgccgtccc tggctgctgg actcttcttt gggggcctgg caggcctggg | 240 |
| tgcctaccag ctgtctcagg ac | 262 |

<210> SEQ ID NO 94
<211> LENGTH: 247
<212> TYPE: DNA
<213> ORGANISM: Rattus norvegicus
<220> FEATURE:
<221> NAME/KEY: misc_feature
<223> OTHER INFORMATION: Incyte ID No: 700181220H1

<400> SEQUENCE: 94

| | |
|---|---|
| aaaacgtcct gtaactgcgg ttccgggagt ggaaacctaa acgcgcgtgc gcttcttcca | 60 |
| cgccacggaa accgtgcagg cctggtgtgg tctccaaagt gactgaacaa tgcagaagga | 120 |
| cagtggccca ctggttcctt tacattatta tggtttcggc tatgcggccc tggtggctac | 180 |
| tggtgggatt attggctatg caaaagcagg tagtgtgccg tccctggctg ctggactctt | 240 |
| ctttggg | 247 |

<210> SEQ ID NO 95
<211> LENGTH: 284
<212> TYPE: DNA
<213> ORGANISM: Rattus norvegicus
<220> FEATURE:
<221> NAME/KEY: misc_feature
<223> OTHER INFORMATION: Incyte ID No: 701462707H1
<220> FEATURE:
<221> NAME/KEY: unsure
<222> LOCATION: 90
<223> OTHER INFORMATION: a, t, c, g, or other

<400> SEQUENCE: 95

| | |
|---|---|
| tacacacccg gctcctgacc tctgttcctg tgctcccgcc gtcgtcctcc agcgcaggcc | 60 |
| tccgggctcc agctccggtg ttgggtgcan gcctggtgtg gtctccaaag tgactgaaca | 120 |
| atgcagaagg acagtggccc actggttcct ttacattatt atggtttcgg ctatgcggcc | 180 |
| ctggtggcta ctggtgggat tattggctat gcaaaagcag gtagtgtgcc gtccctggct | 240 |
| gctggactct ctttgggggg cctggcaggc ctgggtgcct acca | 284 |

<210> SEQ ID NO 96

<210> SEQ ID NO 96
<211> LENGTH: 282
<212> TYPE: DNA
<213> ORGANISM: Rattus norvegicus
<220> FEATURE:
<221> NAME/KEY: misc_feature
<223> OTHER INFORMATION: Incyte ID No: 701462863H1

<400> SEQUENCE: 96

```
tacacacccg gctcctgacc tctgttcctg tgctcccgcc gtcgtcctcc agcgcaggcc      60
tccgggctcc agctccggtg ttgggtgcag gcctggtgtg gtctccaaag tgactgaaca     120
atgcagaagg acagtggccc actggttcct ttacattatt atggtttcgg ctatgcggcc     180
ctggtggcta ctggtgggat tattggctat gcaaaagcag gtagtgtgcc gtccctggct     240
gctggactct tctttggggg cctggcaggc ctgggtgcct ac                        282
```

<210> SEQ ID NO 97
<211> LENGTH: 281
<212> TYPE: DNA
<213> ORGANISM: Rattus norvegicus
<220> FEATURE:
<221> NAME/KEY: misc_feature
<223> OTHER INFORMATION: Incyte ID No: 701481465H1

<400> SEQUENCE: 97

```
ttcttaactg ctccgacctc tcctccacag gtgcaggcct ggtgtggtct ccaaagtgac      60
tgaacaatgc agaaggacag tggcccactg gttcctttac attattatgg tttcggctat     120
gcggccctgg tggctactgg tgggattatt ggctatgcaa aagcaggtag tgtgccgtcc     180
ctgggctgct ggactcttct ttgggggcct ggcaggcctg gtgcctacc agctgtctca     240
ggaccccagg aacgtgtggg ttttcctagc tacgtctggg a                         281
```

<210> SEQ ID NO 98
<211> LENGTH: 265
<212> TYPE: DNA
<213> ORGANISM: Rattus norvegicus
<220> FEATURE:
<221> NAME/KEY: misc_feature
<223> OTHER INFORMATION: Incyte ID No: 701308467H1
<220> FEATURE:
<221> NAME/KEY: unsure
<222> LOCATION: 57, 243, 246
<223> OTHER INFORMATION: a, t, c, g, or other

<400> SEQUENCE: 98

```
tgttcctgtg ctcccgccgt cgtcctccag cgcaggcctc cgggctccag ctccggngtt      60
gggtgcaggc tggtgtggt ctccaaagtg actgaacaat gcagaaggac agtggcccac     120
tggttccttt acattattat ggtttcggct atgcggccct ggtggctact ggtgggatta     180
ttggctatgc aaaagcaggt agtgtgccgt ccctggctgc tggactcttc tttgggggcc     240
tgnagnctgg gtgcctacca gctgt                                            265
```

<210> SEQ ID NO 99
<211> LENGTH: 291
<212> TYPE: DNA
<213> ORGANISM: Rattus norvegicus
<220> FEATURE:
<221> NAME/KEY: misc_feature
<223> OTHER INFORMATION: Incyte ID No: 701564368H1

<400> SEQUENCE: 99

```
gggggcctgg caggcctggg tgcctaccag ctgtctcagg accccaggaa cgtgtgggtt      60
tcctagcta cgtctgggac tttggctggc attatgggga tgagattcta caactctggg     120
```

```
aaatttatgc ctgcaggttt gatcgcggga gccagtttgc tgatggttgc caaacttgga    180
cttagtatgt tgagttcacc ccatccgtag tagccatagt cctgcgtggg ctcatgatga    240
gttgacactc tccagtcctc cacattacca cgctgaagag ataagaacag c             291

<210> SEQ ID NO 100
<211> LENGTH: 271
<212> TYPE: DNA
<213> ORGANISM: Rattus norvegicus
<220> FEATURE:
<221> NAME/KEY: misc_feature
<223> OTHER INFORMATION: Incyte ID No: 700533180H1

<400> SEQUENCE: 100
caggtagtgt gccgtccctg gctgctggac tcttctttgg gggcctggca ggcctgggtg     60
gcctaccagc tgtcctcagg aaccccagga acgtgtgggt tttcctagct acgtctggga   120
ctttggctgg cattatgggg atgagattct acaactctgg gaaatttatg cctgcaggtt   180
tgatcgcggg agccagtttg ctgatggttg ccaaacttgg acttagtatg ttgagttcac   240
cccatccgta gtagccatag tcctgcgtgg g                                  271

<210> SEQ ID NO 101
<211> LENGTH: 255
<212> TYPE: DNA
<213> ORGANISM: Rattus norvegicus
<220> FEATURE:
<221> NAME/KEY: misc_feature
<223> OTHER INFORMATION: Incyte ID No: 700124647H1
<220> FEATURE:
<221> NAME/KEY: unsure
<222> LOCATION: 16, 91, 243-244
<223> OTHER INFORMATION: a, t, c, g, or other

<400> SEQUENCE: 101
ccgtcgtcct ccagcncagg cctccgggct ccagctccgg tgttgggtgc aggcctggtg     60
tggtctccaa agtgactgaa caatgcagaa ngacagtggc ccactggttc ctttacatta   120
ttatggtttc ggctatgcgg ccctggtggc tactggtggg attattggct atgcaaaagc   180
aggtagtgtg ccgtccctgg ctgctggatc ttctttgggg gcctggcagg cctgggtgcc   240
tannagctgt ctcaa                                                    255

<210> SEQ ID NO 102
<211> LENGTH: 297
<212> TYPE: DNA
<213> ORGANISM: Rattus norvegicus
<220> FEATURE:
<221> NAME/KEY: misc_feature
<223> OTHER INFORMATION: Incyte ID No: 700537020H1
<220> FEATURE:
<221> NAME/KEY: unsure
<222> LOCATION: 66, 106, 159, 161
<223> OTHER INFORMATION: a, t, c, g, or other

<400> SEQUENCE: 102
gccctggtgg ctactggtgg gattattggc tatgcaaaag caggtagtgt gccgtccctg     60
gctgcnggac tcttctttgg gggcctggca ggcctgggtg cctacnagct aggctcagga   120
ccccaggaac gtgtgggttt tcctagctac tctggaccnt nggctggcat tatggggatg   180
agattctaca actctgggaa atttatgcct gcaggtttga tcgcgggagc cagtttgctg   240
atggttgcca aacttggact tagtatgttg agttcacccc atccgtagta gccatag      297
```

<210> SEQ ID NO 103
<211> LENGTH: 261
<212> TYPE: DNA
<213> ORGANISM: Rattus norvegicus
<220> FEATURE:
<221> NAME/KEY: misc_feature
<223> OTHER INFORMATION: Incyte ID No: 700765205H1

<400> SEQUENCE: 103

| gacctctgtt | cctgtgctcc | cgccgtcgtc | ctccagcgca | ggcctccggg | ctccagctcc | 60 |
| ggtgttgggt | gcaggcctgg | tgtggtctcc | aaagtgactg | aacaatgcag | aaggacagtg | 120 |
| gcccactggt | tcctttacat | tattatggtt | tcggctatgc | ggccctggtg | gctactggtg | 180 |
| ggattattgg | ctatgcaaaa | gcaggtagtg | tgccgtccct | ggctgctgga | ctcttctttg | 240 |
| ggggcctggc | aggctgggtg | c | | | | 261 |

<210> SEQ ID NO 104
<211> LENGTH: 312
<212> TYPE: DNA
<213> ORGANISM: Rattus norvegicus
<220> FEATURE:
<221> NAME/KEY: misc_feature
<223> OTHER INFORMATION: Incyte ID No: 701942992H1
<220> FEATURE:
<221> NAME/KEY: unsure
<222> LOCATION: 11, 119, 295, 301, 308, 310-311
<223> OTHER INFORMATION: a, t, c, g, or other

<400> SEQUENCE: 104

| cgacgtctac | ncacccggct | cctgacctct | gttcctgtgc | tccgccgtc | gtcctccagc | 60 |
| gcaggcctcc | gggctccagc | tccggtgttg | ggtgcaggcc | tggtgtggtc | tccaaagtna | 120 |
| ctgaacaatg | cagaaggaca | gtggcccact | ggttccttta | cattattatg | gtttcggcta | 180 |
| tgcggccctg | gtggctactg | gtgggattat | tggctatgca | aaagcaggta | gtgtgccgtc | 240 |
| cctggctgct | ggactcttct | ttgggggcct | ggcagcctgg | ggcctacaag | ttttntcagg | 300 |
| ncccaggnan | nt | | | | | 312 |

<210> SEQ ID NO 105
<211> LENGTH: 241
<212> TYPE: DNA
<213> ORGANISM: Rattus norvegicus
<220> FEATURE:
<221> NAME/KEY: misc_feature
<223> OTHER INFORMATION: Incyte ID No: 701197694H1
<220> FEATURE:
<221> NAME/KEY: unsure
<222> LOCATION: 233
<223> OTHER INFORMATION: a, t, c, g, or other

<400> SEQUENCE: 105

| tgctcccgcc | gtcgtcctcc | agcgcaggcc | tccgggctcc | agctccggtg | ttgggtgcag | 60 |
| gcctggtgtg | gtctccaaag | tgactgaaca | atgcagaagg | acagtggccc | actggttcct | 120 |
| ttacattatt | atggtttcgg | ctatgcggcc | ctggtggcta | ctggtgggat | tattggctat | 180 |
| gcaaaagcag | gaacgtgtgg | gttttcctag | ctacgtctgg | gactttggct | ggnattatgg | 240 |
| g | | | | | | 241 |

<210> SEQ ID NO 106
<211> LENGTH: 268
<212> TYPE: DNA
<213> ORGANISM: Rattus norvegicus
<220> FEATURE:
<221> NAME/KEY: misc_feature
<223> OTHER INFORMATION: Incyte ID No: 701024952H1
<220> FEATURE:
<221> NAME/KEY: unsure
<222> LOCATION: 111, 125, 245, 250
<223> OTHER INFORMATION: a, t, c, g, or other

<400> SEQUENCE: 106

```
cccggctcct gacctctgtt cctgtgctcc cgccgtcgtc ctccagcgca ggcctccggg      60
ctccagctcc ggtgttgggt gcaggcctgg tgtggtctcc aaagtgactg nacaatgcag     120
aaggncagtg gcccactggt tcctttacat tattatggtt tcggctatgc ggccctggtg     180
gctactggtg ggattattgg ctatgcaaaa gcaggtagtg tgccgtccct ggctgctgga     240
ctctncttta ggggcctggc aggcttag                                        268
```

<210> SEQ ID NO 107
<211> LENGTH: 318
<212> TYPE: DNA
<213> ORGANISM: Rattus norvegicus
<220> FEATURE:
<221> NAME/KEY: misc_feature
<223> OTHER INFORMATION: Incyte ID No: 701582676H1
<220> FEATURE:
<221> NAME/KEY: unsure
<222> LOCATION: 155
<223> OTHER INFORMATION: a, t, c, g, or other

<400> SEQUENCE: 107

```
gcctaccagc tgtctcagga ccccaggaac gtgtgggttt cctagctac gtctgggact      60
ttggctggca ttatggggat gagattctac aactctggga aatttatgcc tgcaggtttg    120
atcgcgggag ccagtttgct gatggttgcc aaacntggac ttagtatgtt gagttcaccc    180
catccgtagt agccatagtc ctgcgtgggc tcatgatgag ttgacactct ccagtcctcc    240
acattaccac gctgaagaga taagaacagc aaagacctac actgagcaca tggaggcgaa    300
gacgtggtta ctatagtg                                                  318
```

<210> SEQ ID NO 108
<211> LENGTH: 255
<212> TYPE: DNA
<213> ORGANISM: Rattus norvegicus
<220> FEATURE:
<221> NAME/KEY: misc_feature
<223> OTHER INFORMATION: Incyte ID No: 701293154H1

<400> SEQUENCE: 108

```
ggattattgg ctattgcaaa agcaggtaag tgtgccgtcc ctggctgctg gactcttctt      60
tgggggcctg gcaggcctgg gtgcctacca gctgtctcag gaccccagga acgtgtgggt    120
tttcctagct acgtctggga ctttggcttg cattatgggg atgagattct acaactctgg    180
gaaatttatg cctgcaggtt tgatcgcggg agccagtttg ctgatggttg ccaaacttgg    240
attagtatgt tgagg                                                    255
```

<210> SEQ ID NO 109
<211> LENGTH: 254
<212> TYPE: DNA
<213> ORGANISM: Rattus norvegicus
<220> FEATURE:
<221> NAME/KEY: misc_feature
<223> OTHER INFORMATION: Incyte ID No: 701298824H1
<220> FEATURE:
<221> NAME/KEY: unsure
<222> LOCATION: 53, 65, 119, 173, 221
<223> OTHER INFORMATION: a, t, c, g, or other -continued

```
<400> SEQUENCE: 109
catgcgcagg cctccgggct ccatgctccg gtgttgggtg catggcctgg tgnggtctcc      60
aaagngactg aacaatgcag aaggacagtg gcccactggt tcctttacat tattatggnt    120
tcggctatgc ggccctggtg gctactggtg ggattattgg ctatgcaaaa gcnggtagtg    180
tgccgccctg gctgctggac tcttctttgg gggcctgcag nctgggtgcc taccagctgt    240
ctcaggaccc agga                                                      254

<210> SEQ ID NO 110
<211> LENGTH: 294
<212> TYPE: DNA
<213> ORGANISM: Rattus norvegicus
<220> FEATURE:
<221> NAME/KEY: misc_feature
<223> OTHER INFORMATION: Incyte ID No: 700524204H1

<400> SEQUENCE: 110
tcaggacccc aggaacgtgt gggttttcct agctacgtct gggactttgg ctggcattat      60
ggggatgaga ttctacaact ctgggaaatt tatgcctgca ggtttgatcg cgggagccag    120
tttgctgatg gttgccaaac ttggacttag tatgttgagt cacccccatc cgtagtagcc    180
atagccctgc gtgggctcat gatgagttga cactctccag tcctctacat taccacgctg    240
aagagataag aacagcaaag acctacactg agcacatgga ggcgaagagt ggtt          294

<210> SEQ ID NO 111
<211> LENGTH: 289
<212> TYPE: DNA
<213> ORGANISM: Rattus norvegicus
<220> FEATURE:
<221> NAME/KEY: misc_feature
<223> OTHER INFORMATION: Incyte ID No: 700067537H1

<400> SEQUENCE: 111
gacgtctaca cacccggctc ctgacctctg ttcctgtgct cccgccgtcg tcctccagcg      60
caggcctccg ggctccagct ccgctgttgg gtgcaggcct ggtgtggtct ccaaagtgac    120
tgaacaatgc agaaggacag tggcccactg gttcctttac attattatgg tttcggctat    180
gcggccctgt ggctactggt gggattatt ggctatgcaa aagcagtagt gtgccgtccc     240
tggctgctgg atcttctttg ggggctggca ggctgggtgc ctacaactg                289

<210> SEQ ID NO 112
<211> LENGTH: 276
<212> TYPE: DNA
<213> ORGANISM: Rattus norvegicus
<220> FEATURE:
<221> NAME/KEY: misc_feature
<223> OTHER INFORMATION: Incyte ID No: 701258019H1
<220> FEATURE:
<221> NAME/KEY: unsure
<222> LOCATION: 145, 178, 248, 274
<223> OTHER INFORMATION: a, t, c, g, or other

<400> SEQUENCE: 112
tgttcctgtg ctcccgccgt cgtcctccag cgcaggcctc cgggctccag ctccggtgtt      60
gggtgcaggc ctggtgtggt ctccaaagtg actgaacaat gcatgaagga cagttggccc    120
actggttcct ttacattatt atggnttccg gctatgcggc cctggtggct actggtgnga    180
ttattggcta tgcaaaagca gtagtgtgc cgccctggct gctggactct ctttgggggg    240
cctgcagnct ggtgcctacc agctgctctg cgtngg                              276
```

```
<210> SEQ ID NO 113
<211> LENGTH: 254
<212> TYPE: DNA
<213> ORGANISM: Rattus norvegicus
<220> FEATURE:
<221> NAME/KEY: misc_feature
<223> OTHER INFORMATION: Incyte ID No: 700532493H1
<220> FEATURE:
<221> NAME/KEY: unsure
<222> LOCATION: 4, 52, 247
<223> OTHER INFORMATION: a, t, c, g, or other

<400> SEQUENCE: 113
tcangacccc aggaacgtgt gggttttcct agctacgtct gggactttgg cnggcattat    60
ggggctgaga ttctacaact ctgggaaatt tatgcctgca ggtttgatcg cgggagccag   120
tttgctgatg gttgccaaac ttggacttag tatgttgagt tcaccccatc cgtagtagcc   180
atagccctgc gtgggctcat gatgagttgc atctccagtc tctacatta ccacgctgaa   240 gagatanaac agca                                                    254

<210> SEQ ID NO 114
<211> LENGTH: 282
<212> TYPE: DNA
<213> ORGANISM: Rattus norvegicus
<220> FEATURE:
<221> NAME/KEY: misc_feature
<223> OTHER INFORMATION: Incyte ID No: 700523302H1
<220> FEATURE:
<221> NAME/KEY: unsure
<222> LOCATION: 8, 108, 114, 126, 128, 130-131, 136-139, 141-142, 150,
      153, 157-159,
<223> OTHER INFORMATION: a, t, c, g, or other

<400> SEQUENCE: 114
ctccagcnca ggcctccggg ctccagctcc ggtgttgggt gcaggcctgg tgtggtctcc    60
aaagtgactg aacaatgcag aaggacagtg gcccactggt tcctttanat aatnatggtc   120
gggtanangn ncccgnnnng nnaagggggn atnttgnnnt acgnaagagc ngntagtgtg   180
ccgtccctgg ctgctggact cttctttggg ggcctggcag gcctgggtgc ctaccagctg   240
tctcaggacc ccaggaacgg tgggtttccn agctacgncg gg                     282

<210> SEQ ID NO 115
<211> LENGTH: 256
<212> TYPE: DNA
<213> ORGANISM: Rattus norvegicus
<220> FEATURE:
<221> NAME/KEY: misc_feature
<223> OTHER INFORMATION: Incyte ID No: 701242719H1
<220> FEATURE:
<221> NAME/KEY: unsure
<222> LOCATION: 40, 43, 76, 183
<223> OTHER INFORMATION: a, t, c, g, or other

<400> SEQUENCE: 115 cacaccggc tcctgacctc tgttcctgtg ctcccgccgn cgncctccag cgcaggcctc     60
cgggctccag ctccgntgtt gggtgcaggc ctggtgtggt ctccaaagtg actgaacaat   120
gcagaaggac agtggcccac tggttccttt acattattat ggtttcggct atgcggccct   180
ggnggctact ggtgggatta ttggctatca aaagcaggta gtgtgccgcc ctggctgtgg   240
actcttcttt ggggcc                                                  256

<210> SEQ ID NO 116
<211> LENGTH: 244
```

-continued

<212> TYPE: DNA
<213> ORGANISM: Rattus norvegicus
<220> FEATURE:
<221> NAME/KEY: misc_feature
<223> OTHER INFORMATION: Incyte ID No: 701226025H1
<220> FEATURE:
<221> NAME/KEY: unsure
<222> LOCATION: 91
<223> OTHER INFORMATION: a, t, c, g, or other

<400> SEQUENCE: 116

```
cattattatg gtttcggcta tgcggccctg gtggctactg gtgggattat tggctatgca      60
aaagcaggta gtgtgccgcc ctggctgctg nctcttcttt ggaggcctgg caggcctggg     120
tgcctaccag ctgctcagga ccccaggaac gtgtgggttt tcctagctac gtctgggact     180
ttgctggcat tatggggatg agattctaca actctgggaa atttatcctg caggtttgat     240
cgcg                                                                  244
```

<210> SEQ ID NO 117
<211> LENGTH: 262
<212> TYPE: DNA
<213> ORGANISM: Rattus norvegicus
<220> FEATURE:
<221> NAME/KEY: misc_feature
<223> OTHER INFORMATION: Incyte ID No: 701293276H1
<220> FEATURE:
<221> NAME/KEY: unsure
<222> LOCATION: 102, 257, 260
<223> OTHER INFORMATION: a, t, c, g, or other

<400> SEQUENCE: 117

```
cgtctacaca cccggctcct gacctctgtt cctgtgctcc cgcccgtcgt cctccagcgc      60
aggcctccgg gctccagctc cggtgttggg tgcaggcctg gngtggtctc caaagtgact     120
gaacaatgca gaaggacagt ggcccactgg ttcctttaca ttattatggt ttcggctatc     180
ggcccttggt ggctactggt gggattattg gctatgcaaa agcaggtagt gtgccgtccc     240
tggctgtgga ctctctntgn gg                                              262
```

<210> SEQ ID NO 118
<211> LENGTH: 261
<212> TYPE: DNA
<213> ORGANISM: Rattus norvegicus
<220> FEATURE:
<221> NAME/KEY: misc_feature
<223> OTHER INFORMATION: Incyte ID No: 700493358H1
<220> FEATURE:
<221> NAME/KEY: unsure
<222> LOCATION: 173, 175, 190, 193, 196, 198, 207, 218, 226, 233-234,
       243-244, 249,
<223> OTHER INFORMATION: a, t, c, g, or other

<400> SEQUENCE: 118

```
caggcctggt gtggtctcca aagtgactga acaatgcaga aggacagtgg cccactggtt      60
cctttacatt attatggttt cggctatgcg gccctggtgg ctactggtgg gattattggc     120
tatgcaaaag caggtagtgt gccgtccctg ctgctggac tcttctttgg ggncntgca       180
ggcctgggtn canacnantg tctaggnccc caagaaagt gggttnccca aannagggg      240
ggnnttggnc canaaangga a                                               261
```

<210> SEQ ID NO 119
<211> LENGTH: 265
<212> TYPE: DNA
<213> ORGANISM: Rattus norvegicus
<220> FEATURE:

<221> NAME/KEY: misc_feature
<223> OTHER INFORMATION: Incyte ID No: 700533285H1

<400> SEQUENCE: 119

```
ccttgaactc atttcttcct gactgctaga ggcctgtgtg ttcttaactg ctccgacctc     60
tcctccacag gtgcaggcct ggtgtggtct ccaaagtgac tgaacaatgc agaaggacag    120
tggcccactg gttcctttac attattatgg tttcggctat gcggccctgg tggctactgg    180
tgggattatt ggtatgcaaa agcaggtagt gtgccgtccc tggctgctgg actcttcttt    240
gggggcctgg caggcctggg tgcct                                          265
```

<210> SEQ ID NO 120
<211> LENGTH: 247
<212> TYPE: DNA
<213> ORGANISM: Rattus norvegicus
<220> FEATURE:
<221> NAME/KEY: misc_feature
<223> OTHER INFORMATION: Incyte ID No: 700920823H1
<220> FEATURE:
<221> NAME/KEY: unsure
<222> LOCATION: 5
<223> OTHER INFORMATION: a, t, c, g, or other

<400> SEQUENCE: 120

```
cgtgnacgtc tacacacccg gctcctgacc tctgttcctg tgctcccgcc gtcgtcctcc     60
agcgcaggcc tcccgggctc cagctccggt gttgggtgca ggcctggtgt ggtctccaaa    120
gtgactgaac aatgcagaag gacagtggcc cactggttcc tttacattat tatggtttcg    180
gctatgcggc cctggtggct actggtggga ttattgctat gcaaaagcag gtagtctgcc    240
gctccct                                                              247
```

<210> SEQ ID NO 121
<211> LENGTH: 263
<212> TYPE: DNA
<213> ORGANISM: Rattus norvegicus
<220> FEATURE:
<221> NAME/KEY: misc_feature
<223> OTHER INFORMATION: Incyte ID No: 700627607H1
<220> FEATURE:
<221> NAME/KEY: unsure
<222> LOCATION: 222, 227, 238, 240, 244, 246, 251-252, 259, 261-262
<223> OTHER INFORMATION: a, t, c, g, or other

<400> SEQUENCE: 121

```
gacgtctaca cacccggctc ctgacctctg ttcctgtgct cccgccgtcg tcctccagcg     60
caggcctccg ggctccagct ccggtgttgg gtgcaggcct ggtgtggtct ccaaagtgac    120
tgaacaatgc agaaggacag tggcccactg gttcctttac attattatgg tttcggctat    180
gcggccctgg tggctactgg tgggattatt ggctatgcaa anccagntat cgccggcncn    240
ggcnanctcg nnccgaggng nnc                                            263
```

<210> SEQ ID NO 122
<211> LENGTH: 265
<212> TYPE: DNA
<213> ORGANISM: Rattus norvegicus
<220> FEATURE:
<221> NAME/KEY: misc_feature
<223> OTHER INFORMATION: Incyte ID No: 700437944H2
<220> FEATURE:
<221> NAME/KEY: unsure
<222> LOCATION: 6, 29, 63, 90, 92, 104, 113, 115, 123, 140, 157, 222,
       241, 257
<223> OTHER INFORMATION: a, t, c, g, or other -continued

<400> SEQUENCE: 122

| ctccgntgtt | gggtgcaggc | ctggtgtant | ctccaaagtg | actgaacaat | gaagcaggac | 60 |
| cantggccca | ctggttcctt | tacattattn | tngtttcggc | tatncggccc | tgntngctac | 120 |
| tgntgggatt | attggctatn | caaaagcagg | tagtgtnccg | tccctggctg | ctggactctt | 180 |
| ctttgggggc | ctgacaggct | gggtgcctac | cagctgtctc | angcacccca | ggaacgtgtg | 240 |
| ngttttccta | agctacntct | gggac | | | | 265 |

<210> SEQ ID NO 123
<211> LENGTH: 343
<212> TYPE: DNA
<213> ORGANISM: Rattus norvegicus
<220> FEATURE:
<221> NAME/KEY: misc_feature
<223> OTHER INFORMATION: Incyte ID No: 701582848H1
<220> FEATURE:
<221> NAME/KEY: unsure
<222> LOCATION: 88, 131, 152, 170, 192, 214, 278, 284, 295, 319, 331, 333
<223> OTHER INFORMATION: a, t, c, g, or other

<400> SEQUENCE: 123

| gctaccagct | gtctcaggac | ccaggaacgt | gtgggtttcc | tagctacgtc | tgggactttg | 60 |
| gctggcatta | tggggatgag | attctacnac | tctgggaaat | ttatgcctgc | aggtttgatc | 120 |
| gcgggagcca | nttgctgata | gttgccaact | tngacttagt | atgttgagtn | caccccatcc | 180 |
| gtagtagcat | ancctgcgtg | ggctcagatg | agtnacactc | tccaggcctc | cacatttacc | 240 |
| aggctgaaga | gtaagacagc | aaagactaca | tgagcacntg | aggnaaacgt | ggttntatat | 300 |
| gacgttcaag | acgcgatgnt | gactcagact | ncntgctcat | cgg | | 343 |

<210> SEQ ID NO 124
<211> LENGTH: 241
<212> TYPE: DNA
<213> ORGANISM: Rattus norvegicus
<220> FEATURE:
<221> NAME/KEY: misc_feature
<223> OTHER INFORMATION: Incyte ID No: 701305531H1
<220> FEATURE:
<221> NAME/KEY: unsure
<222> LOCATION: 14, 37, 48, 103, 107-108
<223> OTHER INFORMATION: a, t, c, g, or other

<400> SEQUENCE: 124

| gacgtctaca | cacncggctc | ctgacctctg | ttcctgngct | cccgccgncg | acctccagcg | 60 |
| caggcctccg | ggctccagct | ccggagttgg | gtgcaggcct | ggngtgnnct | ccaaagtgac | 120 |
| tgaacaatgc | agaaggacag | tggcccactg | gttcctttac | attattatgg | attcggctat | 180 |
| gcggccctgg | tggctactgg | tggattattg | gctatcaaaa | gcaggagtgt | ccgccctgct | 240 |
| g | | | | | | 241 |

<210> SEQ ID NO 125
<211> LENGTH: 155
<212> TYPE: DNA
<213> ORGANISM: Rattus norvegicus
<220> FEATURE:
<221> NAME/KEY: misc_feature
<223> OTHER INFORMATION: Incyte ID No: 700916103H1

<400> SEQUENCE: 125

| gtgctcccgc | cgtcgtcctc | cagcgcaggc | ctccgggctc | cagctccggt | gttgggtgca | 60 |
| ggcctggtgt | ggtctccaaa | gtgactgaac | aatgcagaag | gacagtggcc | cactggttcc | 120 | tttacattat tatggtttcg gctatgcggc cctgg 155

<210> SEQ ID NO 126
<211> LENGTH: 185
<212> TYPE: DNA
<213> ORGANISM: Rattus norvegicus
<220> FEATURE:
<221> NAME/KEY: misc_feature
<223> OTHER INFORMATION: Incyte ID No: 701294764H1
<220> FEATURE:
<221> NAME/KEY: unsure
<222> LOCATION: 25, 52, 68, 100, 112, 155, 164, 176
<223> OTHER INFORMATION: a, t, c, g, or other

<400> SEQUENCE: 126
ccgccgtcgt ccttcagcgc aaggnctccg ggctccagct ccggagttgg gngcaggcct    60 ggagtgggnct ccaaagtgac tgaacaatgc agaaggacan tggcccactg gntcctttac   120
attattatgg tttcggctat gcggccctgg aggcnactgg gggnatattg gctatncaaa   180
agcgg                                                                185

<210> SEQ ID NO 127
<211> LENGTH: 125
<212> TYPE: DNA
<213> ORGANISM: Rattus norvegicus
<220> FEATURE:
<221> NAME/KEY: misc_feature
<223> OTHER INFORMATION: Incyte ID No: 700066710H1
<220> FEATURE:
<221> NAME/KEY: unsure
<222> LOCATION: 19
<223> OTHER INFORMATION: a, t, c, g, or other

<400> SEQUENCE: 127
ctcttctttg ggggcctgnc caggctgggt gcctaccagc tgtctcagga ccccaggaac    60
gtgtgggttt tcctagctac gtctgggact ttggctggca ttatggggat gagattctac   120
aactc                                                                125

<210> SEQ ID NO 128
<211> LENGTH: 266
<212> TYPE: DNA
<213> ORGANISM: Rattus norvegicus
<220> FEATURE:
<221> NAME/KEY: misc_feature
<223> OTHER INFORMATION: Incyte ID No: 701471559H1
<220> FEATURE:
<221> NAME/KEY: unsure
<222> LOCATION: 12, 228
<223> OTHER INFORMATION: a, t, c, g, or other

<400> SEQUENCE: 128
tttatgcctg cnggtttgat cgcgggagcc agtttgctga tggttgccaa acttggactt    60
agtatgttga gttcacccca tccgtagtag ccatagccct gcgtgggctc atgatgagtt   120
gacactctcc agtcctctac attaccacgc tgaagagata agaacagcaa agacctacac   180
tgagcacatg gaggcgaaga cgtggttact atagtgaccg ttcagagntg gcgagtgtct   240
gacctcagag ctcacactgc cttcat                                         266

<210> SEQ ID NO 129
<211> LENGTH: 208
<212> TYPE: DNA
<213> ORGANISM: Rattus norvegicus
<220> FEATURE:
<221> NAME/KEY: misc_feature
<223> OTHER INFORMATION: Incyte ID No: 700325006H1

```
<220> FEATURE:
<221> NAME/KEY: unsure
<222> LOCATION: 35, 41, 51, 83, 91, 99, 137, 145, 148, 157-158, 186,
      188, 190, 192,
<223> OTHER INFORMATION: a, t, c, g, or other

<400> SEQUENCE: 129
ggcaggcctg ggtgcctacc agctgtctca ggacnccagg nacgtgtggg ntttcctaga    60
ctacgtctgt gactttggct gancattatt ngggatgana ttctaacaac tctgggaaat   120
ttatgcctgc aggtttnatc gcggncancc agtttgnntg atggttgcca aacttggact   180
tagtangntn anttcacccc ntgccgtc                                      208

<210> SEQ ID NO 130
<211> LENGTH: 263
<212> TYPE: DNA
<213> ORGANISM: Rattus norvegicus
<220> FEATURE:
<221> NAME/KEY: misc_feature
<223> OTHER INFORMATION: Incyte ID No: 701258479H1
<220> FEATURE:
<221> NAME/KEY: unsure
<222> LOCATION: 154, 217, 246, 249
<223> OTHER INFORMATION: a, t, c, g, or other

<400> SEQUENCE: 130
gcagagctag ggcgagcaag tggctgtgtg ttcaagggcc agttgcatcc gcacccagtg    60
cttgtacctt gaactcattt cttcctgact gctagaggcc tgtgtgttct taactgctcc   120
gacctctcct ccacaggtgc aggcctggtg tggnctccaa agtgactgaa caatgcagaa   180
ggacagtggc ccactggctc ctttacatta ttatggnttc ggctatgcgg cctggtggct   240
actggnggna ttattggcta tgc                                          263

<210> SEQ ID NO 131
<211> LENGTH: 258
<212> TYPE: DNA
<213> ORGANISM: Rattus norvegicus
<220> FEATURE:
<221> NAME/KEY: misc_feature
<223> OTHER INFORMATION: Incyte ID No: 700627187H1
<220> FEATURE:
<221> NAME/KEY: unsure
<222> LOCATION: 25, 56
<223> OTHER INFORMATION: a, t, c, g, or other

<400> SEQUENCE: 131
aatttatgcc tgcaggttga tcgcnggagc cagtttgctg atggttgcca aacttngact    60
taggatgttg agttcacccc atcccggagt agccatagtc ctgcgtgggc tcatgatgag   120
ttgacactct ccagtcctcc acattaccac gctgaagaga taagaacagc aaagacctac   180
actgagcaca tggaggcgaa gacgtggtta ctatagtgac cgttcagaga cggcgagtgt   240
ctgactcaga gctcacac                                                258

<210> SEQ ID NO 132
<211> LENGTH: 272
<212> TYPE: DNA
<213> ORGANISM: Rattus norvegicus
<220> FEATURE:
<221> NAME/KEY: misc_feature
<223> OTHER INFORMATION: Incyte ID No: 701246066H1
<220> FEATURE:
<221> NAME/KEY: unsure
<222> LOCATION: 23, 42, 51, 59, 61, 116, 140, 253, 271
<223> OTHER INFORMATION: a, t, c, g, or other
```

```
<400> SEQUENCE: 132
gcgggagcca gtttgctgat ggntgccaaa cttggactta gnatgttgag ntcaccccnt      60
ncgtagtagc catagtcctg cgtggtctca tgatgagttg acactctcca gtcctncaca     120
ttaccacgct gaagagatan aacagcaaa gacctacact gagcacatgg aggcgaagac      180
gtggttacta tagtgaccgt tcagagacgg cgagtgtctg acctcagagc tcacactgct    240
tcatgcggct tgntcttgtg catgatgctc ng                                  272

<210> SEQ ID NO 133
<211> LENGTH: 253
<212> TYPE: DNA
<213> ORGANISM: Rattus norvegicus
<220> FEATURE:
<221> NAME/KEY: misc_feature
<223> OTHER INFORMATION: Incyte ID No: 700594190H1

<400> SEQUENCE: 133
atccgtagta gccatagccc tgcgtgggct catgatgagt tgacactctc cagtcctcta    60
cattaccacg ctgaagagat aagaacagca aagacctaca ctgagcacat ggaggcgaag   120
acgtggttac tatagtgacc gttcagagac ggcgagtgtc tgacctcaga gctcacactg   180
ccttcatgcg gcttgttctt gtgtcatgat gtctcgactc tctgtactac tacataaagg   240
ggtaaaatgt tgg                                                      253

<210> SEQ ID NO 134
<211> LENGTH: 267
<212> TYPE: DNA
<213> ORGANISM: Rattus norvegicus
<220> FEATURE:
<221> NAME/KEY: misc_feature
<223> OTHER INFORMATION: Incyte ID No: 700627108H1
<220> FEATURE:
<221> NAME/KEY: unsure
<222> LOCATION: 9, 62, 66, 84, 107, 110, 114, 123-124, 151, 156, 162,
      170, 180, 247,
<223> OTHER INFORMATION: a, t, c, g, or other

<400> SEQUENCE: 134
gaattgatnc ctggcaggtt gatcgcggga gccagttttg ctgatggttg acaaactttg    60
gncttngtat ctgagttcaa cccnatcggt agtagccata agtctanccn gggntcatga   120
tgnnttgaac actctccagt cagtccagat naacgncgct gntagagatn aagaccagcn   180
aagacctaca ctgagcacca tggaggcgaa gacgtggtta ctataagtga ccgttcagag   240
acggcgngtg tntggatcan agatcca                                       267

<210> SEQ ID NO 135
<211> LENGTH: 650
<212> TYPE: DNA
<213> ORGANISM: Rattus norvegicus
<220> FEATURE:
<221> NAME/KEY: misc_feature
<223> OTHER INFORMATION: Incyte ID No: 700RnAUG

<400> SEQUENCE: 135
gtgctcccgc cgtcgtcctc cagcgcaggc ctccgggctc cagctccggt gttgggtgtg    60
ttcttacttt gcggatttta ccaccctgga attgttccgt acgcgcaggc gcgcgggcgc   120
tctcccgtgc actctctgct gagctagcgg actgcccgcc tctctaaaac gtcctgtaac   180
tgcggttccg ggagtggaaa cctaaacgcg cgtgcgcttc ttccacgcca cggaaaccgt   240
gcaggcctgg tgtggtctcc aaagtgactg aacaatgcag aaggacagtg gcccactggt   300
```

```
tcctttacat tattatggtt tcggctatgc ggccctggtg gctactggtg ggattattgg    360
ctatgcaaaa gcaggtagtg tgccgtccct ggctgctgga ctcttctttg ggggcctggc    420
aggcctgggt gcctaccagc tgtctcagga ccccaggaac gtgtgggttt tcctagctac    480
gtctgggact ttggctggca ttatgggat gagattctac aactctggga aatttatgcc     540
tgcaggtttg atcgcgggag ccagtttgct gatggttgcc aaacttggac ttagtatgtt    600
gagttcaccc catccgtagt agccatagcc ctgcgtgggc tcatgatgag              650
```

<210> SEQ ID NO 136
<211> LENGTH: 114
<212> TYPE: PRT
<213> ORGANISM: Rattus norvegicus
<220> FEATURE:
<221> NAME/KEY: misc_feature
<223> OTHER INFORMATION: Incyte ID No: 700RnAUG

<400> SEQUENCE: 136

```
Met Gln Lys Asp Ser Gly Pro Leu Val Pro Leu His Tyr Tyr Gly
 1               5                  10                  15

Phe Gly Tyr Ala Ala Leu Val Ala Thr Gly Gly Ile Ile Gly Tyr
                20                  25                  30

Ala Lys Ala Gly Ser Val Pro Ser Leu Ala Ala Gly Leu Phe Phe
                35                  40                  45

Gly Gly Leu Ala Gly Leu Gly Ala Tyr Gln Leu Ser Gln Asp Pro
                50                  55                  60

Arg Asn Val Trp Val Phe Leu Ala Thr Ser Gly Thr Leu Ala Gly
                65                  70                  75

Ile Met Gly Met Arg Phe Tyr Asn Ser Gly Lys Phe Met Pro Ala
                80                  85                  90

Gly Leu Ile Ala Gly Ala Ser Leu Leu Met Val Ala Lys Leu Gly
                95                 100                 105

Leu Ser Met Leu Ser Ser Pro His Pro
               110
```

<210> SEQ ID NO 137
<211> LENGTH: 223
<212> TYPE: DNA
<213> ORGANISM: Homo sapiens
<220> FEATURE:
<221> NAME/KEY: misc_feature
<223> OTHER INFORMATION: Incyte ID No: 746355H1

<400> SEQUENCE: 137

```
ctacgcagca ctggttgctt ctggtgggat cattggctat gtaaaagcag gcagcgtgcc     60
gtccctggct gcagggctgc tctttggcag tctagccggc ctgggtgctt accagctgtc    120
tcaggatcca aggaacgttt gggttttcct agctacatct ggtaccttgg ctggcattat    180
gggaatgagg ttctaccact ctggaaaatt catgcctgca ggt                      223
```

<210> SEQ ID NO 138
<211> LENGTH: 243
<212> TYPE: DNA
<213> ORGANISM: Homo sapiens
<220> FEATURE:
<221> NAME/KEY: misc_feature
<223> OTHER INFORMATION: Incyte ID No: 1294663H1

<400> SEQUENCE: 138

```
ggaaaattca tgcctgtagg tttaattgca ggtgccagtt tgctgatggc cgccaaagtt     60
```

-continued

```
ggagttcgta tgttgatgac atctgattag cagaagtcat gttccagctt ggactcatga    120
aggattaaaa atctgcatct tccactattt tcaatgtatt aagagaaata agtgcagcat    180
ttttgcatct gacattttac ctaaaaaaaa aaagacacca aatttggcgg aggggtggaa    240
aat                                                                  243
```